(12) United States Patent
Ihara et al.

(10) Patent No.: US 9,153,836 B2
(45) Date of Patent: Oct. 6, 2015

(54) ELECTROLYTIC SOLUTIONS AND BATTERY

(75) Inventors: Masayuki Ihara, Fukushima (JP);
Hiroyuki Yamaguchi, Fukushima (JP);
Tadahiko Kubota, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 1141 days.

(21) Appl. No.: 12/183,153

(22) Filed: Jul. 31, 2008

(65) Prior Publication Data

US 2009/0053612 A1 Feb. 26, 2009

(30) Foreign Application Priority Data

| Aug. 23, 2007 | (JP) | ................................. | 2007-216866 |
| Aug. 27, 2007 | (JP) | ................................. | 2007-219914 |
| Aug. 27, 2007 | (JP) | ................................. | 2007-219915 |

(51) Int. Cl.

| H01M 10/0569 | (2010.01) |
| H01M 10/052 | (2010.01) |
| C07C 309/80 | (2006.01) |
| C07C 309/81 | (2006.01) |
| C07C 309/82 | (2006.01) |
| C07C 309/86 | (2006.01) |
| H01M 10/0567 | (2010.01) |
| H01M 10/0568 | (2010.01) |

(52) U.S. Cl.
CPC ........... *H01M 10/052* (2013.01); *C07C 309/80* (2013.01); *C07C 309/81* (2013.01); *C07C 309/82* (2013.01); *C07C 309/86* (2013.01); *H01M 10/0567* (2013.01); *H01M 10/0568* (2013.01); *H01M 10/0569* (2013.01); *Y02E 60/122* (2013.01)

(58) Field of Classification Search
CPC .................................................. H01M 10/0569
USPC .................................................. 429/122–347
See application file for complete search history.

(56) References Cited

U.S. PATENT DOCUMENTS

| 5,633,099 A | 5/1997 | Yokoyama et al. |
| 5,659,062 A | 8/1997 | Yokoyama et al. |
| 6,436,582 B1 | 8/2002 | Hamamoto et al. |
| 7,241,536 B2 | 7/2007 | Kim et al. |
| 7,255,966 B2 | 8/2007 | Kim et al. |

(Continued)

FOREIGN PATENT DOCUMENTS

| CN | 1465117 | 12/2003 |
| CN | 1943071 | 4/2007 |

(Continued)

OTHER PUBLICATIONS

Notification of the First Office Action issued in connection with Chinese Patent Application No. 201310144332.2, dated Oct. 23, 2014. (35 pages).

*Primary Examiner* — Jonathan G Leong
(74) *Attorney, Agent, or Firm* — K&L Gates LLP

(57) ABSTRACT

A battery capable of improving battery characteristics is provided. The battery includes a cathode, an anode and an electrolytic solution, and a separator arranged between the cathode and the anode is impregnated with the electrolytic solution. The solvent of the electrolytic solution includes a sulfone compound having a sulfonyl fluoride type structure in which a sulfonyl group and a fluorine group are bonded together, and at least one kind selected from the group consisting of a chain carbonate which includes a halogen and a cyclic carbonate which includes a halogen.

11 Claims, 4 Drawing Sheets

(56) References Cited

U.S. PATENT DOCUMENTS

| | | | |
|---|---|---|---|
| 7,776,476 B2 * | 8/2010 | Ihara et al. | 429/231.95 |
| 2003/0165733 A1 | 9/2003 | Takehara et al. | |
| 2004/0034253 A1 * | 2/2004 | Angell et al. | 568/6 |
| 2006/0134528 A1 * | 6/2006 | Ihara et al. | 429/329 |
| 2006/0286459 A1 | 12/2006 | Zhao et al. | |
| 2007/0077490 A1 * | 4/2007 | Kim et al. | 429/218.1 |
| 2007/0224514 A1 * | 9/2007 | Kotato et al. | 429/325 |

FOREIGN PATENT DOCUMENTS

| | | |
|---|---|---|
| CN | 1983707 | 6/2007 |
| JP | 2000-133304 | 5/2000 |
| JP | 3294400 | 6/2002 |
| JP | 2002-359001 | 12/2002 |
| JP | 2004-014134 | 1/2004 |
| JP | 2004-022336 | 1/2004 |
| JP | 3760539 | 1/2006 |
| JP | 2006-049112 | 2/2006 |
| JP | 2006-049152 | 2/2006 |
| JP | 2006-172721 | 6/2006 |
| JP | 2006-172950 | 6/2006 |
| JP | 2006-190635 | 7/2006 |
| JP | 2006-244776 | 9/2006 |
| JP | 2006-261092 | 9/2006 |
| JP | 2006-294519 | 10/2006 |
| JP | 2006-331866 | 12/2006 |
| JP | 2006-339010 | 12/2006 |
| JP | 2006-344391 | 12/2006 |
| JP | 2006-351337 | 12/2006 |
| JP | 2007-080620 | 3/2007 |
| JP | 2007-157536 | 6/2007 |
| JP | 2007-172990 | 7/2007 |
| JP | 2007-179883 | 7/2007 |
| WO | WO 2005114773 A1 * | 12/2005 |
| WO | 2007-043526 | 4/2007 |

* cited by examiner

ELECTROLYTIC SOLUTIONS AND BATTERY

CROSS REFERENCES TO RELATED APPLICATIONS

The present application claims priority to Japanese Patent Application JP 2007-216866 filed in the Japanese Patent Office on Aug. 23, 2007, Japanese Patent Application JP 2007-219914 filed in the Japanese Patent Office on Aug. 27, 2007, and Japanese Patent Application JP 2007-219915 filed in the Japanese Patent Office on Aug. 27, 2007, the entire contents of which are being incorporated herein by reference.

BACKGROUND

The present disclosure relates to an electrolytic solution including a solvent, and a battery using the electrolytic solution.

In recent years, portable electronic devices such as camera-integrated VTRs (videotape recorders), cellular phones, or laptop computers are widely used, and size and weight reduction in the portable electronic devices and an increase in longevity of the portable electronic devices have been strongly demanded. Accordingly, as power sources for the portable electronic devices, the development of batteries, specifically lightweight secondary batteries capable of obtaining a high energy density have been promoted.

Among them, a secondary battery (a so-called lithium-ion secondary battery) using insertion and extraction of lithium for charge-discharge reaction, a secondary battery (so-called lithium metal secondary battery) using precipitation and dissolution of lithium, or the like holds great promise, because the secondary batteries are capable of obtaining a large energy density, compared to a lead-acid battery or a nickel-cadmium battery.

As an electrolytic solution for the secondary batteries, a combination of a carbonate-based solvent such as propylene carbonate or diethyl carbonate and an electrolyte salt such as lithium hexafluorophosphate is widely used (for example, refer to Japanese Patent No. 3294400). It is because the combination has high conductivity, and its potential is stable.

In addition, regarding the composition of an electrolytic solution, to improve cycle characteristics, storage characteristics and the like, techniques of including various sulfone compounds in an electrolytic solution have been proposed. As the sulfone compounds, a compound having a sulfonyl fluoride type structure (for example, refer to Japanese Unexamined Patent Application Publication Nos. 2002-359001, 2006-049112, 2006-049152 and 2006-294519), disulfonic anhydrides (for example, refer to Japanese Unexamined Patent Application Publication Nos. 2004-022336 and 2006-344391 and Japanese Patent No. 3760539), disulfonate derivatives (for example, refer to Japanese Unexamined Patent Application Publication Nos. 2000-133304, 2006-3513337 and 2007-080620) and the like are used.

In recent years, as portable electronic devices have higher performance and more functions, the power consumption of the portable electronic devices tends to increase. Accordingly, secondary batteries used in the portable electronic devices are frequently charged and discharged, thereby the cycle characteristics of the secondary batteries easily decline. Moreover, the portable electronic devices are widely used in various fields, and there is a possibility that the secondary batteries are exposed to a high-temperature atmosphere during transport, in use or during carrying, so the storage characteristics of the secondary batteries also decline easily. Further, in the case where a secondary battery includes a film-shaped package member, when the secondary battery is exposed to a high-temperature atmosphere, the secondary battery is easily swelled, so swelling characteristics are also important. Therefore, further improvement in battery characteristics such as cycle characteristics, storage characteristics and swelling characteristics of the secondary batteries is desired.

In view of the foregoing, it is desirable to provide an electrolytic solution and a battery which are capable of improving battery characteristics.

SUMMARY

According to an embodiment, there is provided a first electrolytic solution including: a solvent including a sulfone compound represented by Chemical Formula 1.

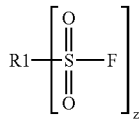

Chemical Formula 1 where R1 represents a z-valent group including carbon and one kind or two or more kinds of elements selected from the group consisting of hydrogen, oxygen and halogens, a sulfur atom in a sulfonyl group is bonded to a carbon atom in R1, z is an integer of 2 or more, and in the case where R1 is a straight-chain alkylene group or a halogenated alkylene group, the number of carbon atoms is 2 or less.

According to an embodiment, there is provided a first secondary battery including a cathode, an anode and an electrolytic solution, in which the electrolytic solution includes a sulfone compound represented by Chemical Formula 2.

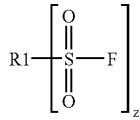

Chemical Formula 2 where R1 represents a z-valent group including carbon and one kind or two or more kinds of elements selected from the group consisting of hydrogen, oxygen and halogens, a sulfur atom in a sulfonyl group is bonded to a carbon atom in R1, z is an integer of 2 or more, and in the case where R1 is a straight-chain alkylene group or a halogenated alkylene group, the number of carbon atoms is 2 or less.

According to an embodiment, there is provided a second electrolytic solution including: a solvent including a sulfone compound represented by Chemical Formula 3 and at least one kind selected from the group consisting of a chain carbonate represented by Chemical Formula 4 which includes a halogen and a cyclic carbonate represented by Chemical Formula 5 which includes a halogen.

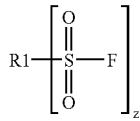

Chemical Formula 3 where R1 represents a z-valent group including carbon and one kind or two or more kinds of elements selected from the group consisting of hydrogen, oxygen and halogens, a sulfur atom in a sulfonyl group is bonded to a carbon atom in R1, and z is an integer of 2 or more.

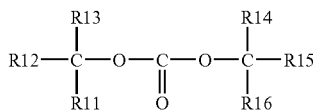

Chemical Formula 4 where R11, R12, R13, R14, R15 and R16 each represent a hydrogen group, a halogen group, an alkyl group or a halogenated alkyl group, and at least one of them is a halogen group or a halogenated alkyl group.

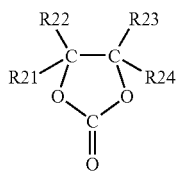

Chemical Formula 5 where R21, R22, R23 and R24 each represent a hydrogen group, a halogen group, an alkyl group or a halogenated alkyl group, and at least one of them is a halogen group or a halogenated alkyl group.

According to an embodiment, there is provided a second secondary battery including a cathode, an anode and an electrolytic solution, in which the electrolytic solution includes a solvent including a sulfone compound represented by Chemical Formula 6 and at least one kind selected from the group consisting of a chain carbonate represented by Chemical Formula 7 which includes a halogen and a cyclic carbonate represented by Chemical Formula 8 which includes a halogen.

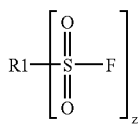

Chemical Formula 6 where R1 represents a z-valent group including carbon and one kind or two or more kinds of elements selected from the group consisting of hydrogen, oxygen and halogens, a sulfur atom in a sulfonyl group is bonded to a carbon atom in R1, and z is an integer of 2 or more.

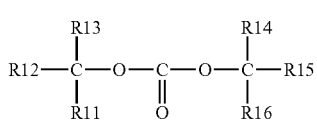

Chemical Formula 7 where R11, R12, R13, R14, R15 and R16 each represent a hydrogen group, a halogen group, an alkyl group or a halogenated alkyl group, and at least one of them is a halogen group or a halogenated alkyl group.

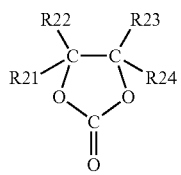

Chemical Formula 8 where R21, R22, R23 and R24 each represent a hydrogen group, a halogen group, an alkyl group or a halogenated alkyl group, and at least one of them is a halogen group or a halogenated alkyl group.

According to an embodiment, there is provided a third electrolytic solution including: a solvent including a sulfone compound represented by Chemical Formula 9.

Chemical Formula 9 where R1 is a chain group including a carbon-carbon unsaturated bond or a derivative thereof.

According to an embodiment, there is provided a third secondary battery including a cathode, an anode and an electrolytic solution, in which the electrolytic solution includes a solvent including a sulfone compound represented by Chemical Formula 10.

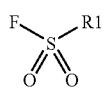

Chemical Formula 10 where R1 is a chain group including a carbon-carbon unsaturated bond or a derivative thereof.

In the first electrolytic solution according to the embodiment, the solvent includes the sulfone compound represented by Chemical Formula 1. Therefore, compared to the case where the sulfone compound is not included, or the case where another sulfone compound is included, the chemical stability is improved. Thereby, in the first secondary battery according to the embodiment, the decomposition reaction of the electrolytic solution is prevented, so cycle characteristics and storage characteristics are able to be improved.

In the second electrolytic solution according to the embodiment, the solvent includes the sulfone compound represented by Chemical Formula 3 and at least one kind selected from the group consisting of the chain carbonate represented by Chemical Formula 4 which includes a halogen and the cyclic carbonate represented by Chemical Formula 5 which includes a halogen, so compared to the case where neither of them is included, or the case where only one of them is included, the chemical stability is improved. Thereby, in the second secondary battery according to the embodiment, the decomposition reaction of the electrolytic solution is prevented, so battery characteristics such as cycle characteristics, storage characteristics and swelling characteristics are able to be improved.

In the third electrolytic solution according to the embodiment, the solvent includes the sulfone compound represented by Chemical Formula 9, so compared to the case where the sulfone compound is not included, or the case where another sulfone compound is included, the chemical stability is improved. Thereby, in the third secondary battery according to the embodiment, the decomposition reaction of the electrolytic solution is prevented, so cycle characteristics are able to be improved.

Additional features and advantages are described herein, and will be apparent from the following Detailed Description and the figures.

DETAILED DESCRIPTION

Figure 1:
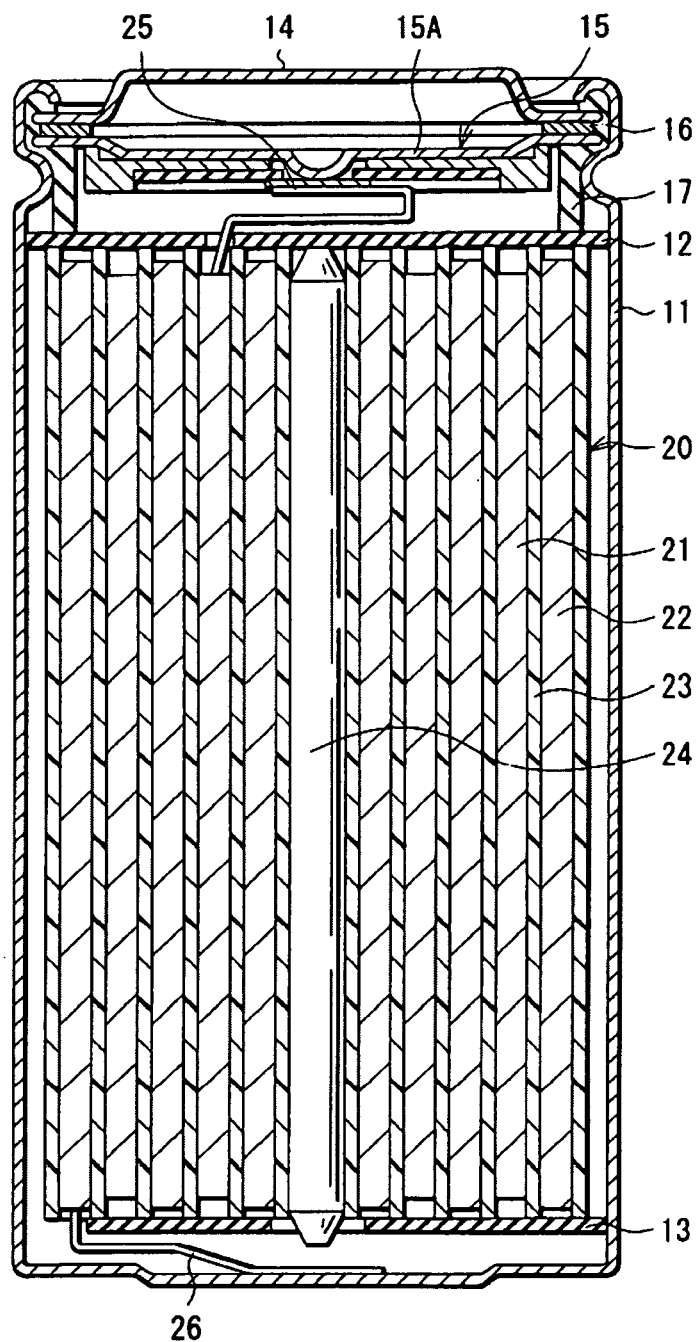
FIG. 1 is a sectional view showing the configuration of a first secondary battery using an electrolytic solution according to an embodiment.

Embodiments will be described in detail below referring to the accompanying drawings.

First Embodiment

An electrolytic solution according to a first embodiment is used in, for example, an electrochemical device such as a secondary battery, and includes a solvent and an electrolyte salt dissolved in the solvent.

The solvent includes one kind or two or more kinds of sulfone compounds represented by Chemical Formula 11. It is because the chemical stability of the electrolytic solution is improved. The sulfone compound represented by Chemical Formula 11 has a sulfonyl fluoride type structure in which a sulfonyl group (—SO$_2$—) and a fluorine group (—F—) are bonded together.

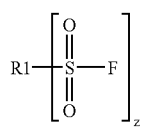

Chemical Formula 11 where R1 represents a z-valent group including carbon and one kind or two or more kinds of elements selected from the group consisting of hydrogen, oxygen and halogens, a sulfur atom in a sulfonyl group is bonded to a carbon atom in R1, z is an integer of 2 or more, and in the case where R1 is a straight-chain alkylene group or a halogenated alkylene group, the number of carbon atoms is 2 or less.

R1 in Chemical Formula 11 is a group having a carbon chain or a carbon ring as a basic skeleton, and in the basic skeleton, one kind or two or more kinds of elements selected from the group consisting of hydrogen, oxygen and halogens may be included in any form. The carbon chain may be a straight chain or a branched chain having 1 or 2 or more side chains.

The above-described "form" means the number of elements, a combination of elements and the like, and they are freely settable. More specifically, as a form of hydrogen, for example, a part of an alkylene group or an arylene group is cited. As a form of oxygen, for example, an ether bond (—O—) or the like is cited. As a form of halogens, for example, a part of a halogenated alkylene group or the like is cited. The kind of halogen is not specifically limited, but fluorine is preferable among halogens, because compared to other halogens, the chemical stability of the electrolytic solution is improved. In the above-described form of halogens, a halogen is substituted for hydrogen in R1. In this case, the halogen may be substituted for a part of hydrogen, or all of hydrogen. The forms of hydrogen, oxygen and halogens may be any form other than the above-described forms.

As long as R1 has the above-described structure, R1 may be any group. However, a sulfur atom in a number z of sulfonyl groups is not bonded to an atom (for example, an oxygen atom) except for a carbon atom in R1, and the sulfur atom is necessarily bonded to a carbon atom. Moreover, in the case where R1 is a straight-chain alkylene group or a halogenated alkylene group, the number of carbon atoms is limited to 2 or less (that is, 1 or 2). It is because compared to the case where the number of carbon atoms is 3 or more, the chemical stability of the electrolytic solution is improved, and superior compatibility is obtained. The "halogenated alkylene group" is a group obtained by substituting a halogen for at least a part of hydrogen in an alkylene group.

R1 may be a derivative of a group obtained by the above-described forms, and in this case, any other elements except for hydrogen, oxygen and halogens may be included as a constituent element. The "derivative" means a group obtained by introducing one or two or more substituent groups into the above-described groups, and the kinds of the substituent groups are freely settable.

As long as the sulfone compound has a structure corresponding to the structure shown in Chemical Formula 11, the sulfone compound may have any structure as a whole. However, a compound represented by Chemical Formula 12 is preferable, because the number z (the number of sulfonyl fluoride parts) is reduced, so in the electrolytic solution, high chemical stability is obtained, and superior compatibility is obtained. The compound represented by Chemical Formula 12 is a compound in which z in Chemical Formula 11 is z=2, and R1 is a divalent group.

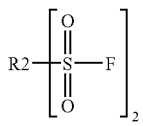

Chemical Formula 12 where R2 represents a divalent group including carbon and one kind or two or more kinds of elements selected from the group consisting of hydrogen, oxygen and halogens, a sulfur atom in a sulfonyl group is bonded to a carbon atom in R2, and in the case where R2 is a straight-chain alkylene group or a halogenated alkylene group, the number of carbon atoms is 2 or less.

Examples of R2 which is a divalent group include a straight-chain or branched alkylene group, an arylene group, a group in which an arylene group and an alkylene group are bonded together, a group in which an alkylene group and an ether bond are bonded together, a halogenated group thereof, and the like. A "divalent group including an arylene group and an alkylene group" may be a group in which one arylene group and one alkylene group are bonded together, or a group in which two alkylene groups are bonded through one arylene group. The "group in which an alkylene group and an ether bond are bonded together" means a group in which two alkylene groups are bonded through one ether bond. The "halogenated group thereof" means a group obtained by substituting a halogen for at least a part of hydrogen in the above-described alkylene group or the like. The above-described number or the bonding order of the alkylene groups, the arylene groups or the ether bonds is freely settable. R2 may be any group other than the above-described groups.

In the case where R2 is a branched alkylene group, the number of carbon atoms is freely settable. However, the number of carbon atoms is preferably within a range from 2 to 10 both inclusive, more preferably within a range from 2 to 6 both inclusive, and more preferably within a range from 2 to 4 both inclusive. Moreover, in the case where R2 is a group in which an arylene group and an alkylene group are bonded together, a group in which two alkylene groups are bonded through one arylene group is preferable. The number of carbon atoms in this case is freely settable, but the number of carbon atoms is preferably 8. It is because in any of the cases, in the electrolytic solution, high chemical stability is obtained, and superior compatibility is obtained.

In the case where R2 is a group in which an alkylene group and an ether bond are bonded together, the number of carbon atoms are freely settable, but the number of carbon atoms is preferably within a range from 2 to 12 both inclusive, more preferably within a range from 4 to 12 both inclusive. In this case, in particular, R2 is preferably a group represented by —$CH_2$—$CH_2$—O—$CH_2$—$CH_2$)$_n$—, and n is more preferably within a range from 1 to 3 both inclusive. It is because in the electrolytic solution, high chemical stability is obtained, and superior compatibility is obtained.

Specific examples of R2 include straight-chain alkylene groups (with two or less carbon atoms) represented by Chemical Formulas 13(1) and 13(2), branched alkylene groups represented by Chemical Formulas 14(1) to 14(9), arylene groups represented by Chemical Formulas 15(1) to 15(3), groups in which an arylene group and an alkylene group are bonded together represented by Chemical Formulas 16(1) to 16(3), and groups in which an alkylene group and an ether bond are bonded together represented by Chemical Formulas 17(1) to 17(13). In addition, as groups obtained by halogenating the above-described groups, as shown in Chemical Formulas 18(1) to 18(9), groups obtained by halogenating groups in which an alkylene group and an ether bond are bonded together are cited. In addition to the groups in which an alkylene group and an ether bond are bonded together, any other alkylene group or the like may be halogenated.

Chemical Formula 13

—$CH_2$— —($CH_2$)$_2$—
(1)        (2)

Chemical Formula 14

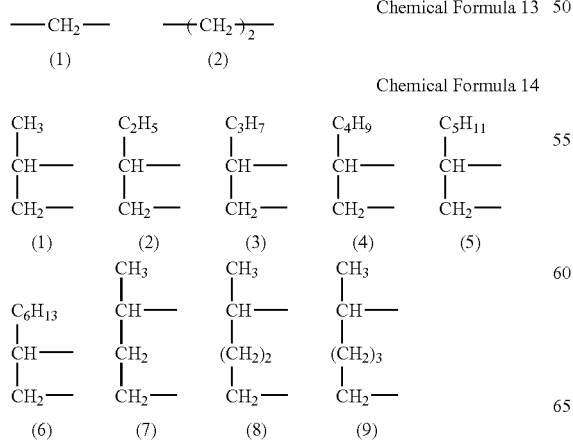

Chemical Formula 15

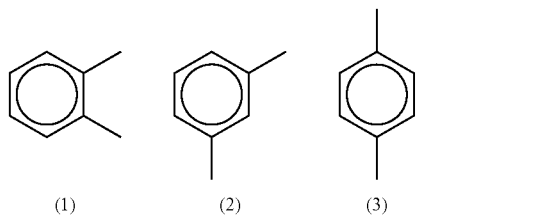

Chemical Formula 16

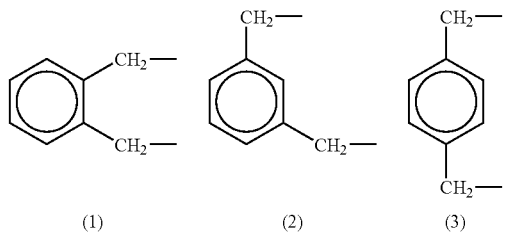

Chemical Formula 17

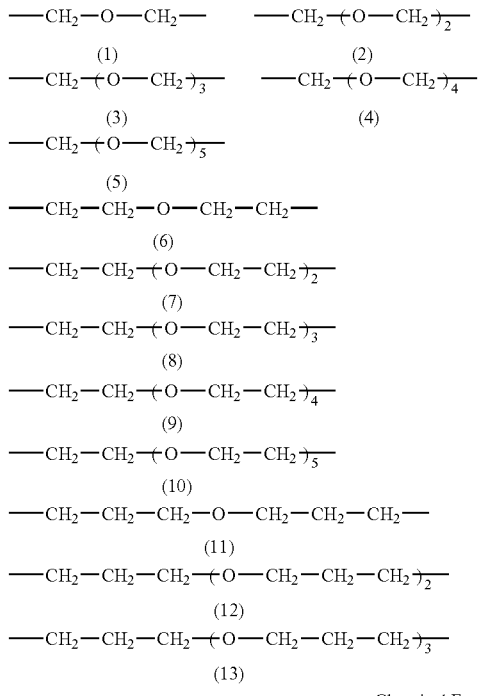

Chemical Formula 18

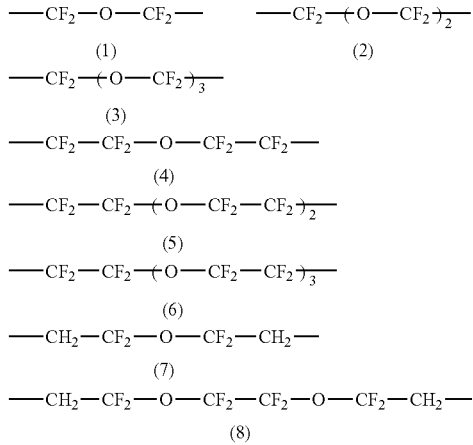

-continued

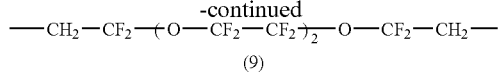

(9)

Specific examples of the compound represented by Chemical Formula 11 include compounds represented by Chemical Formulas 19(1) to 19(5). It is because in the electrolytic solution, high chemical stability is obtained, and superior solubility is obtained. For confirmation, R1 in Chemical Formula 11 is a straight-chain alkylene group in Chemical Formulas 19(1) and 19(2), a straight-chain fluorinated alkylene group in Chemical Formulas 19(3) and 19(4), and an arylene group in Chemical Formula 19(5).

Chemical Formula 19

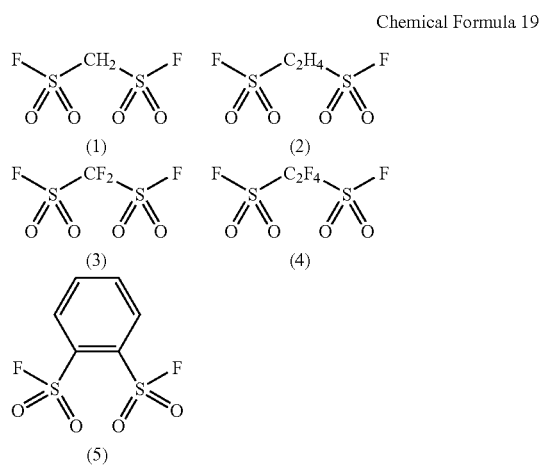

Only one kind or a mixture of a plurality of kinds selected from the compounds described as the compound represented by Chemical Formula 11 may be used. As long as the compound has the structure shown in Chemical Formula 11, the compound is not limited to the compounds represented by Chemical Formulas 12 and 19.

The content of the sulfone compound represented by Chemical Formula 11 in the solvent is freely settable. However, the content is preferably within a range from 0.01 wt % to 10 wt % both inclusive. It is because in the electrolytic solution, high chemical stability is obtained. More specifically, when the content is smaller than 0.01 wt %, there is a possibility that the chemical stability of the electrolytic solution is not obtained sufficiently and stably, and when the content is larger than 10 wt %, there is a possibility that main electrical performance of an electrochemical device (for example, capacity characteristics or the like in a secondary battery) is not obtained sufficiently.

The solvent preferably includes one kind or two or more kinds of nonaqueous solvents such as other organic solvents together with the sulfone compound represented by Chemical Formula 11. Examples of the nonaqueous solvent include ethylene carbonate, propylene carbonate, butylene carbonate, dimethyl carbonate, diethyl carbonate, ethyl methyl carbonate, methyl propyl carbonate, γ-butyrolactone, γ-valerolactone, 1,2-dimethoxyethane, tetrahydrofuran, 2-methyltetrahydrofuran, tetrahydropyran, 1,3-dioxolane, 4-methyl-1,3-dioxolane, 1,3-dioxane, 1,4-dioxane, methyl acetate, ethyl acetate, methyl propionate, ethyl propionate, methyl butyrate, methyl isobutyrate, methyl trimethylacetate, ethyl trimethylacetate, acetonitrile, glutaronitrile, adiponitrile, methoxyacetonitrile, 3-methoxypropionitrile, N,N-dimethylformamide, N-methylpyrrolidinone, N-methyloxazolidinone, N,N'-dimethyl imidazolidinone, nitromethane, nitroethane, sulfolane, trimethyl phosphate, dimethyl sulfoxide, dimethyl sulfoxide phosphate and the like. Among them, at least one kind selected from the group consisting of ethylene carbonate, propylene carbonate, dimethyl carbonate, diethyl carbonate and ethyl methyl carbonate is preferable, and a combination of a high-viscosity (high-permittivity) solvent (for example, relative permittivity $\epsilon \geq 30$) such as ethylene carbonate or propylene carbonate and a low-viscosity solvent (for example, viscosity≤1 mPa·s) such as dimethyl carbonate, ethyl methyl carbonate or diethyl carbonate is more preferable. It is because the dissociation property of the electrolyte salt and ion mobility are improved.

Moreover, the solvent may include a cyclic carbonate including an unsaturated bond, because the chemical stability of the electrolytic solution is further improved. Examples of the cyclic carbonate including an unsaturated bond include a vinylene carbonate-based compound, a vinyl ethylene carbonate-based compound and a methylene ethylene carbonate-based compound and the like.

Examples of the vinylene carbonate-based compound include vinylene carbonate (1,3-dioxol-2-one), methyl vinylene carbonate (4-methyl-1,3-dioxol-2-one), ethyl vinylene carbonate (4-ethyl-1,3-dioxol-2-one), 4,5-dimethyl-1,3-dioxol-2-one, 4,5-diethyl -1,3-dioxol-2-one, 4-fluoro-1,3-dioxol-2-one, 4-trifluoromethyl-1,3-dioxol-2-one and the like.

Examples of the vinyl ethylene carbonate-based compound include vinyl ethylene carbonate (4-vinyl-1,3-dioxolane-2-one), 4-methyl4-vinyl-1,3-dioxolane-2-one, 4-ethyl-4-vinyl-1,3-dioxolane-2-one, 4-n-propyl-4-vinyl-1, 3-dioxolane-2-one, 5-methyl4-vinyl-1,3-dioxolane-2-one, 4,4-divinyl-1,3-dioxolane-2-one, 4,5-divinyl-1,3-dioxolane-2-one and the like.

Examples of the methylene ethylene carbonate-based compound include 4-methylene-1,3-dioxolane-2-one, 4,4-dimethyl-5-methylene-1,3-dioxolane-2-one, 4,4-diethyl-5-methylene-1,3-dioxolane-2-one and the like.

Only one kind or a mixture of a plurality of kinds selected from them may be used. Among them, vinylene carbonate is preferable, because a sufficient effect is obtained.

Moreover, the solvent preferably includes at least one kind selected from the group consisting of a chain carbonate represented by Chemical Formula 20 which includes a halogen as a constituent element and a cyclic carbonate represented by Chemical Formula 21 which includes a halogen as a constituent element, because the chemical stability of the electrolytic solution is further improved.

Chemical Formula 20

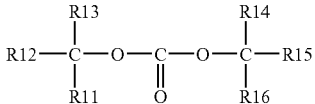

where R11, R12, R13, R14, R15 and R16 each represent a hydrogen group, a halogen group, an alkyl group or a halogenated alkyl group, and at least one of them is a halogen group or a halogenated alkyl group.

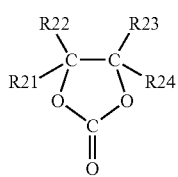

Chemical Formula 21 where R21, R22, R23 and R24 each represent a hydrogen group, a halogen group, an alkyl group or a halogenated alkyl group, and at least one of them is a halogen group or a halogenated alkyl group.

R11 to R16 in Chemical Formula 20 may be the same as or different from one another. The same holds for R21 to R24 in Chemical Formula 21. The "halogenated alkyl group" which describes R11 to R16 or R21 to R24 is a group obtained by substituting a halogen for at least a part of hydrogen in an alkyl group. The kind of the halogen is not specifically limited. However, at least one kind selected from the group consisting of fluorine, chlorine and bromine is cited, and among them, fluorine is preferable, because a high effect is obtained. Any other halogen may be used.

In particular, as a halogenated carbonate, a compound including two halogens (a dihalogenated carbonate) is preferable to a compound including one halogen (a monohalogenated carbonate), because a higher effect is obtained.

Examples of the chain carbonate represented by Chemical Formula 20 which includes a halogen include fluoromethyl methyl carbonate, bis(fluoromethyl) carbonate, difluoromethyl methyl carbonate and the like. Only one kind or a mixture of a plurality of kinds selected from them may be used. Among them, bis(fluoromethyl) carbonate is preferable, because a high effect is obtained.

In the case where at least one of R21 to R24 in Chemical Formula 21 is an alkyl group or a halogenated alkyl group, the alkyl group or the halogenated alkyl group is preferably a methyl group, an ethyl group, a halogenated methyl group or a halogenated ethyl group, because a high effect is obtained.

Examples of the cyclic carbonate represented by Chemical Formula 21 which includes a halogen include compounds represented by Chemical Formulas 22 and 23. More specifically, 4-fluoro-1,3-dioxolane-2-one in Chemical Formula 22(1), 4-chloro-1,3-dioxolane-2-one in Chemical Formula 22(2), 4,5-difluoro-1,3-dioxolane-2-one in Chemical Formula 22(3), tetrafluoro-1,3-dioxolane-2-one in Chemical Formula 22(4), 4-fluoro-5-chloro-1,3-dioxolane-2-one in Chemical Formula 22(5), 4,5-dichloro-1,3-dioxolane-2-one in Chemical Formula 22(6), tetrachloro-1,3-dioxolane-2-one in Chemical Formula 22(7), 4,5-bistrifluoromethyl-1,3-dioxolane-2-one in Chemical Formula 22(8), 4-trifluoromethyl-1,3-dioxolane-2-one in Chemical Formula 22(9), 4,5-difluoro4,5-dimethyl-1,3-dioxolane-2-one in Chemical Formula 22(10), 4-methyl-5,5-difluoro-1,3-dioxolane-2-one in Chemical Formula 22(11), and 4-ethyl-5,5-difluoro-1,3-dioxolane-2-one in Chemical Formula 22(12) are cited. Moreover, 4-trifluoromethyl-5-fluoro-1,3-dioxolane-2-one in Chemical Formula 23(1), 4-trifluoromethyl-5-methyl-1,3-dioxolane-2-one in Chemical Formula 23(2), 4-fluoro-4,5-dimethyl-1,3-dioxolane-2-one in Chemical Formula 23(3), 4,4-difluoro-5-(1,1-difluoroethyl)-1,3-dioxolane-2-one in Chemical Formula 23(4), 4,5-dichloro4,5-dimethyl-1,3-dioxolane-2-one in Chemical Formula 23(5), 4-ethyl-5-fluoro-1,3-dioxolane-2-one in Chemical Formula 23(6), 4-ethyl4,5-difluoro-1,3-dioxolane-2-one in Chemical Formula 23(7), 4-ethyl-4,5,5-trifluoro-1,3-dioxolane-2-one in Chemical Formula 23(8), and 4-fluoro-4-methyl-1,3-dioxolane-2-one in Chemical Formula 23(9) are cited.

Only one kind or a mixture of a plurality of kinds selected from them may be used. Among them, 4-fluoro-1,3-dioxolane-2-one or 4,5-difluoro-1,3-dioxolane-2-one is preferable, and 4,5-difluoro-1,3-dioxolane-2-one is preferable. It is because they are easily available, and a high effect is obtained. In particular, as 4,5-difluoro-1,3-dioxolane-2-one, a trans-isomer is more preferable than a cis-isomer.

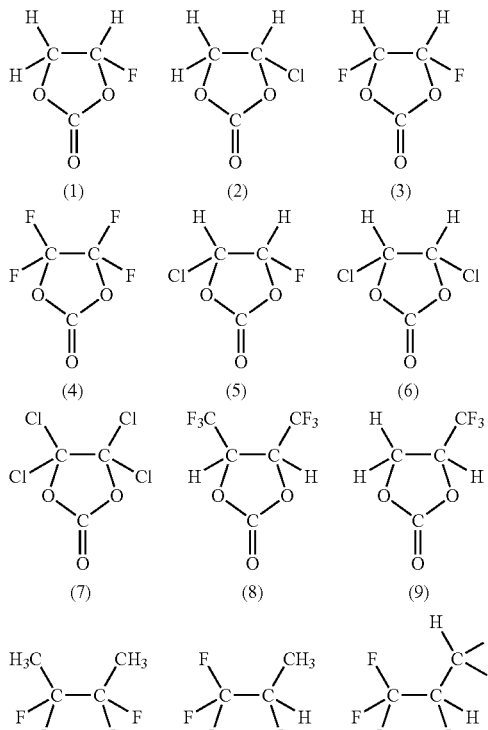

Chemical Formula 22

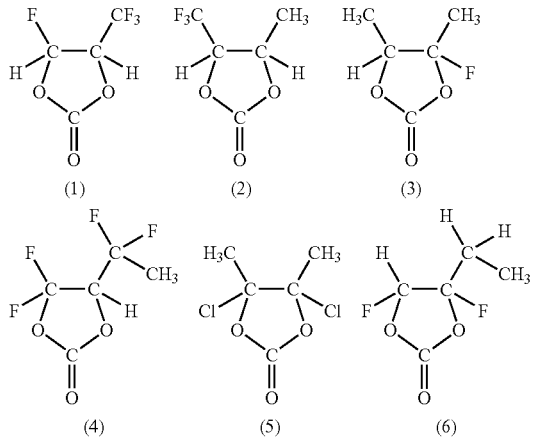

Chemical Formula 23

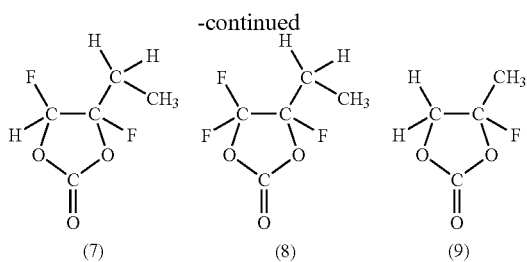

(7)        (8)        (9)

Moreover, the solvent may include a sultone (cyclic sulfonate) or an acid anhydride. It is because the chemical stability of the electrolytic solution is further improved.

Examples of the sultone include propane sultone, propene sultone and the like. Only one kind or a mixture of a plurality of kinds selected from them may be used. Among them, propene sultone is preferable. Further, the content of the sultone in the solvent is preferably within a range from 0.5 wt % to 3 wt % both inclusive. In any cases, a high effect is obtained.

Examples of the acid anhydride include a carboxylic anhydride such as succinic anhydride, glutaric anhydride or maleic anhydride, a disulfonic anhydride such as ethanedisulfonic anhydride or propanedisulfonic anhydride, an anhydride of a carboxylic acid and a sulfonic acid such as sulfobenzoic anhydride, sulfopropionic anhydride, sulfobutyric anhydride, and the like. Only one kind or a mixture of a plurality of kinds selected from them may be used. Among them, sulfobenzoic anhydride is preferable. Further, the content of the acid anhydride in the solvent is preferably within a range from 0.5 wt % to 3 wt % both inclusive. It is because in any case, a high effect is obtained.

For example, the intrinsic viscosity of the solvent is preferably 10.0 mPa·s or less at 25° C. It is because the dissociation property of the electrolyte salt and ion mobility are improved. The intrinsic viscosity in a state in which the electrolyte salt is dissolved in the solvent (that is, the intrinsic viscosity of the electrolytic solution) is also preferably 10.0 mPa·s or less at 25° C. because of the same reason.

The electrolyte salt includes one kind or two or more kinds of light metal salts such as a lithium salt. Examples of the lithium salt include lithium hexafluorophosphate, lithium tetrafluoroborate, lithium perchlorate, lithium hexafluoroarsenate, lithium tetraphenyl borate ($LiB(C_6H_5)_4$), lithium methanesulfonate ($LiCH_3SO_3$), lithium trifluoromethanesulfonate ($LiCF_3SO_3$), lithium tetrachloroaluminate ($LiAlCl_4$), lithium hexafluorosilicate ($Li_2SiF_6$), lithium chloride (LiCl), lithium bromide (LiBr) and the like. Among them, at least one kind selected from the group consisting of lithium hexafluorophosphate, lithium tetrafluoroborate, lithium perchlorate and lithium hexafluoroarsenate is preferable, and lithium hexafluorophosphate is preferable. It is because the resistance of the electrolytic solution is reduced. In particular, a combination of lithium hexafluorophosphate and lithium tetrafluoroborate is preferable. It is because a high effect is obtained.

The electrolyte salt may include at least one kind selected from the group consisting of compounds represented by Chemical Formulas 24, 25 and 26. It is because a higher effect is obtained in the case where they are used with the above-described lithium hexafluorophosphate or the like. R33 in Chemical Formula 24 may be the same as or different from each other. The same holds for R41 to R43 in Chemical Formula 25 and R51 and R52 in Chemical Formula 26.

Chemical Formula 24

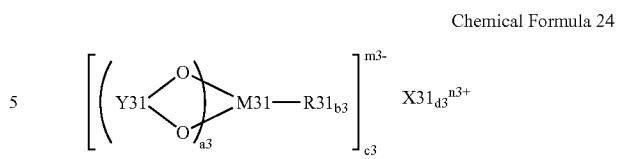

where X31 represents a Group 1A element or a Group 2A element in the short form of the periodic table of the elements, or aluminum, M31 represents a transition metal, or a Group 3B element, a Group 4B element or a Group 5B element in the short form of the periodic table of the elements, R31 represents a halogen group, Y31 represents —OC—R32-CO—, —OC—CR33$_2$- or —OC—CO—, in which R32 represents an alkylene group, a halogenated alkylene group, an arylene group or a halogenated arylene group, and R33 represents an alkyl group, a halogenated alkyl group, an aryl group or a halogenated aryl group, and a3 is an integer of 1 to 4 both inclusive, b3 is 0 or an integer of 2 or 4, and c3, d3, m3 and n3 each are an integer of 1 to 3 both inclusive.

Chemical Formula 25

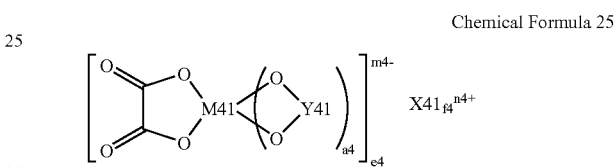

where X41 represents a Group 1A element or a Group 2A element in the short form of the periodic table of the elements, M41 represents a transition metal, or a Group 3B element, a Group 4B element or a Group 5B element in the short form of the periodic table of the elements, Y41 represents —OC—(CR41$_2$)$_{b4}$-CO—, —R43$_2$C—(CR42$_2$)$_{c4}$-CO—, —R43$_2$C—(CR42$_2$)$_{c4}$-CR43$_2$-, —R43$_2$C—(CR42$_2$)$_{c4}$-SO$_2$—, —O$_2$S—(CR42$_2$)$_{d4}$-SO$_2$— or —OC—(CR42$_2$)$_{d4}$-SO$_2$—, in which R41 and R43 each represent a hydrogen group, an alkyl group, a halogen group or a halogenated alkyl group and at least one of them is a halogen group or a halogenated alkyl group, and R42 represents a hydrogen group, an alkyl group, a halogen group or a halogenated alkyl group, and a4, e4 and n4 each are an integer of 1 or 2, b4 and d4 each are an integer of 1 to 4 both inclusive, c4 is 0 or an integer of 1 to 4 both inclusive, and f4 and m4 each are an integer of 1 to 3 both inclusive.

Chemical Formula 26

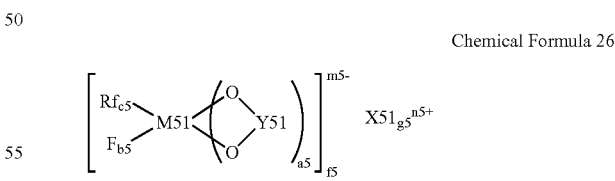

where X51 represents a Group 1A element or a Group 2A element in the short form of the periodic table of the elements, M51 represents a transition metal, or a Group 3B element, a Group 4B element or a Group 5B element in the short form of the periodic table of the elements, Rf represents a fluorinated alkyl group having 1 to 10 carbon atoms or a fluorinated aryl group having 1 to 10 carbon atoms, Y51 represents —OC—(CR51$_2$)$_{d5}$-CO—, —R52$_2$C—(CR51$_2$)$_{d5}$-CO—, —R52$_2$C—(CR51$_2$)$_{d5}$-CR52$_2$-, —R52$_2$C—(CR51$_2$)$_{d5}$-SO$_2$—, —O$_2$S—(CR51$_2$)$_{e5}$-SO$_2$— or —OC—(CR51$_2$)$_{e5}$-

SO₂—, in which R51 represents a hydrogen group, an alkyl group, a halogen group or a halogenated alkyl group, and R52 represents a hydrogen group, an alkyl group, a halogen group or a halogenated alkyl group and at least one of them is a halogen group or a halogenated alkyl group, and a5, f5 and n5 each are an integer of 1 or 2, b5, c5 and e5 each are an integer of 1 to 4 both inclusive, d5 is 0 or an integer of 1 to 4 both inclusive, and g5 and m5 each are an integer of 1 to 3 both inclusive.

Examples of the compound represented by Chemical Formula 24 include compounds represented by Chemical Formulas 27(1) to 27(6) and the like. Examples of the compound represented by Chemical Formula 25 include compounds represented by Chemical Formulas 28(1) to 28(8) and the like. Examples of the compound represented by Chemical Formula 26 include a compound represented by Chemical Formula 29 and the like. Among them, the compound represented by Chemical Formula 27(6) or Chemical Formula 28(6) is preferable, because a high effect is obtained. As long as the compound has a structure shown in Chemical Formulas 24 to 26, the compound is not limited to the compounds represented by Chemical Formulas 27 to 29.

Chemical Formula 27

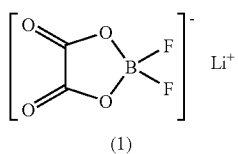

(1)

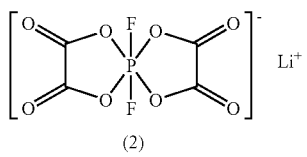

(2)

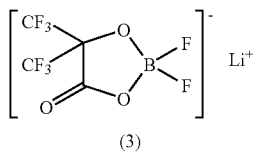

(3)

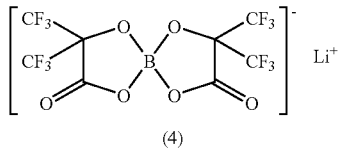

(4)

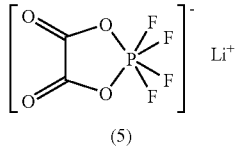

(5)

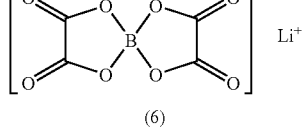

(6)

Chemical Formula 28

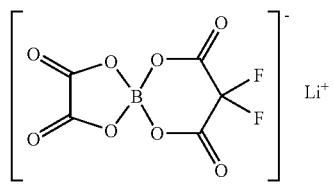

(1)

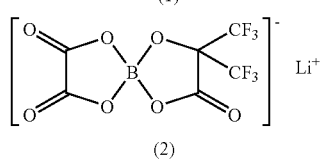

(2)

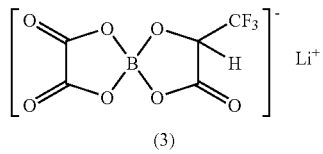

(3)

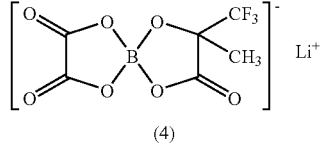

(4)

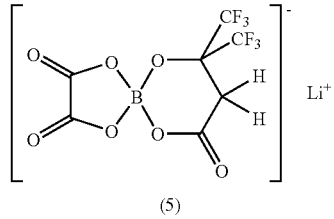

(5)

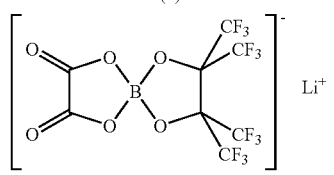

(6)

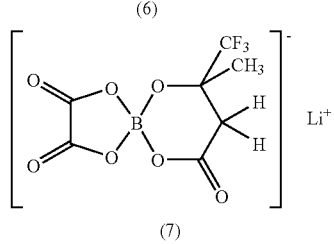

(7)

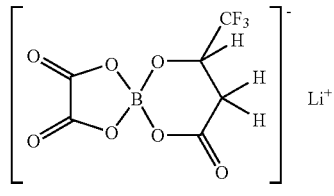

(8)

Chemical Formula 29

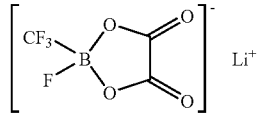

Moreover, the electrolyte salt preferably includes at least one kind selected from the group consisting of compounds represented by Chemical Formulas 30, 31 and 32, because in the case where they are used with the above-described lithium hexafluorophosphate or the like, a higher effect is obtained. In addition, m and n in Chemical Formula 30 may be the same as or different from each other. The same holds for p, q and r in Chemical Formula 32.

$$\text{LiN}(C_mF_{2m+1}SO_2)(C_nF_{2n+1}SO_2)$$ Chemical Formula 30 where m and n each are an integer of 1 or more.

Chemical Formula 31

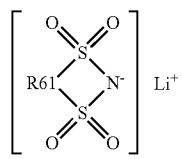

where R61 represents a straight-chain or branched perfluoroalkylene group having 2 to 4 carbon atoms.

$$\text{LiC}(C_pF_{2p+1}SO_2)(C_qF_{2q+1}SO_2)(C_rF_{2r+1}SO_2)$$ Chemical Formula 32 where p, q and r each are an integer of 1 or more.

Examples of the chain compound represented by Chemical Formula 30 include lithium bis(trifluoromethanesulfonyl)imide (LiN(CF$_3$SO$_2$)$_2$), lithium bis(pentafluoroethanesulfonyl)imide (LiN(C$_2$F$_5$SO$_2$)$_2$), lithium (trifluoromethanesulfonyl)(pentafluoroethanesulfonyl)imide (LiN(CF$_3$SO$_2$)(C$_2$F$_5$SO$_2$)), lithium (trifluoromethanesulfonyl)(heptafluoropropanesulfonyl)imide (LiN(CF$_3$SO$_2$)(C$_3$F$_7$SO$_2$)), lithium (trifluoromethanesulfonyl)(nonafluorobutanesulfonyl)imide (LiN(CF$_3$SO$_2$)(C$_4$F$_9$SO$_2$)) and the like. Only one kind or a mixture of a plurality of kinds selected from them may be used.

Examples of the cyclic compound represented by Chemical Formula 31 include compounds represented by Chemical Formula 33. More specifically, lithium 1,2-perfluoroethanedisulfonylimide in Chemical Formula 33(1), lithium 1,3-perfluoropropanedisulfonylimide in Chemical Formula 33(2), lithium 1,3-perfluorobutanedisulfonylimide in Chemical Formula 33(3), lithium 1,4-perfluorobutanedisulfonylimide in Chemical Formula 33(4) and the like are cited. Only one kind or a mixture of a plurality of kinds selected from them may be used. Among them, lithium 1,3-perfluoropropanedisulfonylimide is preferable, because a high effect is obtained.

Chemical Formula 33

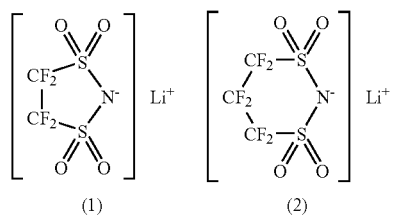

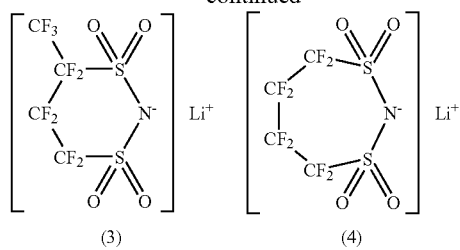

As the chain compound represented by Chemical Formula 32, for example, lithium tris(trifluoromethanesulfonyl)methide (LiC(CF$_3$SO$_2$)$_3$) or the like is cited.

The content of the electrolyte salt is preferably within a range from 0.3 mol/kg to 3.0 mol/kg both inclusive relative to the solvent. It is because when the content of the electrolyte salt is out of the range, there is a possibility that ionic conductivity is extremely reduced.

In the electrolytic solution according to the embodiment, the solvent includes the sulfone compound represented by Chemical Formula 11, so compared to the case where the sulfone compound represented by Chemical Formula 11 is not included, or the case where another sulfone compound represented by Chemical Formula 34 is included, the chemical stability is improved. The sulfone compound represented by Chemical Formula 34 is a compound having 3 carbon atoms in the case where R1 in Chemical Formula 11 is a straight-chain alkylene group. Therefore, in the case where the electrolytic solution is used in an electrochemical device such as a secondary battery, decomposition reaction is prevented, so the electrolytic solution is capable of contributing to an improvement in cycle characteristics and storage characteristics. In this case, when the sulfone compound represented by Chemical Formula 11 is the compound represented by Chemical Formula 12, or when the content of the sulfone compound represented by Chemical Formula 11 in the solvent is within a range from 0.01 wt % to 10 wt % both inclusive, a high effect is able to be obtained.

Chemical Formula 34

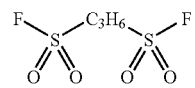

In particular, when the solvent includes the cyclic carbonate including an unsaturated bond, at least one kind selected from the group consisting of the chain carbonate represented by Chemical Formula 20 which includes a halogen and the cyclic carbonate represented by Chemical Formula 21 which includes a halogen, the sultone, or the acid anhydride, a higher effect is able to be obtained. In particular, in the case where the solvent includes at least one kind selected from the group consisting of the chain carbonate represented by Chemical Formula 20 which includes a halogen and the cyclic carbonate represented by Chemical Formula 21 which includes a halogen, when a dihalogenated carbonate rather than a monohalogenated carbonate is included, a higher effect is able to be obtained.

Further, when the electrolyte salt includes at least one kind selected from the group consisting of lithium hexafluorophosphate, lithium tetrafluoroborate, lithium perchlorate and lithium hexafluoroarsenate, at least one kind selected from the group consisting of the compounds represented by Chemical Formulas 24 to 26, or at least one kind selected from the group consisting of the compounds represented by Chemical Formulas 30 to 32, a higher effect is able to be obtained.

Next, application examples of the above-described electrolytic solution will be described below. As an example of the electrochemical device, a secondary battery is used, and the electrolytic solution is used in the secondary battery as below.

First Secondary Battery

FIG. 1 shows a sectional view of a first secondary battery. The secondary battery is, for example, a lithium-ion secondary battery in which the capacity of an anode is represented on the basis of insertion and extraction of lithium as an electrode reactant.

The secondary battery includes a spirally wound electrode body 20 which includes a cathode 21 and an anode 22 which are spirally wound with a separator 23 in between, and a pair of insulating plates 12 and 13 in a substantially hollow cylindrical-shaped battery can 11. The battery can 11 is made of, for example, a metal material such as nickel (Ni)-plated iron (Fe). An end of the battery can 11 is closed, and the other end thereof is opened. The pair of insulating plates 12 and 13 are arranged so that the spirally wound electrode body 20 is sandwiched therebetween, and the pair of insulating plates 12 and 13 extend in a direction perpendicular to a peripheral winding surface. A battery configuration using the cylindrical battery can 11 is called a cylindrical type.

In the open end of the battery can 11, a battery cover 14, and a safety valve mechanism 15 and a positive temperature coefficient device (PTC device) 16 arranged inside the battery cover 14 are mounted by caulking by a gasket 17, and the interior of the battery can 11 is sealed. The battery cover 14 is made of, for example, the same metal material as that of the battery can 11. The safety valve mechanism 15 is electrically connected to the battery cover 14 through the PTC device 16. In the safety valve mechanism 15,when an internal pressure in the battery increases to a certain extent or higher due to an internal short circuit or external application of heat, a disk plate 15A is flipped so as to disconnect the electrical connection between the battery cover 14 and the spirally wound electrode body 20. The PTC device 16 limits a current by an increase in resistance with an increase in temperature to prevent abnormal heat generation caused by a large current. The gasket 17 is made of, for example, an insulating material, and its surface is coated with asphalt.

A center pin 24 may be inserted into the center of the spirally wound electrode body 20. In the spirally wound electrode body 20, a cathode lead 25 made of a metal material such as aluminum is connected to the cathode 21, and an anode lead 26 made of a metal material such as nickel is connected to the anode 22. The cathode lead 25 is welded to the safety valve mechanism 15 so as to be electrically connected to the battery cover 14, and the anode lead 26 is welded to the battery can 11 so as to be electrically connected to the battery can 11.

Figure 2:
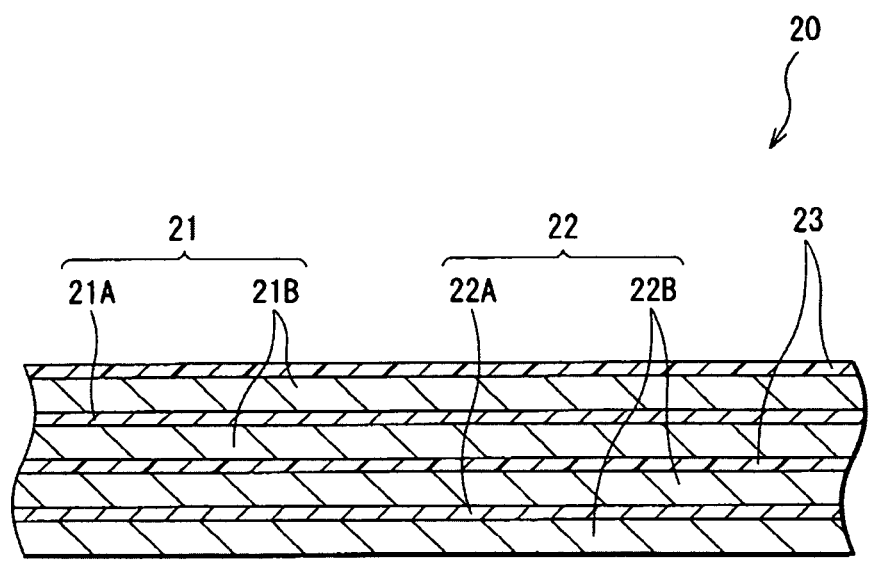
FIG. 2 is a partially enlarged sectional view of a spirally wound electrode body shown in FIG. 1.

FIG. 2 shows a partially enlarged view of the spirally wound electrode body 20 shown in FIG. 1. The cathode 21 is formed by arranging a cathode active material layer 21B on both sides of a cathode current collector 21A having a pair of surfaces. The cathode active material layer 21B may be arranged on only one side of the cathode current collector 21A.

The cathode current collector 21A is made of, for example, a metal material such as aluminum, nickel or stainless. For example, as a cathode active material, the cathode active material layer 21B includes one kind or two or more kinds of cathode materials capable of inserting and extracting lithium, and may include another material such as an electrical conductor or a binder, if necessary.

Examples of the cathode material capable of inserting and extracting lithium include chalgogenide not including lithium such as iron sulfide ($FeS_2$), titanium sulfide ($TiS_2$), molybdenum sulfide ($MoS_2$), niobium selenide ($NbSe_2$) or vanadium oxide ($V_2O_5$), and a lithium-containing compound including lithium, and the like.

Among them, the lithium-containing compound is preferable, because a high voltage and a high energy density are able to be obtained. Examples of such a lithium-containing compound include a complex oxide including lithium and a transition metal element, or a phosphate compound including lithium and a transition metal element, and in particular, a lithium-containing compound including at least one kind selected from the group consisting of cobalt, nickel, manganese and iron is preferable, because a higher voltage is obtained. The lithium-containing compound is represented by, for example, a chemical formula $Li_xM1O_2$ or $Li_yM2PO_4$. In the chemical formula, M1 and M2 represent one or more kinds of transition metal elements. The values of x and y depend on a charge-discharge state of the secondary battery, and are generally within a range of $0.05 \leq x \leq 1.10$ and $0.05 \leq y \leq 1.10$, respectively.

Examples of the complex oxide including lithium and a transition metal element include lithium-cobalt complex oxide ($Li_xCoO_2$), lithium-nickel complex oxide ($Li_xNiO_2$), lithium-nickel-cobalt complex oxide ($Li_xNi_{1-z}Co_zO_2$ (z<1)), lithium-nickel-cobalt-manganese complex oxide ($Li_xNi_{(1-v-w)}Co_vMn_wO_2$ (v+w<1), lithium-manganese complex oxide ($LiMn_2O_4$) having a spinel structure and the like. Among them, a complex oxide including nickel is preferable. It is because a high capacity is obtained, and superior cycle characteristics are obtained. Examples of the phosphate compound including lithium and a transition metal element include a lithium-iron phosphate compound ($LiFePO_4$), a lithium-iron-manganese phosphate compound ($LiFe_{1-u}Mn_uPO_4$ (u<1)) and the like.

In addition to the above-described materials, as the above-described cathode material, for example, an oxide such as titanium oxide, vanadium oxide or manganese dioxide, sulfur, or a conductive polymer such as polyaniline or polythiophene is cited.

The anode 22 is formed by arranging an anode active material layer 22B on both sides of an anode current collector 22A having a pair of surfaces. The anode active material layer 22B may be arranged on only one side of the anode current collector 22A. The anode current collector 22A is preferably made of a metal material having good electrochemical stability, electrical conductivity and mechanical strength. Examples of the metal material include copper (Cu), nickel, stainless and the like, and among them, copper is preferable, because high electrical conductivity is obtained.

The anode active material layer 22B includes one kind or two or more kinds of anode materials capable of inserting and extracting lithium as the anode active materials, and may include another material such as an electrical conductor or a binder, if necessary. The charge capacity of the anode material capable of inserting and extracting lithium is preferably larger than the charge capacity of the cathode active material.

As the anode material capable of inserting and extracting lithium, for example, a carbon material is cited. Examples of such a carbon material include graphitizable carbon, non-graphitizable carbon with a (002) plane interval of 0.37 nm or more, graphite with a (002) plane interval of 0.34 nm or more, and the like. More specifically, kinds of pyrolytic carbon, kinds of coke, kinds of graphite, glass-like carbon fibers, fired organic polymer compound bodies, carbon fibers, activated carbon kinds of carbon black and the like are cited. Among them, kinds of coke include pitch coke, needle coke, petroleum coke and so on, and the fired organic polymer compound bodies are polymers such as a phenolic resin and a furan resin which are carbonized by firing at an adequate temperature. These carbon materials are preferable, because a change in a crystal structure according to insertion and extraction of lithium is very small, so a high energy density is obtained, and superior cycle characteristics are obtained, and the carbon materials also function as electrical conductors.

As the anode material capable of inserting and extracting lithium, for example, a material being capable of inserting and extracting lithium and including at least one kind selected from the group consisting of metal elements and metalloid elements as a constituent element is cited. Such an anode material is preferable, because a high energy density is obtained. The anode material may be the simple substance, an alloy or a compound of a metal element or a metalloid element, or a material which includes a phase including one kind or two or more kinds of them at least in part. In the present application, the alloy means an alloy including two or more kinds of metal elements as well as an alloy including one or more kinds of metal elements and one or more kinds of metalloid elements. Moreover, the alloy in the present application may include a non-metal element. As the texture of the alloy, a solid solution, a eutectic (eutectic mixture), an intermetallic compound or the coexistence of two or more kinds selected from them is cited.

Examples of the metal element or the metalloid element included in the anode material include metal elements and metalloid elements which are capable of forming an alloy with lithium. More specifically, magnesium (Mg), boron (B), aluminum, gallium (Ga), indium (In), silicon (Si), germanium (Ge), tin (Sn), lead (Pb), bismuth (Bi), cadmium (Cd), silver (Ag), zinc (Zn), hafnium (Hf), zirconium (Zr), yttrium (Y), palladium (Pd), platinum (Pt) or the like is cited. Among them, at least one kind selected from the group consisting of silicon and tin is preferable, because silicon and tin have a large capability to insert and extract lithium, so a high energy density is obtained As the material including at least one kind selected from the group consisting of silicon and tin, for example, at least one kind selected from the group consisting of the simple substance, alloys and compounds of silicon and the simple substance, alloys and compounds of tin is cited. More specifically, a material including the simple substance, an alloy or a compound of silicon, the simple substance, an alloy or a compound of tin, or a material including a phase of one kind or two or more kinds selected from them at least in a part thereof is cited.

As an alloy of silicon, for example, an alloy including at least one kind selected from the group consisting of tin, nickel, copper, iron, cobalt (Co), manganese (Mn), zinc, indium, silver, titanium, germanium, bismuth, antimony (Sb) and chromium as a second constituent element in addition to silicon is cited. As an alloy of tin, for example, an alloy including at least one kind selected from the group consisting of silicon, nickel, copper, iron, cobalt, manganese, zinc, indium, silver, titanium, germanium, bismuth, antimony and chromium as a second constituent element in addition to tin is cited.

As a compound of silicon or a compound of tin, for example, a compound including oxygen or carbon is cited, and in addition to silicon or tin, the compound may include the above-described second constituent element.

In particular, as the material including at least one kind selected from the group consisting of silicon and tin as a constituent element, a material including a second constituent element and a third constituent element in addition to tin as a first constituent element is preferable. The second constituent element includes at least one kind selected from the group consisting of cobalt, iron, magnesium, titanium, vanadium (V), chromium, manganese, nickel, copper, zinc, gallium, zirconium, niobium (Nb), molybdenum (Mo), silver, indium, cerium (Ce), hafnium, tantalum (Ta), tungsten (W), bismuth and silicon. The third constituent element includes at least one kind selected from the group consisting of boron, carbon, aluminum and phosphorus. It is because when the second constituent element and the third constituent element are included, cycle characteristics are improved.

Among them, a CoSnC-containing material in which tin, cobalt and carbon are included as constituent elements, and the carbon content is within a range from 9.9 wt % to 29.7 wt % both inclusive, and the ratio of cobalt to the total of tin and cobalt (Co/(Sn+Co)) is within a range from 30 wt % to 70 wt % both inclusive is preferable, because a high energy density is obtained in such a composition range.

The CoSnC-containing material may include any other constituent element, if necessary. As the other constituent element, for example, silicon, iron, nickel, chromium, indium, niobium, germanium, titanium, molybdenum, aluminum, phosphorus, gallium, bismuth or the like is preferable, and two or more kinds selected from them may be included. It is because a higher effect is obtained.

The CoSnC-containing material includes a phase including tin, cobalt and carbon, and the phase preferably has a low crystalline structure or an amorphous structure. Moreover, in the CoSnC-containing material, at least a part of carbon as a constituent element is preferably bonded to a metal element or a metalloid element as another constituent element. It is because cohesion or crystallization of tin or the like is prevented.

As a measuring method for checking the bonding state of an element, for example, X-ray photoelectron spectroscopy (XPS) is used. In the XPS, the peak of the 1s orbit (C1s) of carbon in the case of graphite is observed at 284.5 eV in an apparatus in which energy calibration is performed so that the peak of the 4f orbit (Au4f) of a gold atom is observed at 84.0 eV. Moreover, the peak of C1s of surface contamination carbon is observed at 284.8 eV. On the other hand, in the case where the charge density of the carbon element increases, for example, in the case where carbon is bonded to a metal element or a metalloid element, the peak of C1s is observed in a region lower than 284.5 eV. In other words, in the case where the peak of the composite wave of C1s obtained in the CoSnC-containing material is observed in a region lower than 284.5 eV, at least a part of carbon included in the CoSnC-containing material is bonded to the metal element or the metalloid element which is another constituent element.

Moreover, in the XPS measurement, for example, the peak of C1s is used to correct the energy axis of a spectrum. In general, surface contamination carbon exists on a material surface, so the peak of C1s of the surface contamination carbon is fixed at 284.8 eV, and the peak is used as an energy reference. In the XPS measurement, the waveform of the peak of C1s is obtained as a form including the peak of the surface contamination carbon and the peak of carbon in the CoSnC-containing material, so the peak of the surface contamination carbon and the peak of the carbon in the CoSnC-containing material are separated by analyzing the waveform through the use of, for example, commercially available software. In the analysis of the waveform, the position of a main peak existing on a lowest binding energy side is used as an energy reference (284.8 eV).

Further, as the anode material capable of inserting and extracting lithium, for example, a metal oxide or a polymer compound capable of inserting and extracting lithium or the like is cited. As the metal oxide, for example, iron oxide, ruthenium oxide, molybdenum oxide or the like is cited, and as the polymer compound, for example, polyacetylene, polyaniline, polypyrrole or the like is cited.

A combination of the above-described anode materials capable of inserting and extracting lithium may be used.

As the electrical conductor, for example, a carbon material such as graphite, carbon black or ketjen black is cited. Only one kind or a mixture of a plurality of kinds selected from them may be used. As long as the electrical conductor is a material having electrical conductivity, any metal material or any conductive polymer may be used.

As the binder, for example, synthetic rubber such as styrene butadiene-based rubber, fluorine-based rubber or ethylene propylene diene or a polymer material such as polyvinylidene fluoride is cited. Only one kind or a mixture of a plurality of kinds selected from them may be used. However, as shown in FIG. 1, in the case where the cathode 21 and the anode 22 are spirally wound, styrene butadiene-based rubber or fluorine-based rubber which has high flexibility is preferably used.

The separator 23 isolates between the cathode 21 and the anode 22 so that lithium ions pass therethrough while preventing a short circuit of a current due to contact between the cathode 21 and the anode 22. The separator 23 is made of, for example, a porous film of a synthetic resin such as polytetrafluoroethylene, polypropylene or polyethylene, or a porous ceramic film, and the separator 23 may have a configuration in which two or more kinds of the porous films are laminated. Among them, a porous film made of polyolefin is preferable, because a short-circuit preventing effect is superior, and the safety of the secondary battery by a shutdown effect is able to be improved. In particular, polyethylene is preferable, because a shutdown effect is able to be obtained within a range from 100° C. to 160° C. both inclusive, and electrochemical stability is superior. Moreover, polypropylene is preferable, and any other resin having chemical stability such as a resin prepared by copolymerizing or blending with polyethylene or polypropylene may be used.

The separator 23 is impregnated with the above-described electrolytic solution as a liquid electrolyte, because cycle characteristics are improved.

When the secondary battery is charged, for example, lithium ions are extracted from the cathode 21, and are inserted into the anode 22 through the electrolytic solution. On the other hand, when the secondary battery is discharged, for example, lithium ions are extracted from the anode 22, and are inserted into the cathode 21 through the electrolytic solution.

The secondary battery is manufactured by the following steps, for example.

At first, for example, the cathode active material layer 21B is formed on both sides of the cathode current collector 21A to form the cathode 21. In this case, the cathode active material layer 21B is formed by the following steps. A cathode mixture formed by mixing the cathode active material, the electrical conductor and the binder is dispersed in a solvent to form paste-form cathode mixture slurry, and the cathode mixture slurry is applied to the cathode current collector 21A, and the cathode mixture slurry is dried and compression molded by a roller press, thereby the cathode active material layer 21B is formed. Moreover, for example, by the same steps as those in the case of the cathode 21, the anode 22 is formed by forming the anode active material layer 22B on the both sides of the anode current collector 22A.

Next, the cathode lead 25 is attached to the cathode current collector 21A by welding or the like, and the anode lead 26 is attached to the anode current collector 22A by welding or the like. Then, the cathode 21 and the anode 22 are spirally wound with the separator 23 in between so as to form the spirally wound electrode body 20, and an end of the cathode lead 25 is welded to the safety valve mechanism 15, and an end of the anode lead 26 is welded to the battery can 11, and then the spirally wound electrode body 20 sandwiched between the pair of insulating plates 12 and 13 is contained in the battery can 11. Next, the electrolyte salt is dissolved in the solvent including the sulfone compound represented by Chemical Formula 11 to prepare the electrolytic solution, and then the electrolytic solution is injected into the battery can 11 so as to impregnate the separator 23 with the electrolytic solution. Finally, the battery cover 14, the safety valve mechanism 15 and the PTC device 16 are fixed in an opened end portion of the battery can 11 by caulking by the gasket 17. Thereby, the secondary battery shown in FIGS. 1 and 2 is completed.

In the cylindrical type secondary battery, in the case where the capacity of the anode 22 is represented on the basis of insertion and extraction of lithium, the electrolytic solution according to the embodiment is included, so the decomposition reaction of the electrolytic solution is prevented. Therefore, the cycle characteristics and the storage characteristics are able to be improved. In particular, when the anode active material of the anode 22 includes a material being capable of inserting and extracting lithium, and including at least one kind selected from the group consisting of metal elements and metalloid elements as a constituent element, the electrolytic solution is decomposed more easily, so a higher effect than that in the case where a carbon material is included is able to be obtained. Other effects relating to the secondary battery are the same as those in the above-described electrolytic solution.

Next, second and third secondary batteries will be described below, and like components are denoted by like numerals as of the first secondary battery, and will not be further described.

Second Secondary Battery

The second secondary battery has the same configuration, functions and effects as those of the first secondary battery, except for the configuration of an anode 22 is different, and the second secondary battery is manufactured by the same steps as those in the first secondary battery.

The anode 22 has a configuration in which the anode active material layer 22B is arranged on both sides of the anode current collector 22A as in the case of the first secondary battery. As the anode active material, the anode active material layer 22B includes, for example, a material including silicon or tin as a constituent element. More specifically, for example, the anode active material includes the simple substance, an alloy or a compound of silicon, or the simple substance, an alloy or a compound of tin, and the anode active material may include two or more kinds selected from them.

The anode active material layer 22B is formed by, for example, a vapor-phase method, a liquid-phase method, a spraying method or a firing method, or a combination of two or more methods selected from them, and the anode active material layer 22B and the anode current collector 22A are preferably alloyed in at least a part of an interface therebetween. More specifically, in the interface, a constituent element of the anode current collector 22A may be diffused into the anode active material layer 22B, or a constituent element of the anode active material layer 22B may be diffused into the anode current collector 22A, or they may be diffused into each other, because a fracture of the anode active material layer 22B due to swelling and shrinkage thereof according to charge and discharge is prevented, and the electronic conductivity between the anode active material layer 22B and the anode current collector 22A is improved.

As the vapor-phase method, for example, a physical deposition method or a chemical deposition method, more specifically, a vacuum deposition method, a sputtering method, an ion plating method, a laser ablation method, a thermal CVD (chemical vapor deposition) method, a plasma chemical vapor deposition method or the like is cited. As the liquid-phase method, a known technique such as electrolytic plating or electroless plating may be used. In the firing method, for example, a particulate anode active material is mixed with a binder or the like to form a mixture, and the mixture is dispersed in a solvent and is applied, and then the mixture is heated at a higher temperature than the melting point of the binder or the like. As the firing method, a known technique such as, for example, an atmosphere firing method, a reaction firing method or a hot press firing method is cited.

Third Secondary Battery

The third secondary battery is a so-called lithium metal secondary battery in which the capacity of the anode 22 is represented on the basis of precipitation and dissolution of lithium. The secondary battery has the same configuration as that of the first secondary battery, except that the anode active material layer 22B is made of lithium metal, and the secondary battery is manufactured by the same steps as those in the first secondary battery.

The secondary battery uses lithium metal as the anode active material, thereby a higher energy density is able to be obtained. The anode active material layer 22B may exist at the time of assembling, or may not exist at the time of assembling, and may be made of lithium metal precipitated at the time of charge. Moreover, the anode active material layer 22B may be used also as a current collector, thereby the anode current collector 22A may be removed.

When the secondary battery is charged, lithium ions are extracted from the cathode 21, and the lithium ions are precipitated on the surface of the anode current collector 22A as lithium metal through the electrolytic solution. When the secondary battery is discharged, the lithium metal is dissolved from the anode active material layer 22B as lithium ions, and the lithium ions are inserted into the cathode 21 through the electrolytic solution.

In the cylindrical type secondary battery, in the case where the capacity of the anode 22 is represented on the basis of precipitation and dissolution of lithium, the electrolytic solution according to the embodiment is included, so the cycle characteristics and the storage characteristics are able to be improved. Other effects relating to the secondary battery are the same as those in the first secondary battery.

Fourth Secondary Battery

Figure 3:
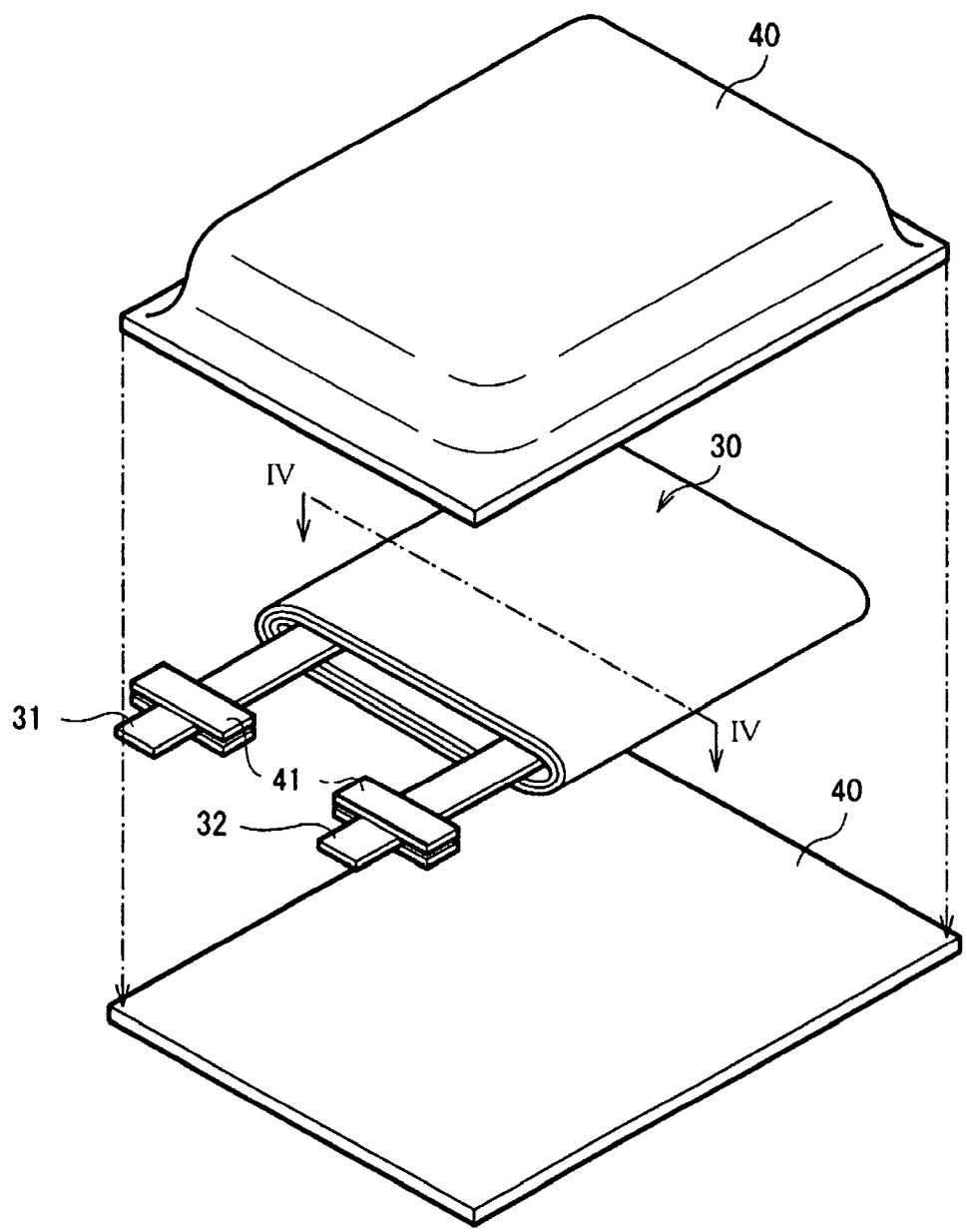
FIG. 3 is an exploded perspective view of a fourth secondary battery using the electrolytic solution according to the embodiment.

FIG. 3 shows an exploded perspective view of a fourth secondary battery. In the secondary battery, a spirally wound electrode body 30 to which a cathode lead 31 and an anode lead 32 are attached is contained in film-shaped package members 40, and a battery configuration using the film-shaped package members 40 is called a laminate film type.

The cathode lead 31 and the anode lead 32 are drawn, for example, from the interiors of the package members 40 to outside in the same direction. The cathode lead 31 is made of, for example, a metal material such as aluminum, and the anode lead 32 are made of, for example, a metal material such as copper, nickel or stainless. The metal materials of which the cathode lead 31 and the anode lead 32 are made each have a sheet shape or a mesh shape.

The package members 40 are made of, for example, a rectangular aluminum laminate film including a nylon film, aluminum foil and a polyethylene film which are bonded in this order. The package members 40 are arranged so that the polyethylene film of each of the package members 40 faces the spirally wound electrode body 30, and edge portions of the package members 40 are adhered to each other by fusion bonding or an adhesive. An adhesive film 41 is inserted between the package members 40 and the cathode lead 31 and the anode lead 32 for preventing the entry of outside air. The adhesive film 41 is made of, for example, a material having adhesion to the cathode lead 31 and the anode lead 32, for example, a polyolefin resin such as polyethylene, polypropylene, modified polyethylene or modified polypropylene.

In addition, the package members 40 may be made of a laminate film with any other configuration, a polymer film such as polypropylene or a metal film instead of the above-described three-layer aluminum laminate film.

Figure 4:
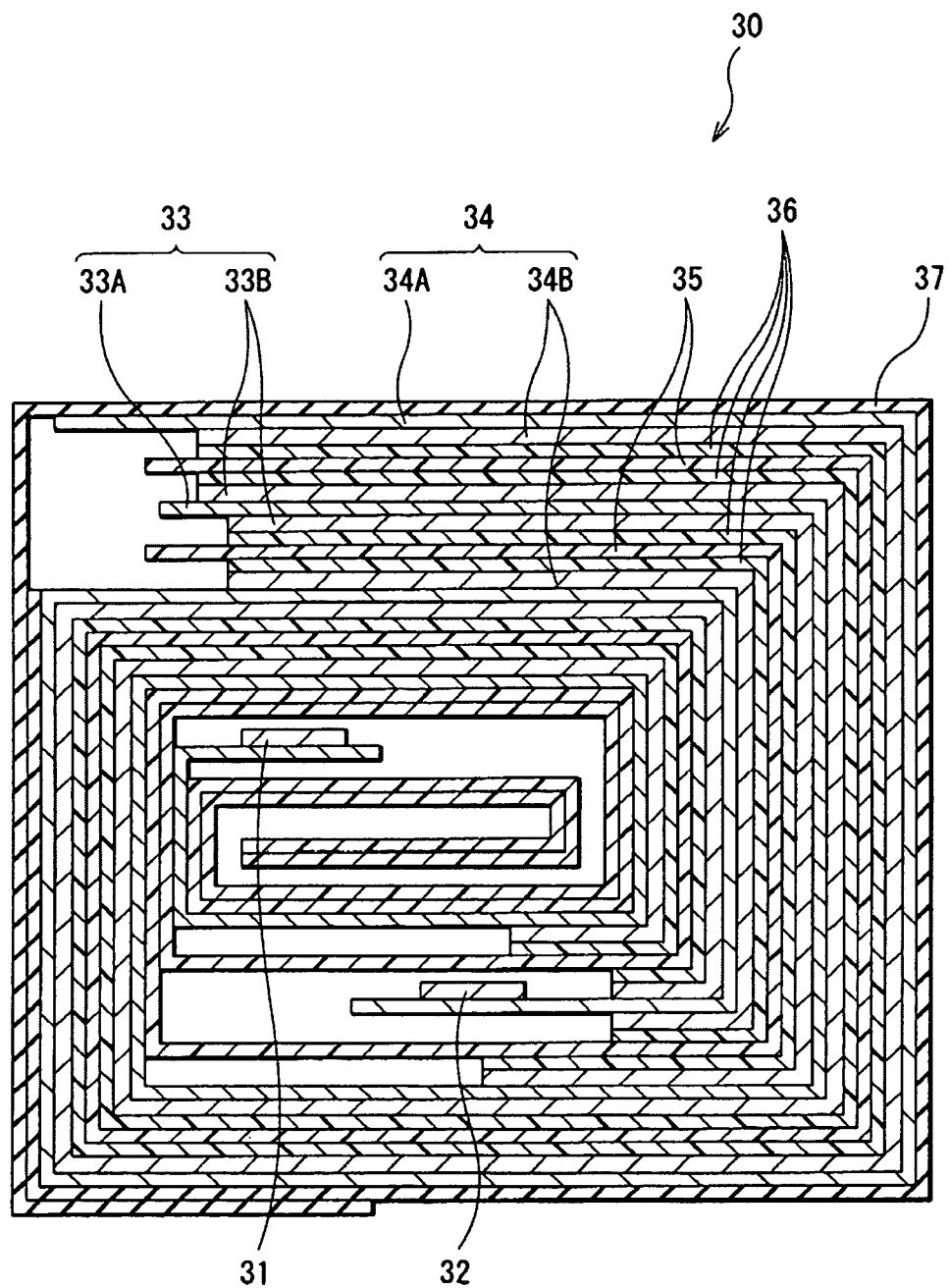
FIG. 4 is a sectional view showing a spirally wound electrode body taken along a line IV-IV of FIG. 3.

FIG. 4 shows a sectional view of the spirally wound electrode body 30 taken along a line IV-IV of FIG. 3. The spirally wound electrode body 30 is formed by laminating a cathode 33 and an anode 34 with a separator 35 and an electrolyte 36 in between, and then spirally winding them, and an outermost portion of the spirally wound electrode body 30 is protected with a protective tape 37.

The cathode 33 is formed by arranging a cathode active material layer 33B on both sides of a cathode current collector 33A. The anode 34 is formed by arranging an anode active material layer 34B on both sides of an anode current collector 34A, and the anode 34 is arranged so that the anode active material layer 34B faces the cathode active material layer 33B. The configurations of the cathode current collector 33A, the cathode active material layer 33B, the anode current collector 34A, the anode active material layer 34B and the separator 35 are the same as those of the cathode current collector 21A, the cathode active material layer 21B, the anode current collector 22A, the anode active material layer 22B and the separator 23 in the above-described first, second and third secondary batteries, respectively.

The electrolyte 36 includes the above-described electrolytic solution and a polymer compound holding the electrolytic solution, and is a so-called gel electrolyte. The gel electrolyte is preferable, because the gel electrolyte is able to obtain high ionic conductivity (for example, 1 mS/cm or over at room temperature), and leakage of an electrolyte from the secondary battery is prevented.

Examples of the polymer compound include polyacrylonitrile, polyvinylidene fluoride, a copolymer of polyvinylidene fluoride and polyhexafluoropyrene, polytetrafluoroethylene, polyhexafluoropropylene, polyethylene oxide, polypropylene oxide, polyphosphazene, polysiloxane, polyvinyl acetate, polyvinyl alcohol, polymethyl methacrylate, polyacrylic acids, polymethacrylic acids, styrene-butadiene rubber, nitrile-butadiene rubber, polystyrene, polycarbonate and the like. Only one kind or a mixture of a plurality of kinds selected from them may be used. In particular, in terms of electrochemical stability, polyacrylonitrile, polyvinylidene fluoride, polyhexafluoropropylene, polyethylene oxide or the like is preferable. The content of the polymer compound in the electrolytic solution depends on compatibility between them, but is preferably within a range from 5 wt % to 50 wt % both inclusive.

The composition of the electrolytic solution is the same as that of the electrolytic solution in the first secondary battery.

The solvent in this case has a wide concept including not only a liquid solvent but also a solvent having ionic conductivity capable of dissociating the electrolyte salt. Therefore, in the case where a polymer compound having ionic conductivity is used, the polymer compound is included in the concept of the solvent. In particular, in the case where a liquid solvent is used; propylene carbonate is preferably used, because swelling of the secondary battery is prevented.

In addition, instead of the electrolyte 36 in which the polymer compound holds the electrolytic solution, the electrolytic solution may be used as it is. In this case, the separator 35 is impregnated with the electrolytic solution.

The secondary battery may be manufactured by the following three kinds of manufacturing methods, for example.

In a first manufacturing method, by the same steps as those in the method of manufacturing the first secondary battery, at first, the cathode active material layer 33B is formed on both sides of the cathode current collector 33A so as to form the cathode 33, and the anode active material layer 34B is formed on both sides of the anode current collector 34A so as to form the anode 34. Next, the gel electrolyte 36 is formed by preparing a precursor solution including the electrolytic solution, the polymer compound and a solvent, applying the precursor solution to the cathode 33 and the anode 34, and volatilizing the solvent. Then, the cathode lead 31 and the anode lead 32 are attached to the cathode current collector 33A and the anode current collector 34A, respectively. Next, after the cathode 33 on which the electrolyte 36 is formed and the anode 34 on which the electrolyte 36 is formed are laminated with the separator 35 in between to form a laminate, the laminate is spirally wound in a longitudinal direction, and the protective tape 37 is bonded to an outermost portion of the laminate so as to form the spirally wound electrode body 30. Finally, for example, the spirally wound electrode body 30 is sandwiched between two film-shaped package members 40, and edge portions of the package members 40 are adhered to each other by thermal fusion bonding or the like to seal the spirally wound electrode body 30 in the package members 40. At this time, the adhesive film 41 is inserted between the cathode lead 31 and the anode lead 32, and the package members 40. Thereby, the secondary battery shown in FIGS. 3 and 4 is completed.

In a second manufacturing method, at first, after the cathode lead 31 and the anode lead 32 are attached to the cathode 33 and the anode 34, respectively, the cathode 33 and the anode 34 are laminated with the separator 35 in between to form a laminate, and the laminate is spirally wound, and the protective tape 37 is bonded to an outermost portion of the spirally wound laminate so as to form a spirally wound body as a precursor body of the spirally wound electrode body 30. Next, the spirally wound body is sandwiched between two film-shaped package members 40, and the edge portions of the package members 40 except for edge portions on one side are adhered by thermal fusion bonding or the like to form a pouched package, thereby the spirally wound body is contained in the package members 40. An electrolytic composition which includes the electrolytic solution, monomers as materials of a polymer compound and a polymerization initiator and, if necessary, any other material such as a polymerization inhibitor is prepared, and the composition is injected in the package members 40, and then an opened portion of the package members 40 are sealed by thermal fusion bonding or the like. Finally, the monomers are polymerized by applying heat to form the polymer compound, thereby the gel electrolyte 36 is formed. Thus, the secondary battery is completed.

In a third manufacturing method, as in the case of the first manufacturing method, the spirally wound body is formed, and the spirally wound body is contained in the package members 40, except that the separator 35 with both surfaces coated with a polymer compound is used. As the polymer compound applied to the separator 35, for example, a polymer including vinylidene fluoride as a component, that is, a homopolymer, a copolymer, a multicomponent copolymer, or the like is cited. More specifically, polyvinylidene fluoride, a binary copolymer including vinylidene fluoride and hexafluoropropylene as components, a ternary copolymer including vinylidene fluoride, hexafluoropropylene and chlorotrifluoroethylene as components is cited. The polymer compound may include one kind or two or more kinds of other polymer compounds in addition to the above-described polymer including vinylidene fluoride as a component. Next, after the electrolytic solution is prepared, and injected into the package members 40, an opened portion of the package members 40 is sealed by thermal fusion bonding or the like. Finally, the package members 40 are heated while being weighted so that the separator 35 is brought into close contact with the cathode 33 and the anode 34 with the polymer compound in between. Thereby, the polymer compound is impregnated with the electrolytic solution, and the polymer compound is gelatinized so as to form the electrolyte 36, so the secondary battery is completed.

In the third manufacturing method, compared to the first manufacturing method, swelling of the secondary battery is prevented. Moreover, in the third manufacturing method, compared to the second manufacturing method, monomers as the materials of the polymer compound, the solvent and the like hardly remain in the electrolyte 36, and a step of forming the polymer compound is controlled well, so sufficient adhesion between the cathode 33, anode 34 and the separator 35, and the electrolyte 36 is obtained.

The functions and effects of the laminate type secondary battery are the same as those in the first, second and third secondary batteries.

Second Embodiment

An electrolytic solution according to a second embodiment is used in, for example, an electrochemical device such as a secondary battery as in the case of the above-described electrolytic solution according to the first embodiment, and includes a solvent and an electrolyte salt dissolved in the solvent.

The solvent includes a sulfone compound represented by Chemical Formula 35 (hereinafter also simply referred to "sulfone compound") and at least one kind selected from the group consisting of a chain carbonate represented by Chemical Formula 36 which includes a halogen as a constituent element, and a cyclic carbonate represented by Chemical Formula 37 which includes a halogen as a constituent element (hereinafter simply and collectively called "halogenated carbonates"). It is because when a combination of the above-described sulfone compound and the halogenated carbonates is included, compared to the case where neither of them is included or the case where only one of them is included, the chemical stability of the electrolytic solution is improved.

Chemical Formula 35

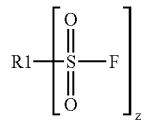

where R1 represents a z-valent group including carbon and one kind or two or more kinds of elements selected from the group consisting of hydrogen, oxygen and halogens, a sulfur atom in a sulfonyl group is bonded to a carbon atom in R1, and z is an integer of 2 or more.

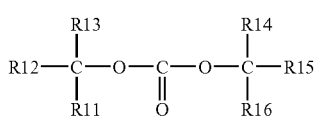

Chemical Formula 36 where R11, R12, R13, R14, R15 and R16 each represent a hydrogen group, a halogen group, an alkyl group or a halogenated alkyl group, and at least one of them is a halogen group or a halogenated alkyl group.

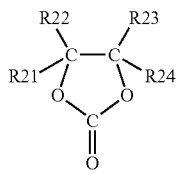

Chemical Formula 37 where R21, R22, R23 and R24 each represent a hydrogen group, a halogen group, an alkyl group or a halogenated alkyl group, and at least one of them is a halogen group or a halogenated alkyl group.

The sulfone compound represented by Chemical Formula 35 has a sulfonyl fluoride type structure in which a sulfonyl group (—SO$_2$—) and a fluorine group (—F) are bonded together. R11 to R16 in Chemical Formula 36 may be the same as or different from one another. The same holds for R21 to R24 in Chemical Formula 37.

R1 in Chemical Formula 35 is a group having a carbon chain or a carbon ring as a basic skeleton, and in the basic skeleton, one kind or two or more kinds of elements selected from the group consisting of hydrogen, oxygen and halogens may be included in any form. The carbon chain may be a straight chain or a branched chain having 1 or 2 or more side chains.

The above-described "form" means the number of elements, a combination of elements and the like, and they are freely settable. More specifically, as a form of hydrogen, for example, a part of an alkylene group or an arylene group is cited. As a form of oxygen, for example, an ether bond (—O—) or the like is cited. As a form of halogens, for example, a part of a halogenated alkylene group or the like is cited. The kind of halogen is not specifically limited, but fluorine is preferable among halogens, because compared to other halogens, the chemical stability of the electrolytic solution is improved. In the above-described form of halogens, a halogen is substituted for hydrogen in R1. In this case, the halogen may be substituted for a part of hydrogen, or all of hydrogen. The forms of hydrogen, oxygen and halogens may be any other form except for the above-described forms.

As long as R1 has the above-described structure, R1 may be any group. However, a sulfur atom in a number z of sulfonyl groups is not bonded to an atom (for example, an oxygen atom) except for a carbon atom in R1, and the sulfur atom is necessarily bonded to a carbon atom.

R1 may be a derivative of a group obtained by the above-described forms, and in this case, any other elements except for hydrogen, oxygen and halogens may be included as a constituent element. The "derivative" means a group obtained by introducing one or two or more substituent groups into the above-described groups, and the kinds of the substituent groups are freely settable.

Therefore, as long as the sulfone compound has a structure corresponding to the structure shown in Chemical Formula 35, the sulfone compound may have any structure as a whole.

Among them, as the sulfone compound, a compound represented by Chemical Formula 38 is preferable. It is because in the case where R2 is a straight-chain alkylene group or a halogenated alkylene group, the number of carbon atoms is reduced, so compared to the case where the number of carbon atoms is 3 or more, in the electrolytic solution, high chemical stability is obtained, and superior compatibility is obtained. The "halogenated alkylene group" is a group obtained by substituting a halogen for at least a part of hydrogen in an alkylene group.

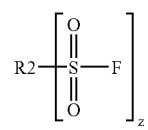

Chemical Formula 38 where R2 represents a z-valent group including carbon and one kind or two or more kinds of elements selected from the group consisting of hydrogen, oxygen and halogens, a sulfur atom in a sulfonyl group is bonded to a carbon atom in R2, z is an integer of 2 or more, and in the case where R2 is a straight-chain alkylene group or a halogenated alkylene group, the number of carbon atoms is 2 or less.

Moreover, as the sulfone compound, a compound represented by Chemical Formula 39 is preferable, because the number z (the number of sulfonyl fluoride parts) is reduced, so in the electrolytic solution, high chemical stability is obtained, and superior compatibility is obtained. The compound represented by Chemical Formula 39 is a compound in which z in Chemical Formula 35 is z=2, and R1 is a divalent group.

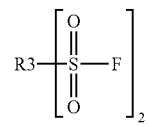

Chemical Formula 39 where R3 represents a divalent group including carbon and one kind or two or more kinds of elements selected from hydrogen, oxygen and halogens, and a sulfur atom in a sulfonyl group is bonded to a carbon atom in R3.

Examples of R3 which is a divalent group include a straight-chain or branched alkylene group, an arylene group, a group in which an arylene group and an alkylene group are bonded together, a group in which an alkylene group and an ether bond are bonded together, a halogenated group thereof and the like. A "divalent group including an arylene group and an alkylene group" may be a group in which one arylene group and one alkylene group are bonded together, or a group in which two alkylene groups are bonded through one arylene group. The "group in which an alkylene group and an ether bond are bonded together" means a group in which two alkylene groups are bonded through one ether bond. The "halogenated group thereof" means a group obtained by substituting a halogen for at least a part of hydrogen in the above-described alkylene group or the like. The above-described number or the bonding order of the alkylene groups, the arylene groups or the ether bonds is freely settable. R3 may be any other group except for the above-described groups.

In the case where R3 is a branched alkylene group, the number of carbon atoms is freely settable. However, the number of carbon atoms is preferably within a range from 2 to 10 both inclusive, more preferably within a range from 2 to 6 both inclusive, and more preferably within a range from 2 to 4 both inclusive. In particular, in the case where R,3 is a straight-chain alkylene group or a halogenated alkylene group, the number of carbon atoms is freely settable, but the number of atoms is preferably 2 or less. Moreover, in the case where R3 is a group in which an arylene group and an alkylene group are bonded together, a group in which two alkylene groups are bonded through one arylene group is preferable. The number of carbon atoms in this case is freely settable, but the number of carbon atoms is preferably 8. It is because in any of the cases, in the electrolytic solution, high chemical stability is obtained, and superior compatibility is obtained.

In the case where R3 is a group in which an alkylene group and an ether bond are bonded together, the number of carbon atoms is freely settable, but the number of carbon atoms is preferably within a range from 2 to 12 both inclusive, and more preferably within a range from 4 to 12 both inclusive. In this case, in particular, R3 is preferably a group represented by $-CH_2-CH_2-(OCH_2-CH_2)_n-$, and n is more preferably within a range from 1 to 3 both inclusive. It is because in the electrolytic solution, high chemical stability is obtained, and superior compatibility is obtained.

Specific examples of R3 include straight-chain alkylene groups represented by Chemical Formulas 40(1) to 40(7), branched alkylene groups represented by Chemical Formulas 41(1) to 41(9), arylene groups represented by Chemical Formulas 42(1) to 42(3), groups in which an arylene group and an alkylene group are bonded together represented by Chemical Formulas 43(1) to 43(3), and groups in which an alkylene group and an ether bond are bonded together represented by Chemical Formulas 44(1) to 44(13). In addition, as groups obtained by halogenating the above-described groups, as shown in Chemical Formulas 45(1) to 45(9), groups obtained by halogenating groups in which an alkylene group and an ether bond are bonded together are cited. In addition to the groups in which an alkylene group and an ether bond are bonded together, any other alkylene group or the like may be halogenated.

Chemical Formula 40

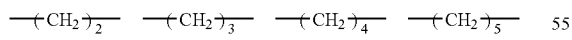

Chemical Formula 41

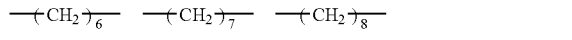

Chemical Formula 42

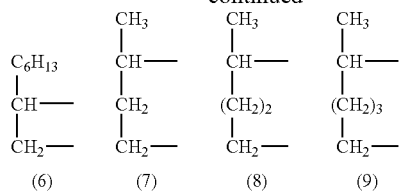

Chemical Formula 43

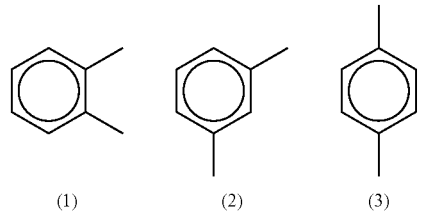

Chemical Formula 44

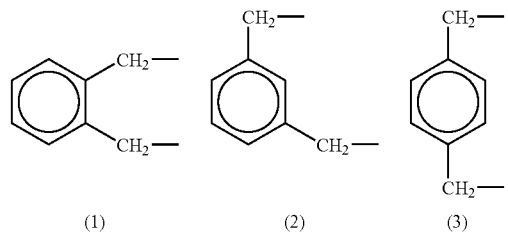

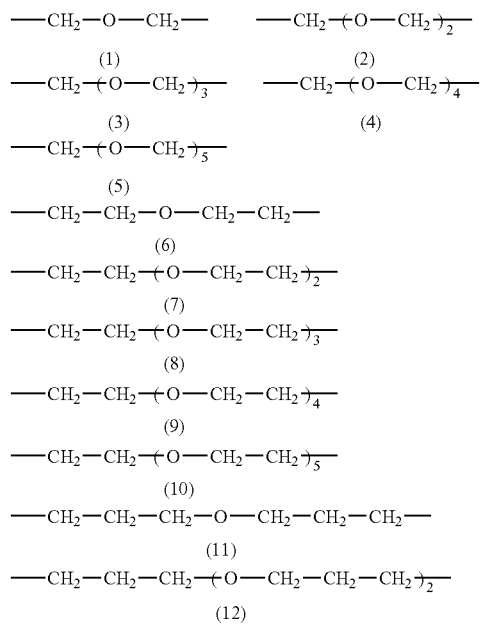

Chemical Formula 45

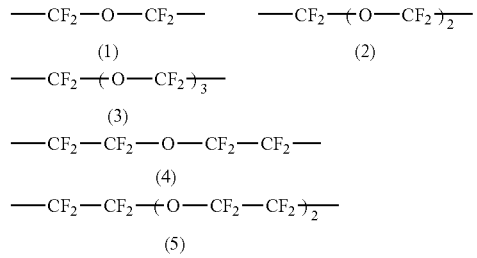

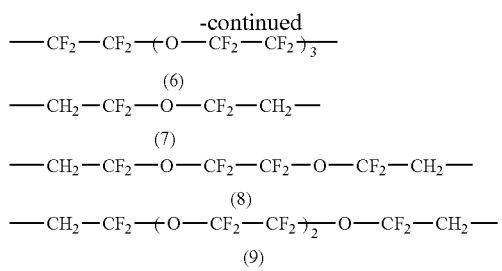

Specific examples of the compound represented by Chemical Formula 35 include compounds represented by Chemical Formulas 46(1) to 46(8). It is because in the electrolytic solution, high chemical stability is obtained, and superior solubility is obtained. For confirmation, R1 in Chemical Formula 35 is a straight-chain alkylene group in Chemical Formulas 46(1) to 46(3), a straight-chain fluorinated alkylene group in Chemical Formulas 46(4) to 46(6), an arylene group in Chemical Formula 46(7), and a group obtained by halogenating a group in which an alkylene group and an ether bond are bonded together in Chemical Formula 46(8).

Chemical Formula 46

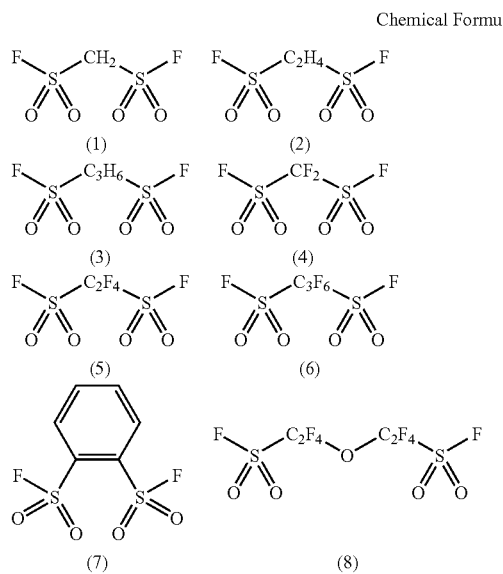

Only one kind or a mixture of a plurality of kinds selected from the compounds described as the compound represented by Chemical Formula 35 may be used. As long as the compound has a structure shown in Chemical Formula 35, the compound is not limited to the compounds represented by Chemical Formulas 38, 39 and 46.

The content of the sulfone compound represented by Chemical Formula 35 in the solvent is freely settable. However, the content is preferably within a range from 0.01 wt % to 10 wt % both inclusive. It is because in the electrolytic solution, high chemical stability is obtained. More specifically, when the content is smaller than 0.01 wt %, there is a possibility that electrochemical stability is not obtained sufficiently and stably, and when the content is larger than 10 wt %, there is a possibility that main electrical performance of an electrochemical device (for example, capacity characteristics or the like in a secondary battery) is not obtained sufficiently.

The halogenated carbonates represented by Chemical Formulas 36 and 37 are decomposed during the operation of the electrochemical device (during electrode reaction), and a halogen-based film is formed on an electrode. Thereby, the decomposition reaction of the electrolytic solution is prevented.

The "halogenated alkyl group" which describes R11 to R16 or R21 to R24 means a group obtained by substituting a halogen for at least a part of hydrogen in an alkyl group. The kind of the halogen is not specifically limited. However, at least one kind selected from the group consisting of fluorine, chlorine and bromine is cited, and among them, fluorine is preferable, because a high effect is obtained. Any other halogen may be used.

In particular, as the halogenated carbonate, a compound including two halogens (a dihalogenated carbonate) is preferable to a compound including one halogen (a monohalogenated carbonate), because a capability to form a film is improved, and a stronger and more stable film is formed, so the decomposition reaction of the electrolytic solution is further prevented.

Examples of the chain carbonate represented by Chemical Formula 36 which includes a halogen include fluoromethyl methyl carbonate, bis(fluoromethyl) carbonate, difluoromethyl methyl carbonate and the like. Only one kind or a mixture of a plurality of kinds selected from them may be used.

In the case where at least one of R21 to R24 in Chemical Formula 37 is an alkyl group or a halogenated alkyl group, a methyl group, an ethyl group, a halogenated methyl group or a halogenated ethyl group is preferable, because a high effect is obtained.

Examples of the cyclic carbonate represented by Chemical Formula 37 which includes a halogen include compounds represented by Chemical Formulas 47 and 48. More specifically, 4-fluoro-1,3-dioxolane-2-one in Chemical Formula 47(1), 4-chloro-1,3-dioxolane-2-one in Chemical Formula 47(2), 4,5-difluoro-1,3-dioxolane-2-one in Chemical Formula 47(3), tetrafluoro-1,3-dioxolane-2-one in Chemical Formula 47(4), 4-fluoro-5-chloro-1,3-dioxolane-2-one in Chemical Formula 47(5), 4,5-dichloro-1,3-dioxolane-2-one in Chemical Formula 47(6), tetrachloro-1,3-dioxolane-2-one in Chemical Formula 47(7), 4,5-bistrifluoromethyl-1,3-dioxolane-2-one in Chemical Formula 47(8), 4-trifluoromethyl-1,3-dioxolane-2-one in Chemical Formula 47(9), 4,5-difluoro-4,5-dimethyl-1,3-dioxolane-2-one in Chemical Formula 47(10), 4-methyl-5,5-difluoro-1,3-dioxolane-2-one in Chemical Formula 47(11), 4-ethyl-5,5-difluoro-1,3-dioxolane-2-one in Chemical Formula 47(12) and the like are cited. Moreover, 4-trifluoromethyl-5-fluoro-1,3-dioxolane-2-one in Chemical Formula 48(1), 4-trifluoromethyl-5-methyl-1,3-dioxolane-2-one in Chemical Formula 48(2), 4-fluoro-4,5-dimethyl-1,3-dioxolane-2-one in Chemical Formula 48(3), 4,4-difluoro-5-(1,1-difluoroethyl)-1,3-dioxolane-2-one in Chemical Formula 48(4), 4,5-dichloro4,5-dimethyl-1,3-dioxolane-2-one in Chemical Formula 48(5), 4-ethyl-5-fluoro-1,3-dioxolane-2-one in Chemical Formula 48(6), 4-ethyl4,5-difluoro-1,3-dioxolane-2-one in Chemical Formula 48(7), 4-ethyl-4,5,5-trifluoro-1,3-dioxolane-2-one in Chemical Formula 48(8), 4-fluoro-4-methyl-1,3-dioxolane-2-one in Chemical Formula 48(9) and the like are cited. Only one kind or a mixture of a plurality of kinds selected from them may be used.

Chemical Formula 47

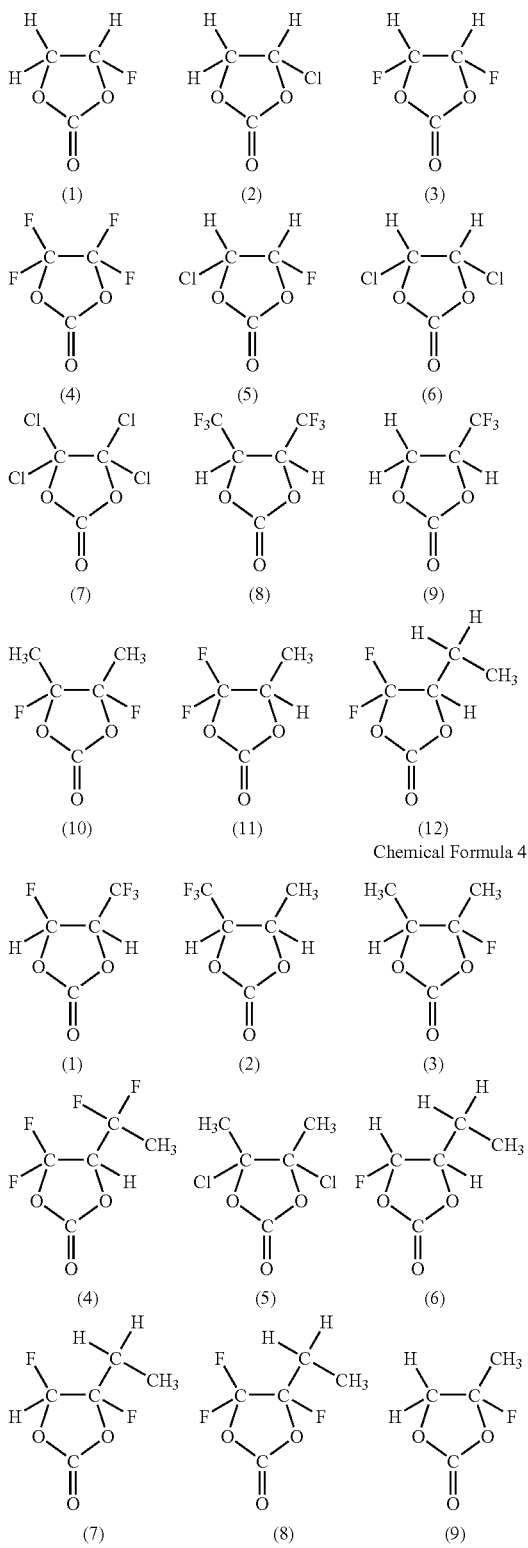

Chemical Formula 48

Among the above-described halogenated carbonates, as the monohalogenated carbonate, fluoromethyl methyl carbonate or 4-fluoro-1,-3-dioxolane-2-one is preferable, and as a dihalogenated carbonate, bis(fluoromethyl)carbonate or 4,5-difluoro-1,3-dioxolane-2-one is preferable. In particular, as 4,5-difluoro-1,3-dioxolane-2-one, a trans-isomer is preferable to a cis-isomer, because it is easily available, and a high effect is obtained.

The solvent preferably includes one kind or two or more kinds of nonaqueous solvents such as other organic solvents together with the above-described sulfone compound and the above-described halogenated carbonates. The kind, content and the like of the nonaqueous solvent are the same as those in the first embodiment.

Moreover, the solvent may include a sultone (cyclic sulfonate) or an acid anhydride. It is because the chemical stability of the electrolytic solution is further improved. The kinds and contents of the sultone and acid anhydride are the same as those in the first embodiment.

The intrinsic viscosity of the solvent is preferably 10.0 mPa·s or less at 25° C. It is because the dissociation property of the electrolyte salt and ion mobility are improved. The intrinsic viscosity in a state in which the electrolyte salt is dissolved in the solvent (that is, the intrinsic viscosity of the electrolytic solution) is also preferably 10.0 mPa·s or less at 25° C. because of the same reason.

The electrolyte salt includes one kind or two or more kinds of light metal salts such as a lithium salt. The kind, the content and the like of the lithium salt are the same as those in the first embodiment.

In the electrolytic solution according to the embodiment, the solvent includes the sulfone compound (the sulfone compound represented by Chemical Formula 35) and the halogenated carbonate (at least one kind selected from the group consisting of the chain carbonate represented by Chemical Formula 36 which includes a halogen and the cyclic carbonate represented by Chemical Formula 37 which includes a halogen), so compared to the case where neither of them is included, or only one of them is included, the chemical stability is improved. Therefore, the decomposition reaction in the case where the electrolytic solution is used in an electrochemical device such as a secondary battery is prevented, so the electrolytic solution is capable of contributing to an improvement in characteristics such as cycle characteristics, storage characteristics and swelling characteristics. In this case, when the sulfone compound is the compound represented by Chemical Formula 38 or 39, and the content of the sulfone compound in the solvent is within a range from 0.01 wt % to 10 wt % both inclusive, a high effect is able to be obtained. In particular, when the dihalogenated carbonate rather than the monohalogenated carbonate is included as the halogenated carbonate, a higher effect is able to be obtained. Other effects relating to the electrolytic solution are the same as those in the first embodiment.

The electrolytic solution according to the embodiment is applicable to the first to fourth secondary batteries described in the first embodiment. The configurations of the first to the fourth secondary batteries are the same as those in the first embodiment, except for the kind of the electrolytic solution is different.

In the first to the fourth secondary batteries, in the case where the capacity of the anode is represented on the basis of insertion and extraction of lithium, the electrolytic solution according to the embodiment is included, so the decomposition reaction of the electrolytic solution is prevented. Therefore, battery characteristics such as cycle characteristics, storage characteristics and swelling characteristics are able to be improved. In particular, when the anode active material of the anode includes a material being capable of inserting and extracting lithium and including at least one kind selected from the group consisting of metal elements and metalloid elements as a constituent element, the electrolytic solution is decomposed more easily, so a higher effect than that in the case where a carbon material is included is able to be obtained. Other effects relating to the secondary batteries are the same as those in the case where the above-described electrolytic solution is described.

Third Embodiment

An electrolytic solution according to a third embodiment is used in an electrochemical device such as a secondary battery as in the case of the first embodiment, and includes a solvent and an electrolyte salt dissolved in the solvent.

The solvent includes one kind or two or more kinds of sulfone compounds represented by Chemical Formula 49. It is because the chemical stability of the electrolytic solution is improved. The sulfone compound represented by Chemical Formula 49 has a sulfonyl fluoride type structure in which a sulfonyl group (—$SO_2$—) and a fluorine group (—F) are bonded together.

Chemical Formula 49 where R1 represents a chain group including a carbon-carbon unsaturated bond, or a derivative thereof.

R1 in Chemical Formula 49 is a group having a carbon chain which includes a carbon-carbon unsaturated bond (a carbon-carbon double bond or a carbon-carbon triple bond) as a basic skeleton. In R1, the number of carbon-carbon unsaturated bonds may be 1 or 2 or more. Moreover, the carbon-carbon unsaturated bond may be included at an end of the group or in the middle of the group. As long as R1 is a chain group, the chain group may be a straight chain or a branched chain having 1 or 2 or more side chains.

The number of carbon atoms in R1 is not specifically limited. However, the number of carbon atoms is preferably 4 or less. It is because compared to the case where the number of carbon atoms is 5 or more, superior compatibility is obtained.

For example, R1 is a group including carbon and one kind or two or more kind of elements selected from the group consisting of hydrogen, oxygen and halogens as constituent elements, and in R1, an element such as hydrogen may be included in any form. The "form" means the number of elements, a combination of elements and the like.

More specifically, as a form of hydrogen, for example, a part of an alkyl group such as a methyl group (—$CH_3$), a part of an alkylene group such as an ethylene group (—$CH_2$—), a part of a carbon-carbon double bond such as a vinyl group (—CH=$CH_2$), a part of a carbon-carbon triple bond such as a ethynyl group (—C≡CH) or the like is cited.

As a form of oxygen, for example, an ether bond (—O—), a part of a carbonyl group (—CO—) or the like is cited. In R1, the ether bond may be included at an end or in the middle.

As a form of halogens (in this case, halogens are represented by X), for example, a part of a halogenated alkyl group such as a halogenated methyl group (—$CX_3$), a part of a halogenated alkylene group such as a halogenated ethylene group (—$CX_2$—), a part of a halogenated carbon-carbon double bond such as a halogenated vinyl group (—CX=$CX_2$), a part of a halogenated carbon-carbon triple bond such as a halogenated ethynyl group (—C≡CX) or the like is cited. The kind of halogen is not specifically limited, but fluorine is preferable. It is because compared to other halogens, the chemical stability of the electrolytic solution is improved.

In the above-described form of halogens, a halogen is substituted for hydrogen in R1. In this case, the halogen may be substituted for a part of hydrogen, or all of hydrogen.

R1 may be a derivative of a group obtained by the above-described form, and in this case, any other elements except for hydrogen, oxygen and halogens may be included as a constituent element. The "derivative" means a group obtained by introducing one or two or more substituent groups into the above-described groups. The kind of the substituent group is not specifically limited. However, for example, a group (—$SO_2F$) having the same structure as that of a part except for R1 in Chemical Formula 49, or the like is cited.

Only one kind or a combination of a plurality of kinds selected from the above-described forms may be included in R1. The number of each of the forms in this case may be 1 or 2 or more. When R1 is a chain group including a carbon-carbon unsaturated bond or a derivative thereof, hydrogen, oxygen and halogens in any other forms except for the above-described forms may be included in R1.

Examples of the sulfone compound represented by Chemical Formula 49 include compounds represented by Chemical Formulas 50(1) to 50(9), Chemical Formulas 51(1) to 51(8) and Chemical Formulas 52(1) to 52(8). Among them, the compound represented by Chemical Formula 50(1), 50(7), 51(6) or 52(1) is preferable. It is because high chemical stability is obtained in the electrolytic solution. As long as the sulfone compound has a structure shown in Chemical Formula 49, the sulfone compound is not limited to the compounds represented by Chemical Formulas 50 to 52.

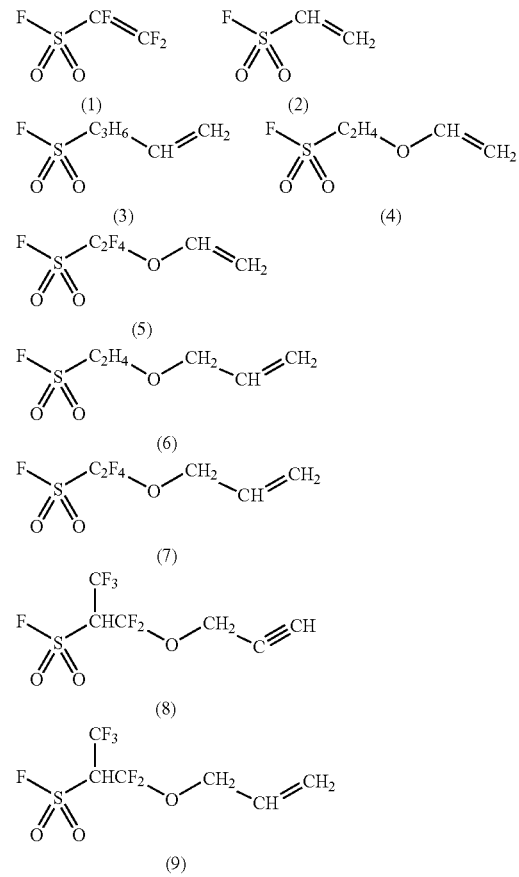

Chemical Formula 50

-continued

Chemical Formula 51

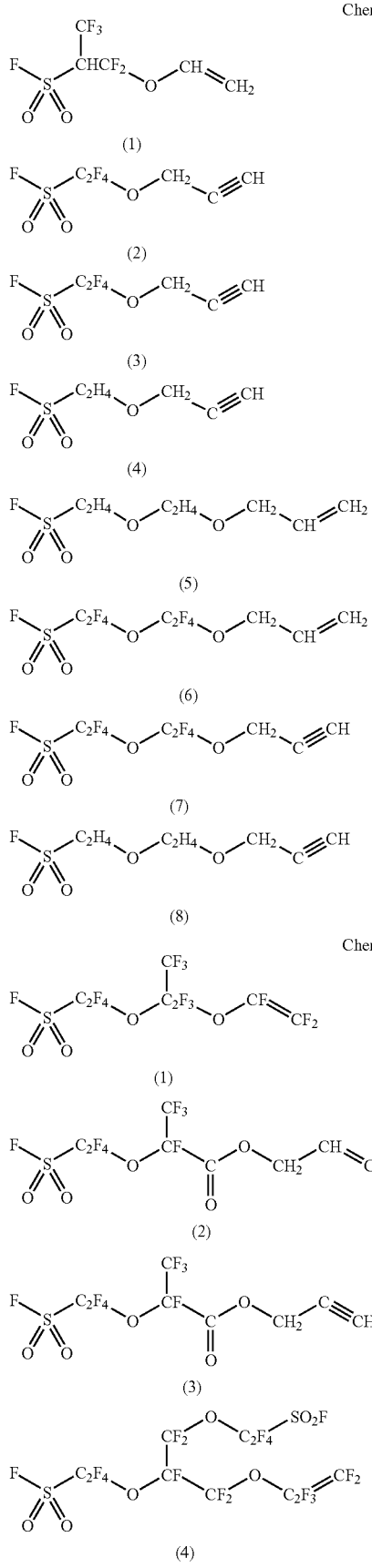

Chemical Formula 52

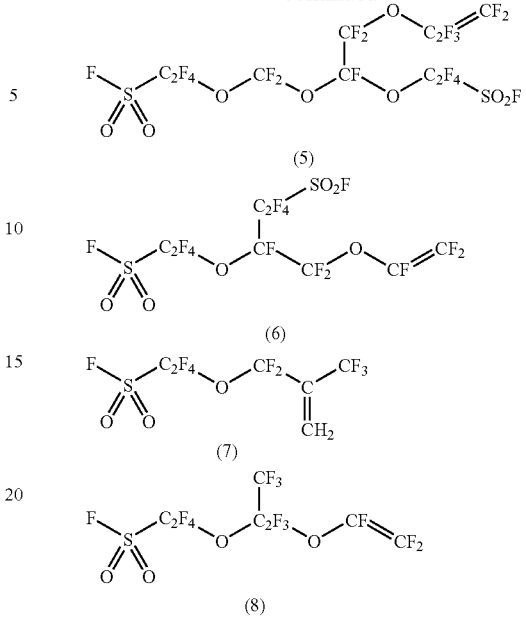

The content of the sulfone compound represented by Chemical Formula 49 in the solvent is freely settable, but is preferably within a range from 0.01 wt % to 5 wt % both inclusive. It is because high chemical stability is obtained in the electrolytic solution. More specifically, when the content is smaller than 0.01 wt %, there is a possibility that the chemical stability of the electrolytic solution is not obtained sufficiently and stably, and when the content is larger than 5 wt %, there is a possibility that main electrical performance of an electrochemical device (for example, capacity characteristics or the like in a secondary battery) is not obtained sufficiently.

The solvent preferably includes one kind or two or more kinds of nonaqueous solvents such as other organic solvents together with the sulfone compound represented by Chemical Formula 49. The kind, the content and the like of the nonaqueous solvent are the same as those in the first embodiment.

Moreover, the solvent may include a sultone (a cyclic sulfonate) or an acid anhydride, because the chemical stability of the electrolytic solution is further improved. For example, the kinds, the contents and the like of the sultone and the acid anhydride are the same as those in the first embodiment.

The intrinsic viscosity of the solvent is preferably 10.0 mPa·s or less at 25° C. It is because the dissociation property of the electrolyte salt and ion mobility are improved. The intrinsic viscosity in a state in which the electrolyte salt is dissolved in the solvent (that is, the intrinsic viscosity of the electrolytic solution) is also preferably 10.0 mPa·s or less at 25° C. because of the same reason.

The electrolyte salt includes, for example, one kind or two or more kinds of light metal salts such as a lithium salt. The kind, the content and the like of the lithium salt are the same as those in the first embodiment.

In the electrolytic solution according to the embodiment, the solvent includes the sulfone compound represented by Chemical Formula 49, so compared to the case where the sulfone compound is not included, or the case where other sulfone compounds represented by Chemical Formulas 53, 54 and 55 are included, the chemical stability is improved. The other sulfone compounds represented by Chemical Formulas 53 and 55 are compounds in which R1 in Chemical Formula 49 is a chain group not including a carbon-carbon unsaturated bond, and the other sulfone compound represented by Chemical Formula 54 is a compound in which R1 is a cyclic group including a carbon-carbon unsaturated bond. Therefore, in the case where the electrolytic solution is used in an electrochemical device, the decomposition reaction is prevented, the electrolytic solution is capable of contributing to an improvement in cycle characteristics. In this case, when the content of the sulfone compound represented by Chemical Formula 49 in the solvent is within a range from 0.01 wt % to 5 wt % both inclusive, a high effect is able to be obtained. Other effects relating to the electrolytic solution are the same as those in the first embodiment.

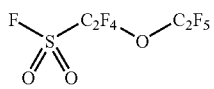

Chemical Formula 53

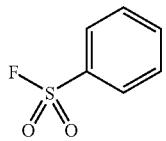

Chemical Formula 54

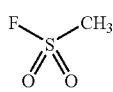

Chemical Formula 55

The electrolytic solution according to the embodiment is applicable to, for example, the first to the fourth secondary batteries described in the first embodiment. The configurations of the first to the fourth secondary batteries are the same as those in the first embodiment, except that the kind of the electrolytic solution is different.

In the first to the fourth secondary batteries, in the case where the capacity of the anode is represented on the basis of insertion and extraction of lithium, the electrolytic solution according to the embodiment is included, so the decomposition reaction of the electrolytic solution is prevented. Therefore, even if charge and discharge are repeated, a discharge capacity is less prone to being reduced, so cycle characteristics are able to be improved. In particular, when the anode active material of the anode includes a material being capable of inserting and extracting lithium, and including at least one kind selected from the group consisting of metal elements and metalloid elements as a constituent element, the electrolytic solution is decomposed more easily, so a higher effect than that in the case where a carbon material is included is obtained. Other effects relating to the secondary batteries are the same as those in the case where the above-described electrolytic solution is described.

EXAMPLES

Specific examples will be described in detail below.

At first, examples of the electrolytic solution and the secondary battery according to the first embodiment will be described below.

Example 1-1

A laminate film type secondary battery shown in FIGS. 3 and 4 was formed using artificial graphite as an anode active material. At that time, the secondary battery was a lithium-ion secondary battery in which the capacity of the anode 34 was represented on the basis of insertion and extraction of lithium.

At first, the cathode 33 was formed. After lithium carbonate ($Li_2CO_3$) and cobalt carbonate ($CoCO_3$) were mixed at a molar ratio of 0.5:1 to form a mixture, the mixture was fired in air at 900° C. for 5 hours to obtain a lithium-cobalt complex oxide ($LiCoO_2$). Next, after 91 parts by weight of the lithium-cobalt complex oxide as a cathode active material, 6 parts by weight of graphite as an electrical conductor and 3 parts by weight of polyvinylidene fluoride as a binder were mixed to form a cathode mixture, the cathode mixture was dispersed in N-methyl-2-pyrrolidone to form paste-form cathode mixture slurry. Finally, after the cathode mixture slurry was uniformly applied to both sides of the cathode current collector 33A made of strip-shaped aluminum foil (with a thickness of 20 μm), and was dried, the cathode mixture slurry was compression molded by a roller press to form the cathode active material layer 33B.

Next, the anode 34 was formed. At first, after 90 parts by weight of artificial graphite as an anode active material and 10 parts by weight of polyvinylidene fluoride as a binder were mixed to form an anode mixture, the anode mixture was dispersed in N-methyl-2-pyrrolidone to form paste-form anode mixture slurry. Finally, after the anode mixture slurry was uniformly applied to both sides of the anode current collector 34A made of strip-shaped copper foil (with a thickness of 15 μm), and was dried, the anode mixture slurry was compression molded by a roller press to form the anode active material layer 34B.

Next, the electrolytic solution was prepared. At first, after ethylene carbonate (EC) and diethyl carbonate (DEC) were mixed at a weight ratio of EC:DEC=30:70 to form a mixture, the compound represented by Chemical Formula 19(2) as the sulfone compound represented by Chemical Formula 11 (the compound represented by Chemical Formula 12) was added to and mixed with the mixture to form a solvent. At that time, the content of the compound represented by Chemical Formula 19(2) in the solvent was 0.01 wt/o. The "wt %" is a unit in the case where the whole solvent was 100 wt %, and the same holds for the following examples. Finally, as the electrolyte salt, lithium hexafluorophosphate ($LiPF_6$) was dissolved in the solvent. At that time, the concentration of the electrolyte salt in the electrolytic solution was 1 mol/kg.

Next, a secondary battery was assembled using the cathode 33 and the anode 34. At first, the cathode lead 31 made of aluminum was welded to an end of the cathode current collector 33A, and the anode lead 32 made of nickel was welded to an end of the anode current collector 34A. Next, after the cathode 33, the separator 35 (with a thickness of 25 μm) made of a microporous polypropylene film and the anode 34 were laminated in this order to form a laminate, and then the laminate was spirally wound several times in a longitudinal direction, an outermost portion of the spirally wound laminate was fixed by the protective tape 37 made of an adhesive tape so as to form a spirally wound body as a precursor body of the spirally wound electrode body 30. Next, after the spirally wound body was sandwiched between the package members 40 made of a laminate film (with a total thickness of 100 μm) with a three-layer configuration formed by laminating a nylon film (with a thickness of 30 μm), aluminum foil (with a thickness of 40 μm) and a cast polypropylene film (with a thickness of 30 μm) in order from outside, the edge portions of the package members 40 except for edge portions on one side were adhered by thermal fusion bonding to form a pouched package, thereby the spirally wound body was contained in the package members 40. Next, the electrolytic solution was injected into the package members 40 from an opened portion of the package members 40, and the separator 35 was impregnated with the electrolytic solution, thereby the spirally wound electrode body 30 was formed. Finally, the opened portion of the package members 40 were sealed by thermal fusion bonding in a vacuum atmosphere, thereby the laminate film type secondary battery was completed.

Examples 1-2 to 1-5

Secondary batteries were formed by the same steps as those in Example 1-1, except that the content of the compound represented by Chemical Formula 19(2) in the solvent was 1 wt % (Example 1-2), 2 wt % (Example 1-3), 5 wt % (Example 1-4), or 10 wt % (Example 1-5).

Examples 1-6 to 1-9

Secondary batteries were formed by the same steps as those in Example 1-2, except that instead of the compound represented by Chemical Formula 19(2), the compound represented by Chemical Formula 19(1) (Example 1-6), the compound represented by Chemical Formula 19(3) (Example 1-7), the compound represented by Chemical Formula 19(4) (Example 1-8) or the compound represented by Chemical Formula 19(5) (Example 1-9) was used.

Comparative Example 1-1

A secondary battery was formed by the same steps as those in Example 1-1, except that the compound represented by Chemical Formula 19(2) was not added.

Comparative Example 1-2

A secondary battery was formed by the same steps as those in Example 1-2, except that instead of the sulfone compound represented by Chemical Formula 11, another sulfone compound represented by Chemical Formula 34 was used.

When the cycle characteristics and the storage characteristics of the secondary batteries of Examples 1-1 to 1-9 and Comparative Examples 1-1 and 1-2 were determined, results shown in Table 1 were obtained.

To determine, the cycle characteristics, two cycles of charge and discharge were performed on each of the secondary batteries in an atmosphere at 23° C. to determine the discharge capacity in the second cycle, and then the cycle of charge and discharge was repeated until the total cycle number reached 100 cycles in the same atmosphere to determine the discharge capacity in the 100th cycle. Then, a room-temperature cycle discharge capacity retention ratio (%)= (discharge capacity in the 100th cycle/discharge capacity in the second cycle)×100 was determined by calculation. As the conditions of one cycle of charge and discharge, after each of the secondary batteries was charged at a constant current of 0.2 C and a constant voltage until reaching an upper limit voltage of 4.2 V, each of the secondary batteries was discharged at a constant current of 0.2 C until reaching a cutoff voltage of 2.7 V. In addition "0.2 C" represents a current value at which the theoretical capacity of a battery is fully discharged for 5 hours.

To determine the storage characteristics, two cycles of charge and discharge were performed on each of the secondary batteries to determine the discharge capacity, and then after each of the secondary batteries which was charged again was stored for 10 days in a constant temperature bath at 80° C., each of the secondary batteries was discharged in an atmosphere at 23° C. to determine the discharge capacity. Then, a high-temperature storage discharge capacity retention ratio (%)=(discharge capacity after storing/discharge capacity before storing)×100 was determined by calculation. The conditions of one cycle of charge and discharge were the same as those in the case where the cycle characteristics were determined.

In addition, in the following examples and the following comparative examples, the steps and the conditions when determining the cycle characteristics and the storage characteristics were the same as those described above.

TABLE 1

| | | SOLVENT | | | ROOM-TEMPERATURE CYCLE DISCHARGE CAPACITY | HIGH-TEMPERATURE STORAGE DISCHARGE CAPACITY |
|---|---|---|---|---|---|---|
| | ELECTROLYTE SALT | KIND | SULFONE COMPOUND | | RETENTION RATIO (%) | RETENTION RATIO (%) |
| | | | KIND | WT % | | |
| Anode active material: artificial graphite | | | | | | |
| EXAMPLE 1-1 | LiPF$_6$ 1 mol/kg | EC + DEC | CHEMICAL FORMULA 19(2) | 0.01 | 82 | 87 |
| EXAMPLE 1-2 | | | | 1 | 84 | 90 |
| EXAMPLE 1-3 | | | | 2 | 85 | 90 |
| EXAMPLE 1-4 | | | | 5 | 84 | 88 |
| EXAMPLE 1-5 | | | | 10 | 82 | 86 |
| EXAMPLE 1-6 | | | CHEMICAL FORMULA 19(1) | 1 | 86 | 90 |
| EXAMPLE 1-7 | | | CHEMICAL FORMULA 19(3) | 1 | 85 | 87 |
| EXAMPLE 1-8 | | | CHEMICAL FORMULA 19(4) | 1 | 83 | 88 |
| EXAMPLE 1-9 | | | CHEMICAL FORMULA 19(5) | 1 | 83 | 90 |
| COMPARATIVE EXAMPLE 1-1 | LiPF$_6$ 1 mol/kg | EC + DEC | — | — | 80 | 84 |
| COMPARATIVE EXAMPLE 1-2 | | | CHEMICAL FORMULA 34 | 1 | 81 | 84 |

As shown in Table 1, in Examples 1-1 to 1-9 in which the solvent included the sulfone compound represented by Chemical Formula 11 (the compound represented by Chemical Formula 19(1), 19(2), 19(3), 19(4) or 19(5)), a higher room-temperature cycle discharge capacity retention ratio and a higher high-temperature storage discharge capacity retention ratio than those in Comparative Examples 1-1 and 1-2 in which the sulfone compound represented by Chemical Formula 11 was not included were obtained.

More specifically, in Examples 1-1 to 1-5 in which the solvent included the compound represented by Chemical Formula 19(2), compared to Comparative Example 1-1 in which the solvent did not include the compound, the room-temperature cycle discharge capacity retention ratio and the high-temperature storage discharge capacity retention ratio were higher. In this case, when the content of the compound represented by Chemical Formula 19(2) in the solvent was within a range from 0.01 wt % to 10 wt % both inclusive, a high room-temperature cycle discharge capacity retention ratio and a high high-temperature storage discharge capacity retention ratio were obtained. When the content of the compound represented by Chemical Formula 19(2) was smaller than 0.01 wt % or larger than 10 wt %, the room-temperature cycle discharge capacity retention ratio and the high-temperature storage discharge capacity retention ratio were greatly reduced, and when the content was larger than 10 wt %, the capacity showed a tendency to be greatly reduced.

Moreover, in Examples 1-6 to 1-9 in which the solvent included the compound represented by Chemical Formula 19(1) or the like, compared to Comparative Example 1-1 in which the compound represented by Chemical Formula 19(1) or the like was not included, the room-temperature cycle discharge capacity retention ratio and the high-temperature storage discharge capacity retention ratio were higher, and a room-temperature cycle discharge capacity retention ratio and a high-temperature storage discharge capacity retention ratio which were substantially equal to those in Example 1-2 in which the compound represented by Chemical Formula 19(2) was included were obtained.

In particular, when Examples 1-2 and 1-6 in which the sulfone compound represented by Chemical Formula 11 (the compound represented by Chemical Formulas 19(1) or 19(2)) was included and Comparative Example 1-2 in which another sulfone compound represented by Chemical Formula 34 was included were compared with reference to the room-temperature cycle discharge capacity retention ratio and the high-temperature storage discharge capacity retention ratio in Comparative Example 1-1, the room-temperature cycle discharge capacity retention ratio and the high-temperature storage discharge capacity retention ratio were increased only slightly in Comparative Example 1-2. However, they were greatly increased in Examples 1-2 and 1-6. The result showed that the sulfone compound represented by Chemical Formula II and the sulfone compound represented by Chemical Formula 34 had a commonality in that R1 in Chemical Formula 11 was a straight-chain alkylene group. However, to increase the room-temperature cycle discharge capacity retention ratio and the high-temperature storage discharge capacity retention ratio, Examples 1-2 and 1-6 (the number of carbon atoms was 2 or less) had an overwhelming advantage over Comparative Example 1-2 (the number of carbon atoms was 3). This tendency was the same in the case where R1 was a straight-chain halogenated alkylene group.

Therefore, it was confirmed that in the secondary battery according to the embodiment, in the case where the anode 34 included artificial graphite as the anode active material, when the solvent of the electrolytic solution included the sulfone compound represented by Chemical Formula 11, the cycle characteristics and the storage characteristics were improved. Moreover, it was confirmed that in the case where R1 in Chemical Formula 11 was a straight-chain alkylene group or a halogenated alkylene group, the number of carbon atoms was 2 or less, so superior characteristics were obtained. In this case, it was confirmed that when the content of the compound represented by Chemical Formula 11 in the solvent was within a range from 0.01 wt % to 10 wt % both inclusive, superior characteristics were obtained, and when the content was within a range from 1 wt % to 5 wt % both inclusive, the characteristics were further improved.

Example 2-1

A secondary battery was formed by the same steps as those in Example 1-2, except that as the solvent, propylene carbonate (PC) was added. At that time, the mixture ratio of EC, DEC and PC was a weight ratio of 20:60:20.

Examples 2-2 and 2-3

Secondary batteries were formed by the same steps as those in Example 1-2, except that as the solvent, instead of DEC, ethyl methyl carbonate (EMC: Example 2-2) or dimethyl carbonate (DMC: Example 2-3) was used.

Examples 2-4 to 2-10

Secondary batteries were formed by the same steps as those in Example 1-2, except that as the solvent, vinylene carbonate (VC: Example 2-4) as the cyclic carbonate including an unsaturated bond, 4-fluoro-1,3-dioxolane-2-one (FEC: Example 2-5) as the cyclic carbonate represented by Chemical Formula 21 which included a halogen, trans-4,5-difluoro-1,3-dioxolane-2-one (t-DFEC: Example 2-6), cis-4,5-difluoro-1,3-dioxolane-2-one (c-DFEC: Example 2-7), bis(fluoromethyl) carbonate (BFDMC: Example 2-8) as the chain carbonate represented by Chemical Formula 20 which included a halogen, propene sultone (PRS: Example 2-9) as the sultone, or sulfobenzoid anhydride (SBAH: Example 2-10) as the acid anhydride was added. At that time, the content of VC or the like in the solvent was 1 wt %.

Comparative Examples 2-1 and 2-2

Secondary batteries were formed by the same steps as those in Examples 2-5 and 2-6, except that the compound represented by Chemical Formula 19(2) was not added.

When the cycle characteristics and the storage characteristics of the secondary batteries of Examples 2-1 to 2-10 and Comparative Examples 2-1 and 2-2 were determined, results shown in Table 2 were obtained.

TABLE 2

Anode active material: artificial graphite

| | ELECTROLYTE SALT | SOLVENT KIND | SULFONE COMPOUND KIND | WT % | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|
| EXAMPLE 1-2 | LiPF$_6$ | EC + DEC | CHEMICAL FORMULA 19(2) | 1 | 84 | 90 |
| EXAMPLE 2-1 | 1 mol/kg | EC + DEC + PC | | | 85 | 92 |
| EXAMPLE 2-2 | | EC + EMC | | | 83 | 91 |
| EXAMPLE 2-3 | | EC + DMC | | | 86 | 91 |
| EXAMPLE 2-4 | | EC + DEC | VC | | 87 | 90 |
| EXAMPLE 2-5 | | | FEC | | 88 | 86 |
| EXAMPLE 2-6 | | | t-DFEC | | 89 | 91 |
| EXAMPLE 2-7 | | | c-DFEC | | 90 | 90 |
| EXAMPLE 2-8 | | | BFDMC | | 88 | 91 |
| EXAMPLE 2-9 | | | PRS | | 86 | 92 |
| EXAMPLE 2-10 | | | SBAH | | 86 | 94 |
| COMPARATIVE EXAMPLE 1-1 | LiPF$_6$ 1 mol/kg | EC + DEC | — | — | 80 | 84 |
| COMPARATIVE EXAMPLE 2-1 | | | FEC | | 84 | 85 |
| COMPARATIVE EXAMPLE 2-2 | | | t-DFEC | | 85 | 85 |

As shown in Table 2, in Examples 2-1 to 2-3 in which the solvent included the compound represented by Chemical Formula 19(2) and PC or the like, the room-temperature cycle discharge capacity retention ratio and the high-temperature storage discharge capacity retention ratio were higher than those in Comparative Example 1-1 in which the compound represented by Chemical Formula 19(2) was not included, and a room-temperature cycle discharge capacity retention ratio and a high-temperature storage discharge capacity retention ratio which were substantially equal to those in Example 1-2 in which PC or the like was not included were obtained.

Moreover, in Examples 2-4 to 2-10 in which the solvent included VC or the like, the room-temperature cycle discharge capacity retention ratio was higher than that in Example 1-2 in which VC or the like was not included, and the high-temperature storage capacity retention ratio was equal to or higher than that in Example 1-2. In this case, when FEC, t-DFEC and c-DFEC were compared, there was a tendency that in the case where t-DFEC or the like as a dihalogenated carbonate was included, the room-temperature cycle discharge capacity retention ratio and the high-temperature storage discharge capacity retention ratio were higher than those in the case where FEC as a monohalogenated carbonate was included. In Examples 2-5 and 2-6 in which the solvent included the compound represented by Chemical Formula 19(2), the room-temperature cycle discharge capacity retention ratio and the high-temperature storage discharge capacity retention ratio were higher than those in Comparative Examples 2-1 and 2-2 in which the compound represented by Chemical Formula 19(2) was not included.

Therefore, it was confirmed that in the secondary battery according to the embodiment, even if the composition of the solvent was changed, the cycle characteristics and the storage characteristics were improved. It was confirmed that in this case, even in the case where propylene carbonate or the like was added to the solvent, high characteristics were obtained, and when the cyclic carbonate including an unsaturated bond, at least one kind selected from the group consisting of the chain carbonate represented by Chemical Formula 20 which included a halogen and the cyclic carbonate represented by Chemical Formula 21 which included a halogen, the sultone or the acid anhydride was added to the solvent, the characteristics were further improved.

Examples 3-1 to 3-3

Secondary batteries were formed by the same steps as those in Example 1-2, except that as the electrolyte salt, lithium tetrafluoroborate (LiBF$_4$: Example 3-1), the compound represented by Chemical Formula 27(6) as the compound represented by Chemical Formula 24 (Example 3-2), or the compound represented by Chemical Formula 28(6) as the compound represented by Chemical Formula 25 (Example 3-3) was added. At that time, the concentration of lithium hexafluorophosphate in the electrolytic solution was 0.9 mol/kg, and the concentration of lithium tetrafluoroborate or the like was 0.1 mol/kg.

When the cycle characteristics and the storage characteristics of the secondary batteries of Examples 3-1 to 3-3 were determined, results shown in Table 3 were obtained.

TABLE 3

Anode active material: artificial graphite

| | ELECTROLYTE | | SOLVENT | | | ROOM-TEMPERATURE CYCLE DISCHARGE CAPACITY RETENTION | HIGH-TEMPERATURE STORAGE DISCHARGE CAPACITY RETENTION |
|---|---|---|---|---|---|---|---|
| | SALT | | KIND | SULFONE COMPOUND | | RATIO (%) | RATIO (%) |
| | | | | KIND | WT % | | |
| EXAMPLE 1-2 | | $LiPF_6$ 1 mol/kg | EC + DEC | CHEMICAL FORMULA 19(2) | 1 | 84 | 90 |
| EXAMPLE 3-1 | $LiPF_6$ 0.9 mol/kg | $LiBF_4$ 0.1 mol/kg | | | | 86 | 92 |
| EXAMPLE 3-2 | $LiPF_6$ 0.9 mol/kg | CHEMICAL FORMULA 27(6) 0.1 mol/kg | | | | 88 | 92 |
| EXAMPLE 3-3 | $LiPF_6$ 0.9 mol/kg | CHEMICAL FORMULA 28(6) 0.1 mol/kg | | | | 86 | 91 |

As shown in Table 3, in Examples 3-1 to 3-3 in which the electrolyte salt included lithium tetrafluoroborate or the like, the room-temperature cycle discharge capacity retention ratio and the high-temperature storage discharge capacity retention ratio were higher than those in Example 1-2 in which lithium tetrafluoroborate or the like was not included.

Therefore, it was confirmed that in the secondary battery according to the embodiment, even if the kind of the electrolyte salt was changed, the cycle characteristics and the storage characteristics were improved. It was confirmed that in this case, when the electrolyte salt included lithium tetrafluoroborate, the compound represented by Chemical Formula 24, or the compound represented by Chemical Formula 25, characteristics were further improved.

The result in the case where the electrolyte salt includes at least one kind selected from the group consisting of lithium perchlorate and lithium hexafluoroarsenate, the compound represented by Chemical Formula 26, or at least one kind selected from the group consisting of the compounds represented by Chemical Formulas 30 to 32 is not shown here. However, lithium perchlorate or the like has the same functions as lithium tetrafluoroborate, so it is obvious that even in the case where lithium perchlorate or the like is included, the same effects are obtained. The same holds for the case where two or more electrolyte salts of the same kind or different kinds are mixed.

Examples 4-1 to 4-5

Secondary batteries were formed by the same steps as those in Examples 1-1 to 1-5, except that as the anode active material, instead of artificial graphite, silicon was used to form the anode active material layer 34B. In the case where the anode active material layer 34B was formed, silicon was deposited on the anode current collector 34A by an electron beam evaporation method.

Examples 4-6 to 4-9

Secondary batteries were formed by the same steps as those in Example 4-3, except that instead of the compound represented by Chemical Formula 19(2), the compound represented by Chemical Formula 19(1) (Example 4-6), the compound represented by Chemical Formula 19(3) (Example 4-7), the compound represented by Chemical Formula 19(4) (Example 4-8), or the compound represented by Chemical Formula 19(5) (example 4-9) was used.

Comparative Examples 4-1, 4-2

Secondary batteries were formed by the same steps as those in Comparative Examples 1-1 and 1-2, except that as in the case of Examples 4-1 to 4-9, as the anode active material, silicon was used to form the anode active material layer 34B.

When the cycle characteristics and the storage characteristics of the secondary batteries of Examples 4-1 to 4-9 and Comparative Examples 4-1 to 4-2 were determined, results shown in Table 4 were obtained.

TABLE 4

Anode active material: silicon

| | ELECTROLYTE | SOLVENT | | | ROOM-TEMPERATURE CYCLE DISCHARGE CAPACITY RETENTION | HIGH-TEMPERATURE STORAGE DISCHARGE CAPACITY RETENTION |
|---|---|---|---|---|---|---|
| | SALT | KIND | SULFONE COMPOUND | | RATIO (%) | RATIO (%) |
| | | | KIND | WT % | | |
| EXAMPLE 4-1 | $LiPF_6$ 1 mol/kg | EC + DEC | CHEMICAL FORMULA 19(2) | 0.01 | 44 | 78 |
| EXAMPLE 4-2 | | | | 1 | 50 | 84 |
| EXAMPLE 4-3 | | | | 2 | 55 | 85 |
| EXAMPLE 4-4 | | | | 5 | 58 | 85 |

TABLE 4-continued

Anode active material: silicon

| | ELECTROLYTE SALT | SOLVENT KIND | SULFONE COMPOUND KIND | WT % | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|
| EXAMPLE 4-5 | | | | 10 | 58 | 84 |
| EXAMPLE 4-6 | | | CHEMICAL FORMULA 19(1) | 2 | 60 | 83 |
| EXAMPLE 4-7 | | | CHEMICAL FORMULA 19(3) | 2 | 58 | 84 |
| EXAMPLE 4-8 | | | CHEMICAL FORMULA 19(4) | 2 | 54 | 84 |
| EXAMPLE 4-9 | | | CHEMICAL FORMULA 19(5) | 2 | 52 | 82 |
| COMPARATIVE EXAMPLE 4-1 | $LiPF_6$ 1 mol/kg | EC + DEC | — | — | 41 | 75 |
| COMPARATIVE EXAMPLE 4-2 | | | CHEMICAL FORMULA 34 | 1 | 43 | 80 |

As shown in Table 4, in the case where silicon was used as the anode active material, substantially the same results as those shown in Table 1 were obtained. In other words, in Examples 4-1 to 4-5 in which the solvent included the compound represented by Chemical Formula 19(2), a higher room-temperature cycle discharge capacity retention ratio and a higher high-temperature storage discharge capacity retention ratio than those in Comparative Examples 4-1 and 4-2 in which the compound represented by Chemical Formula 19(2) was not included were obtained, and in Examples 4-6 to 4-9 in which the solvent included the compound represented by Chemical Formula 19(1) or the like, a room-temperature cycle discharge capacity retention ratio and a high-temperature storage discharge capacity retention ratio which were substantially equal to those in Example 4-3 in which the compound represented by Chemical Formula 19(2) was included were obtained. In this case, when the content of the compound represented by Chemical Formula 19(2) in the solvent was within a range from 0.01 wt % to 10 wt % both inclusive, a high room-temperature cycle discharge capacity retention ratio and a high high-temperature storage discharge capacity retention ratio were obtained.

Therefore, it was confirmed that in the secondary battery according to the embodiment, in the case where the anode 34 included silicon as the anode active material, when the solvent of the electrolytic solution included the sulfone compound represented by Chemical Formula 11, the cycle characteristics and the storage characteristics were improved. It was confirmed that in this case, the content of the compound represented by Chemical Formula 11 in the solvent was within a range from 0.01 wt % to 10 wt % both inclusive, superior characteristics were obtained, and when the content was within a range from 1 wt % to 10 wt % both inclusive, the characteristics were further improved.

Example 5-1

A secondary battery was formed by the same steps as those in Example 4-3, except that as the solvent, PC was added. At that time, the mixture ratio of EC, DEC and PC was a weight ratio of 20:60:20.

Examples 5-2 and 5-3

Secondary batteries were formed by the same steps as those in Example 4-3, except that as the solvent, instead of DEC, EMC (Example 5-2) or DMC (Example 5-3) was used.

Example 5-4

A secondary battery was formed by the same steps as those in Example 4-3, except that as the solvent, instead of EC, FEC was used.

Examples 5-5 to 5-11

Secondary batteries were formed by the same steps as those in Example 4-2, except that as the solvent, VC (Example 5-5), FEC (Example 5-6), t-DFEC (Example 5-7), c-DFEC (Example 5-8), BFDMC (Example 5-9), PRS (Example 5-10), or SBAH (Example 5-11) was added. At that time, the content of VC or the like in the solvent was 5 wt %.

Comparative Examples 5-1 to 5-4

Secondary batteries were formed by the same steps as those in Examples 5-4 to 5-7, except that the compound represented by Chemical Formula 19(2) was not added.

When the cycle characteristics and the storage characteristics of the secondary batteries of Example 5-1 to 5-11 and Comparative Examples 5-1 to 5-4 were determined, results shown in Table 5 were obtained.

TABLE 5

Anode active material: silicon

| | ELECTROLYTE SALT | SOLVENT KIND | SULFONE COMPOUND KIND | WT % | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|
| EXAMPLE 4-2 | $LiPF_6$ | EC + DEC | CHEMICAL FORMULA 19(2) | 1 | 50 | 84 |
| EXAMPLE 4-3 | 1 mol/kg | | | 2 | 55 | 85 |
| EXAMPLE 5-1 | | EC + DEC + PC | | 2 | 56 | 86 |
| EXAMPLE 5-2 | | EC + EMC | | | 53 | 84 |
| EXAMPLE 5-3 | | EC + DMC | | | 54 | 84 |
| EXAMPLE 5-4 | | FEC + DEC | | | 84 | 88 |
| EXAMPLE 5-5 | | EC + VC | | 1 | 80 | 83 |
| EXAMPLE 5-6 | | DEC    FEC | | | 64 | 86 |
| EXAMPLE 5-7 | | t-DFEC | | | 85 | 89 |
| EXAMPLE 5-8 | | c-DFEC | | | 85 | 89 |
| EXAMPLE 5-9 | | BFDMC | | | 67 | 85 |
| EXAMPLE 5-10 | | PRS | | | 52 | 88 |
| EXAMPLE 5-11 | | SBAH | | | 54 | 90 |
| COMPARATIVE EXAMPLE 4-1 | $LiPF_6$ 1 mol/kg | EC + DEC | — | — | 41 | 75 |
| COMPARATIVE EXAMPLE 5-1 | | FEC + DEC | | | 78 | 75 |
| COMPARATIVE EXAMPLE 5-2 | | EC + VC DEC | | | 70 | 79 |
| COMPARATIVE EXAMPLE 5-3 | | FEC | | | 58 | 76 |
| COMPARATIVE EXAMPLE 5-4 | | t-DFEC | | | 80 | 82 |

As shown in Table 5, in the case where silicon was used as the anode active material, substantially the same results as those shown in Table 2 were obtained. In other words, in Examples 5-1 to 5-4 in which the solvent included the compound represented by Chemical Formula 19(2) and PC or the like, the room-temperature cycle discharge capacity retention ratio and the high-temperature storage discharge capacity retention ratio were higher than those in Comparative Example 4-1 in which the compound represented by Chemical Formula 19(2) was not included, and a room-temperature cycle discharge capacity retention ratio and a high-temperature discharge capacity retention ratio which were substantially equal to or higher than those in Example 4-3 in which PC or the like was not included were obtained. Moreover, in Examples 5-5 to 5-11 in which the solvent included VC or the like, the room-temperature cycle discharge capacity retention ratio was higher than that in Example 4-2 in which VC or the like was not included, and the high-temperature storage discharge capacity retention ratio was substantially equal to or higher than that in Example 4-2. In particular, there was a tendency that the room-temperature cycle discharge capacity retention ratio and the high-temperature storage discharge capacity retention ratio in the case where t-DFEC as the dihalogenated carbonate was included were higher than those in the case where FEC as the monohalogenated carbonate was included.

Therefore, it was confirmed that in the secondary battery according to the embodiment, even if the composition of the solvent was changed, the cycle characteristics and the storage characteristics were improved. It was confirmed that in this case, even in the case where the propylene carbonate or the like was added to the solvent, high characteristics were obtained, and in the case where the cyclic carbonate including an unsaturated bond, at least one kind selected from the group consisting of the chain carbonate represented by Chemical Formula 20 which included a halogen and the cyclic carbonate represented by Chemical Formula 21 which included a halogen, the sultone, or the acid anhydride was added to the solvent, the characteristics were further improved.

Examples 6-1 to 6-3

Secondary batteries were formed by the same steps as those in Example 4-3, except that as the electrolyte salt, $LiBF_4$ (Example 6-1), the compound represented by Chemical Formula 27(6) (Example 6-2), or the compound represented by Chemical Formula 28(6) (Example 6-3) was added. At that time, the concentration of lithium hexafluorophosphate in the electrolytic solution was 0.9 mol/kg, and the concentration of lithium tetrafluoroborate or the like was 0.1 mol/kg.

When the cycle characteristics and the storage characteristics of the secondary batteries of Examples 6-1 to 6-3 were determined, results shown in Table 6 were obtained.

TABLE 6

Anode active material: silicon

| | ELECTROLYTE SALT | SOLVENT KIND | SULFONE COMPOUND KIND | WT % | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|
| EXAMPLE 4-3 | LiPF$_6$ 1 mol/kg | EC + DEC | CHEMICAL FORMULA 19(2) | 2 | 55 | 85 |
| EXAMPLE 6-1 | LiPF$_6$ 0.9 mol/kg  LiBF$_1$ 0.1 mol/kg | | | | 56 | 86 |
| EXAMPLE 6-2 | LiPF$_6$ 0.9 mol/kg  CHEMICAL FORMULA 27(6) 0.1 mol/kg | | | | 58 | 88 |
| EXAMPLE 6-3 | LiPF$_6$ 0.9 mol/kg  CHEICAL FORMULA 28(6) 0.1 mol/kg | | | | 56 | 89 |

As shown in Table 6, in the case where silicon was used as the anode active material, the same results as those shown in Table 3 were obtained. In other words, in Examples 6-1 to 6-3 in which the electrolyte salt included lithium tetrafluoroborate or the like, the room-temperature cycle discharge capacity retention ratio and the high-temperature storage discharge capacity retention ratio were higher than those in Example 4-3 in which lithium tetrafluoroborate or the like was not included.

Therefore, it was confirmed that in the secondary battery according to the embodiment, even if the kind of the electrolyte salt was changed, the cycle characteristics and the storage characteristics were improved. It was confirmed that in this case, when the electrolyte salt included lithium tetrafluoroborate, the compound represented by Chemical Formula 24 or the compound represented by Chemical Formula 25, the characteristics were further improved.

It was confirmed from the above-described results shown in Tables 1 to 6 that in the secondary battery according to the embodiment, when the solvent of the electrolytic solution included the sulfone compound represented by Chemical Formula 11, irrespective of the kind of the anode active material or the composition of the solvent, the cycle characteristics and the storage characteristics were improved. It was confirmed that in this case, in the case where silicon (the material being capable of inserting and extracting lithium and including at least one kind selected from the group consisting of metal elements and metalloid elements) was used as the anode active material, the rate of increase of the discharge capacity retention ratio was larger than that in the case where the carbon material was used as the anode active material, so a higher effect was obtained in the case where silicon was used. It was considered that the result was obtained, because when silicon which was advantageous to increase the capacity was used as the anode active material, compared to the case where the carbon material was used, the electrolytic solution was easily decomposed, so the decomposition inhibition effect of the electrolytic solution was exerted pronouncedly.

Next, examples of the electrolytic solution and the secondary battery according to the second embodiment will be described below.

Example 7-1

A laminate film type secondary battery shown in FIGS. 3 and 4 was formed using artificial graphite as the anode active material. At that time, the secondary battery was a lithium-ion secondary battery in which the capacity of the anode 34 was represented on the basis of insertion and extraction of lithium.

At first, the cathode 33 and the anode 34 were formed by the same steps as those in Example 1-1.

Next, the electrolytic solution was prepared. At first, after EC and DEC were mixed at a weight ratio of EC:DEC=30:70 to form a mixture, FEC as the halogenated carbonate (the cyclic carbonate represented by Chemical Formula 37 which included a halogen) and the compound represented by Chemical Formula 46(2) as the sulfone compound (the compound represented by Chemical Formula 35) were added to and mixed with the mixture to form a solvent. At that time, the content of FEC in the solvent was 1 wt %, and the content of the compound represented by Chemical Formula 46(2) in the solvent was 0.01 wt %. The "wt %" is a unit in the case where the whole solvent was 100 wt %, and the same holds for the following examples. Finally, as the electrolyte salt, lithium hexafluorophosphate (LiPF$_6$) was dissolved in the solvent. At that time, the concentration of the electrolyte salt in the electrolytic solution was 1 mol/kg.

Next, the laminate film type secondary battery was formed using the cathode 33 and the anode 34 by the same steps as those in Example 1-1.

Examples 7-2 to 7-5

Secondary batteries were formed by the same steps as those in Examples 7-1, except that the content of the compound represented by Chemical Formula 46(2) in the solvent was 1 wt % (Example 7-2), 2 wto/o (Example 7-3), 5 wt % (Example 7-4) or 10 wt % (Example 7-5).

Examples 7-6 to 7-12

Secondary batteries were formed by the same steps as those in Example 7-2, except that instead of the compound represented by Chemical Formula 46(2), the compound represented by Chemical Formula 46(1) (Example 7-6), the compound represented by Chemical Formula 46(3) (Example 7-7), the compound represented by Chemical Formula 46(4)

(Example 7-8), the compound represented by Chemical Formula 46(5) (Example 7-9), the compound represented by Chemical Formula 46(6) (Example 7-10), the compound represented by Chemical Formula 46(7) (Example 7-11), or the compound represented by Chemical Formula 46(8) (Example 7-12) was used.

Comparative Example 7-1

A secondary battery was formed by the same steps as those in Example 7-1, except that FEC and the compound represented by Chemical Formula 46(2) were not included.

Comparative Example 7-2

A secondary battery was formed by the same steps as those in Example 7-1, except that the compound represented by Chemical Formula 46(2) was not included.

Comparative Example 7-3

A secondary battery was formed by the same steps as those in Example 7-2, except that FEC was not included.

Comparative Examples 7-4 and 7-5

Secondary batteries were formed by the same steps as those in Comparative Examples 7-1 and 7-3, except that as the solvent, VC was added. At that time, the content of VC in the solvent was 1 wt %.

When the cycle characteristics, the storage characteristics and the swelling characteristics of the secondary batteries of Examples 7-1 to 7-12 and Comparative Examples 7-1 to 7-5 were determined, results shown in Table 7 were obtained.

To determine the swelling characteristics, after two cycles of charge and discharge were performed on each of the secondary batteries in an atmosphere at 23° C., each of the secondary batteries was charged again, and the thickness of each of the secondary batteries was determined. Then, after each of the secondary batteries which was still in a charged state was stored for 4 hours in a constant temperature bath at 90° C., the thickness of each of the secondary batteries was determined. Then, swelling (mm)=(thickness after storage−thickness before storage) was determined by calculation.

In addition, in the following examples and the following comparative examples, the steps and the conditions when determining the cycle characteristics and the storage characteristics were the same as those described above.

TABLE 7

Anode active material: artificial graphite

| | | SOLVENT | | | | ROOM-TEMPERATURE CYCLE DISCHARGE CAPACITY RETENTION | HIGH-TEMPERATURE STORAGE DISCHARGE CAPACITY RETENTION | |
|---|---|---|---|---|---|---|---|---|
| | ELECTROLYTE | | HALOGENATED | SULFONE COMPOUND | | RATIO | RATIO | SWELLING |
| | SALT | KIND | CARBONATE | KIND | WT % | (%) | (%) | (mm) |
| EXAMPLE 7-1 | $LiPF_6$ | EC + | FEC | CHEMICAL FORMULA 46(2) | 0.01 | 86 | 87 | — |
| EXAMPLE 7-2 | 1 mol/kg | DEC | | FORMULA 46(2) | 1 | 90 | 90 | 0.321 |
| EXAMPLE 7-3 | | | | | 2 | 86 | 90 | — |
| EXAMPLE 7-4 | | | | | 5 | 84 | 88 | — |
| EXAMPLE 7-5 | | | | | 10 | 82 | 86 | — |
| EXAMPLE 7-6 | | | | CHEMICAL FORMULA 46(1) | 1 | 89 | 90 | — |
| EXAMPLE 7-7 | | | | CHEMICAL FORMULA 46(3) | 1 | 86 | 87 | — |
| EXAMPLE 7-8 | | | | CHEMICAL FORMULA 46(4) | 1 | 91 | 90 | — |
| EXAMPLE 7-9 | | | | CHEMICAL FORMULA 46(5) | 1 | 91 | 90 | — |
| EXAMPLE 7-10 | | | | CHEMICAL FORMULA 46(6) | 1 | 86 | 88 | — |
| EXAMPLE 7-11 | | | | CHEMICAL FORMULA 46(7) | 1 | 85 | 90 | — |
| EXAMPLE 7-12 | | | | CHEMICAL FORMULA 46(8) | 1 | 85 | 90 | — |
| COMPARATIVE EXAMPLE 7-1 | $LiPF_6$ 1 mol/kg | EC + DEC | — | — | — | 80 | 84 | 0.248 |
| COMPARATIVE EXAMPLE 7-2 | | | FEC | — | — | 84 | 85 | 0.500 |
| COMPARATIVE EXAMPLE 7-3 | | | — | CHEMICAL FORMULA 46(2) | 1 | 82 | 86 | — |
| COMPARATIVE EXAMPLE 7-4 | | EC + DEC + VC | — | — | — | 84 | 85 | — |
| COMPARATIVE EXAMPLE 7-5 | | | — | CHEMICAL FORMULA 46(2) | 1 | 85 | 86 | — |

As shown in Table 7, in Examples 7-1 to 7-12 in which the solvent included FEC and the compounds represented by Chemical Formulas 46(1) to 46(8), compared to Comparative Examples 7-1 to 7-5 in which neither of them was included, or only one of them was included, a substantially equal or higher room-temperature cycle discharge capacity retention ratio and a substantially equal or higher high-temperature storage discharge capacity retention ratio were obtained.

More specifically, in Examples 7-1 to 7-5 in which the solvent included FEC and the compound represented by Chemical Formula 46(2), the room-temperature cycle discharge capacity retention ratio and the high-temperature storage discharge capacity retention ratio were higher than those in Comparative Example 7-1 in which neither of them was included. In this case, when the content of the compound represented by Chemical Formula 46(2) in the solvent was within a range from 0.01 wt % to 10 wt % both inclusive, a high room-temperature cycle discharge capacity retention ratio and a high high-temperature storage discharge capacity retention ratio were obtained. When the content of the compound represented by Chemical Formula 46(2) was smaller than 0.01 wt % or larger than 10 wt %, the room-temperature cycle discharge capacity retention ratio and the high-temperature storage discharge capacity retention ratio were greatly reduced, and when the content was larger than 10 wt %, the capacity showed a tendency to be greatly reduced. In Examples 7-6 to 7-12 in which the solvent included the compound represented by Chemical Formula 46(1) or the like, the results were the same as those described in Examples 7-1 to 7-5.

Moreover, in Examples 7-1 to 7-5, the room-temperature cycle discharge capacity retention ratio was substantially equal to or higher than that in Comparative Example 7-2 in which the solvent included only FEC. However, the high-temperature storage discharge capacity retention ratio was higher than that in Comparative Example 7-2. In this case, when the content of the compound represented by Chemical Formula 46(2) was within a range from 0.01 wt % to 2 wt % both inclusive, the room-temperature cycle discharge capacity retention ratio was also higher.

Further, in Examples 7-2, and 7-6 to 7-12, compared to Comparative Example 7-3 in which the solvent included only the compound represented by Chemical Formula 46(2), the room-temperature cycle discharge capacity retention ratio and the high-temperature storage discharge capacity retention ratio were higher, and both values were a high 80's percent.

Therefore, it was confirmed that in the secondary battery according to the embodiment, in the case where the anode 34 included artificial graphite as the anode active material, when the solvent of the electrolytic solution included both of the sulfone compound and the halogenated carbonate, the cycle characteristics and the storage characteristics were improved. It was confirmed that in this case, when the content of the compound represented by Chemical Formula 35 in the solvent was within a range from 0.01 wt % to 10 wt % both inclusive, superior characteristics were obtained.

Moreover, when Examples 7-2, 7-6 and 7-7 which had a commonality in that R1 in Chemical Formula 35 was a straight-chain alkylene group were compared, there was a tendency that in Examples 7-2 and 7-6 in which the number of carbon atoms in R1 was 2 or less, the room-temperature cycle discharge capacity retention ratio and the high-temperature storage discharge capacity retention ratio were higher than those in Example 7-7 in which the number of carbon atoms in R1 was 3 or more. This tendency was the same in Examples 7-8 to 7-10 which had a commonality in that R1 was a halogenated alkylene group.

Therefore, it was confirmed that in the secondary battery according to the embodiment, in the case where R1 in Chemical Formula 35 was a straight-chain alkylene group or a halogenated alkylene group, when the number of carbon atoms was 2 or less, the cycle characteristics and the storage characteristics were further improved.

Further, with reference to swelling in Comparative Example 7-1 in which the solvent did not include FEC and the compound represented by Chemical Formula 46(2), in Comparative Example 7-2 in which only FEC was included, swelling was greatly increased, and in Example 7-2 in which FEC and the compound represented by Chemical Formula 46(2) were included, an increase in swelling was reduced.

This result showed the following. FEC had an advantage of greatly increasing the room-temperature cycle discharge capacity retention ratio. However, it was difficult for FEC to greatly increase the high-temperature storage discharge capacity retention ratio, and FEC had a disadvantage of greatly increasing swelling. Moreover, the compound represented by Chemical Formula 46(2) had an advantage of preventing swelling. However, the compound had a disadvantage of being unable to greatly increase the room-temperature cycle discharge capacity retention ratio and the high-temperature storage discharge capacity retention ratio. On the other hand, when FEC and the compound represented by Chemical Formula 46(2) were used together, while swelling was prevented, the room-temperature cycle discharge capacity retention ratio and the high-temperature storage discharge capacity retention ratio were greatly increased.

In Comparative Examples 7-4 and 7-5 in which the solvent included VC, the room-temperature cycle discharge capacity retention ratio and the high-temperature storage discharge capacity retention ratio were higher than those in Comparative Example 7-1, but the room-temperature cycle discharge capacity retention ratio and the high-temperature storage discharge capacity retention ratio in Comparative Examples 74 and 7-5 did not exceed those in Example 7-2 in which FEC was included. This result showed that to increase the room-temperature cycle discharge capacity retention ratio and the high-temperature storage discharge capacity retention ratio, FEC had an advantage over VC.

Therefore, it was confirmed that in the secondary battery according to the embodiment, when the sulfone compound was used with the halogenated carbonate, not only the cycle characteristics and the storage characteristics but also the swelling characteristics were improved. It was confirmed that in this case, a higher effect than that in the case where the sulfone compound was used with the cyclic carbonate including an unsaturated bond was obtained.

The result in the case where the solvent includes fluoromethyl methyl carbonate is not shown here. However, fluoromethyl methyl carbonate has the same functions as FEC, so it is obvious that even in the case where fluoromethyl methyl carbonate is included, the same effects are obtained. The same holds for the case where two or more above-described halogenated carbonates of the same kind or different kinds are mixed.

Examples 8-1 and 8-2

Secondary batteries were formed by the same steps as those in Example 7-2, except that as the halogenated carbonate (the cyclic carbonate represented by Chemical Formula 37 which included a halogen), instead of FEC, t-DFEC (Example 8-1) or c-DFEC (Example 8-2) was used.

Example 8-3

A secondary battery was formed by the same steps as those in Example 8-2, except that as the halogenated carbonate (the chain carbonate represented by Chemical Formula 36 which included a halogen), BFDMC was added. At that time, the content of BFDMC in the solvent was 1 wt %.

Comparative Example 8

A secondary battery was formed by the same steps as those in Example 8-1, except that the compound represented by Chemical Formula 46(2) was not included.

When the cycle characteristics, the storage characteristics and the swelling characteristics of the secondary batteries of Examples 8-1 to 8-3 and Comparative Example 8 were determined, results shown in Table 8 were obtained.

cycle discharge capacity retention ratio and the high-temperature storage discharge capacity retention ratio over FEC, t-DFEC or the like had a disadvantage of greatly increasing swelling. However, when t-DFEC or the like was used with the compound represented by Chemical Formula 46(2), while swelling was prevented, the room-temperature cycle discharge capacity retention ratio and the high-temperature storage discharge capacity retention ratio were greatly increased.

Therefore, it was confirmed that in the secondary battery according to the embodiment, even if the kind of the halogenated carbonate was changed, the cycle characteristics, the storage characteristics and the swelling characteristics were improved. It was confirmed that in this case, when the dihalogenated carbonate rather than the monohalogenated carbonate was used as the halogenated carbonate, the characteristics were further improved.

Example 9-1

A secondary battery was formed by the same steps as those in Example 7-2, except that as the solvent, propylene carbon-

TABLE 8

Anode active material: artificial graphite

| | | SOLVENT | | | ROOM-TEMPERATURE CYCLE DISCHARGE CAPACITY RETENTION RATIO | HIGH-TEMPERATURE STORAGE DISCHARGE CAPACITY RETENTION RATIO | SWELLING |
|---|---|---|---|---|---|---|---|
| | ELECTROLYTE SALT | HALOGENATED CARBONATE KIND | SULFONE COMPOUND KIND | WT % | (%) | (%) | (mm) |
| EXAMPLE 7-2 | LiPF$_6$ 1 mol/kg | EC + DEC | FEC | CHEMICAL FORMULA 46(2) | 1 | 90 | 90 | 0.321 |
| EXAMPLE 8-1 | | | t-DFEC | | | 92 | 91 | 0.401 |
| EXAMPLE 8-2 | | | c-DFEC | | | 92 | 90 | — |
| EXAMPLE 8-3 | | | FEC + BFDMC | | | 92 | 91 | — |
| COMPARATIVE EXAMPLE 7-1 | LiPF$_6$ 1 mol/kg | EC + DEC | — | — | — | 80 | 84 | 0.248 |
| COMPARATIVE EXAMPLE 8 | | | t-DFEC | — | — | 85 | 85 | 0.851 |

As shown in Table 8, in Examples 8-1 and 8-2 in which the solvent included T-DFEC or the like, compared to Example 7-2 in which FEC was included, the room-temperature cycle discharge capacity retention ratio was higher, and the high-temperature storage discharge capacity retention ratio was equal or higher. In Example 8-1 in which the solvent included the compound represented by Chemical Formula 46(2), the room-temperature cycle discharge capacity retention ratio and high-temperature storage discharge capacity retention ratio were higher than those in Comparative Example 8 in which the compound represented by Chemical Formula 46(2) was not included. In Example 8-3 in which the solvent included FEC and BFDMC, a room-temperature cycle discharge capacity retention ratio and a high-temperature storage discharge capacity retention ratio which were substantially equal to those in Examples 8-1 and 8-2 in which t-DFEC or the like was included were obtained.

With reference to swelling in Comparative Example 8 in which the solvent did not include FEC and the compound represented by Chemical Formula 46(2), in Comparative Example 8 in which only t-DFEC was included, swelling was greatly increased, but in Example 8-1 in which t-DFEC and the compound represented by Chemical Formula 46(2) were included, an increase in swelling was reduced.

These result showed the following. Although t-DFEC or the like had an advantage of increasing the room-temperature ate (PC) was added. At that time, the mixture ratio of EC, DEC and PC was a weight ratio of 20:60:20.

Examples 9-2 and 9-3

Secondary batteries were formed by the same steps as those in Example 7-2, except that as the solvent, instead of DEC, EMC (Example 9-2) or DMC (Example 9-3) was used.

Examples 9-4 and 9-5

Secondary batteries were formed by the same steps as those in Example 7-2, except that as the solvent, PRS (Example 9-4) as the sultone or SBAH (Example 9-5) as the acid anhydride was added. At that time, the content of PRS or the like in the solvent was 1 wt %.

When the cycle characteristics and the storage characteristics of the secondary batteries of Examples 9-1 to 9-5 were determined, results shown in Table 9 were obtained.

TABLE 9

Anode active material: artificial graphite

| | ELECTROLYTE SALT | SOLVENT KIND | HALOGENATED CARBONATE | SULFONE COMPOUND KIND | WT % | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|---|
| EXAMPLE 7-2 | LiPF$_6$ 1 mol/kg | — | FEC | CHEMICAL FORMULA 46(2) | 1 | 90 | 90 |
| EXAMPLE 9-1 | | EC + DEC + PC | | | | 89 | 92 |
| EXAMPLE 9-2 | | EC + EMC | | | | 89 | 88 |
| EXAMPLE 9-3 | | EC + DMC | | | | 89 | 86 |
| EXAMPLE 9-4 | | EC + DEC + PRS | | | | 90 | 92 |
| EXAMPLE 9-5 | | EC + DEC + SBAH | | | | 92 | 94 |

As shown in Table 9, in Examples 9-1 to 9-5 in which the solvent included PC or the like, compared to Example 7-2 in which PC or the like was not included, the room-temperature cycle discharge capacity retention ratio and the high-temperature storage discharge capacity retention ratio were substantially equal or higher, and were a high 80's percent or higher. In this case, in Examples 9-1, 94 and 9-5 in which PC or the like was added in the solvent, compared to Examples 9-2 and 9-3 in which EMC or the like was substituted for a part of the solvent, the room-temperature cycle discharge capacity retention ratio was equal or higher, and the high-temperature storage discharge capacity retention ratio was higher.

Therefore, it was confirmed that in the secondary battery according to the embodiment, even if the composition of the solvent was changed, the cycle characteristics and the storage characteristics were improved. It was confirmed that in this case, when PC or the like was added to the solvent, the characteristics were further improved.

Examples 10-1 to 10-3

Secondary batteries were formed by the same steps as those in Example 7-2, except that as the electrolyte salt, lithium tetrafluoroborate (Example 10-1), the compound represented by Chemical Formula 27(6) as the compound represented by Chemical Formula 24 (Example 10-2) or the compound represented by Chemical Formula 33(1) as the compound represented by Chemical Formula 31 (Example 10-3) was added. At that time, the concentration of lithium hexafluorophosphate in the electrolytic solution was 0.9 mol/kg, and the concentration of lithium tetrafluoroborate or the like was 0.1 mol/kg.

When the cycle characteristics and the storage characteristics of the secondary batteries of Examples 10-1 to 10-3 were determined, results shown in Table 10 were obtained.

TABLE 10

Anode active material: artificial graphite

| | ELECTROLYTE SALT | | SOLVENT KIND | HALOGENATED CARBONATE | SULFONE COMPOUND KIND | WT % | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|---|---|
| EXAMPLE 7-2 | LiPF$_6$ 1 mol/kg | | EC + DEC | FEC | CHEMICAL FORMULA 46(2) | 1 | 90 | 90 |
| EXAMPLE 10-1 | LiPF$_6$ 0.9 mol/kg | LIBF$_4$ 0.1 mol/kg | | | | | 90 | 92 |
| EXAMPLE 10-2 | LiPF$_6$ 0.9 mol/kg | CHEMICAL FORMULA 27(6) 0.1 mol/kg | | | | | 91 | 92 |
| EXAMPLE 10-3 | LiPF$_6$ 0.9 mol/kg | CHEMICAL FORMULA 33(1) 0.1 mol/kg | | | | | 90 | 91 |

As shown in Table 10, in Examples 10-1 to 10-3 in which the electrolyte salt included lithium tetrafluoroborate or the like, compared to Example 7-2 in which lithium tetrafluoroborate or the like was not included, the room-temperature cycle discharge capacity retention ratio was equal or higher, and the high-temperature storage discharge capacity retention ratio was higher.

Therefore, it was confirmed in the secondary battery according to the embodiment, even if the kind of the electrolyte salt was changed, the cycle characteristics and the storage characteristics were improved. It was confirmed that in this case, when the electrolyte salt included lithium tetrafluoroborate, the compound represented by Chemical Formula 24 or the compound represented by Chemical Formula 31, the characteristics were further improved.

The result in the case where the electrolyte salt includes at least one kind selected from the group consisting of lithium perchlorate and lithium hexafluoroarsenate, at least one kind selected from the group consisting of the compounds represented by Chemical Formulas 25 and 26, or at least one kind selected from the group consisting of the compounds represented by Chemical Formulas 30 and 31 is not shown here. However, lithium perchlorate or the like has the same functions as lithium tetrafluoroborate or the like, so it is obvious that even in the case where lithium perchlorate or the like is included, the same effects are obtained. The same holds for the case where two or more above-described electrolyte salts of the same kind or different kinds are mixed.

Examples 11-1 to 11-12

Secondary batteries were formed by the same steps as those in Examples 7-1 to 7-12, except that as the anode active material, instead of artificial graphite, silicon was used to form the anode active material layer 34B, and the content of FEC was changed to 5 wt %. In the case where the anode active material layer 34B was formed, silicon was deposited on the anode current collector 34A by an electron beam evaporation method.

Comparative Examples 11-1 to 11-5

Secondary batteries were formed by the same steps as those in Comparative Examples 7-1 to 7-5, except that as in the case of Examples 11-1 to 11-12, as the anode active material, silicon was used to form the anode active material layer 34B.

When the cycle characteristics, the storage characteristics and the swelling characteristics of the secondary batteries of Examples 11-1 to 11-12 and Comparative Examples 11-1 to 11-5 were determined, results shown in Table 11 were obtained.

TABLE 11

Anode active material: silicon

| | ELECTROLYTE SALT | SOLVENT | | | | ROOM-TEMPERATURE CYCLE DISCHARGE CAPACITY RETENTION RATIO (%) | HIGH-TEMPERATURE STORAGE DISCHARGE CAPACITY RETENTION RATIO (%) | SWELLING (mm) |
|---|---|---|---|---|---|---|---|---|
| | | HALOGENATED CARBONATE KIND | | SULFONE COMPOUND | | | | |
| | | | | KIND | WT % | | | |
| EXAMPLE 11-1 | $LiPF_6$ 1 mol/kg | EC + DEC | FEC | CHEMICAL FORMULA 46(2) | 0.01 | 60 | 87 | — |
| EXAMPLE 11-2 | | | | | 1 | 64 | 90 | 0.425 |
| EXAMPLE 11-3 | | | | | 2 | 69 | 90 | — |
| EXAMPLE 11-4 | | | | | 5 | 73 | 88 | — |
| EXAMPLE 11-5 | | | | | 10 | 76 | 88 | — |
| EXAMPLE 11-6 | | | | CHEMICAL FORMULA 46(1) | 1 | 69 | 90 | — |
| EXAMPLE 11-7 | | | | CHEMICAL FORMULA 46(3) | 1 | 60 | 87 | — |
| EXAMPLE 11-8 | | | | CHEMICAL FORMULA 46(4) | 1 | 67 | 88 | — |
| EXAMPLE 11-9 | | | | CHEMICAL FORMULA 46(5) | 1 | 65 | 88 | — |
| EXAMPLE 11-10 | | | | CHEMICAL FORMULA 46(6) | 1 | 62 | 88 | — |
| EXAMPLE 11-11 | | | | CHEMICAL FORMULA 46(7) | 1 | 60 | 87 | — |
| EXAMPLE 11-12 | | | | CHEMICAL FORMULA 46(8) | 1 | 61 | 87 | — |
| COMPARATIVE EXAMPLE 11-1 | $LiPF_6$ 1 mol/kg | EC + DEC | — | — | — | 41 | 82 | 0.267 |
| COMPARATIVE EXAMPLE 11-2 | | | FEC | — | — | 58 | 86 | 0.601 |
| COMPARATIVE EXAMPLE 11-3 | | | — | CHEMICAL FORMULA 46(2) | 1 | 50 | 86 | — |
| COMPARATIVE EXAMPLE 11-4 | | EC + DEC + | — | — | — | 70 | 85 | — |

TABLE 11-continued

Anode active material: silicon

| | ELECTROLYTE SALT | SOLVENT | | SULFONE COMPOUND | | ROOM-TEMPERATURE CYCLE DISCHARGE CAPACITY RETENTION RATIO (%) | HIGH-TEMPERATURE STORAGE DISCHARGE CAPACITY RETENTION RATIO (%) | SWELLING (mm) |
|---|---|---|---|---|---|---|---|---|
| | | KIND | HALOGENATED CARBONATE | KIND | WT % | | | |
| COMPARATIVE EXAMPLE 11-5 | | VC | — | CHEMICAL FORMULA 46(2) | 1 | 68 | 85 | — |

As shown in Table 11, in the case where silicon was used as the anode active material, substantially the same results as those shown in Table 7 were obtained. In other words, in the case where the solvent included FEC and the compounds represented by Chemical Formulas 46(1) to 46(8), when the content of the compound represented by Chemical Formula 46(2) in the solvent was 0.01 wt % to 10 wt % both inclusive, a room-temperature cycle discharge capacity retention ratio and a high-temperature storage discharge capacity retention ratio which were substantially equal to or higher than those in the case where neither of them was included, or the case where only one of them was included were obtained. Moreover, when the cases where there was a commonality in that R1 in Chemical Formula 35 was a straight-chain alkylene group or a halogenated alkylene group were compared, there was a tendency that in the case where the number of carbon atoms in R1 was 2 or less, the room-temperature cycle discharge capacity retention ratio and the high-temperature storage discharge capacity retention ratio were equal to or higher than those in the case where the number of carbon atoms in R1 is 3 or more. Further, with reference to swelling in the case where the solvent did not include FEC and the compound represented by Chemical Formula 46(2), in the case where only FEC was included, swelling was greatly increased. However, in the case where FEC and the compound represented by Chemical Formula 46(2) were included, an increase in swelling was reduced. In particular, in the case where the solvent included VC, the room-temperature cycle discharge capacity retention ratio and the high-temperature storage discharge capacity retention ratio did not exceed those in the case where FEC was included.

Therefore, it was confirmed in the secondary battery according to the embodiment, in the case where the anode 34 included silicon as the anode active material, when the solvent of the electrolytic solution included both of the sulfone compound and the halogenated carbonate, the cycle characteristics and the storage characteristics were improved. It was confirmed that in this case, when the content of the compound represented by Chemical Formula 35 in the solvent was within a range from 0.01 wt % to 10 wt % both inclusive, superior characteristics were obtained, and in the case where R1 in Chemical Formula 35 was a straight-chain alkylene group or a halogenated alkylene group, when the number of carbon atoms was 2 or less, the characteristics were further improved. Moreover, it was confirmed that when the sulfone compound was used with the halogenated carbonate, not only the cycle characteristics and the storage characteristics but also the swelling characteristics were improved.

Examples 12-1 to 12-3

Secondary batteries were formed by the same steps as those in Examples 8-1 to 8-3, except that as in the case of Examples 11-1 to 11-12, silicon was used as the anode active material to form the anode active material layer 34B, and the content of t-DFEC or the like was changed to 5 wt %.

Comparative Example 12

A secondary battery was formed by the same steps as those in Comparative Example 8, except that as in the case of Examples 11-1 to 11-12, silicon was used as the anode active material to form the anode active material layer 34B, and the content of t-DFEC was changed to 5 wt %.

When the cycle characteristics, the storage characteristics and the swelling characteristics of the secondary batteries of Examples 12-1 to 12-3 and Comparative Example 12 were determined, results shown in Table 12 were obtained.

TABLE 12

Anode active material: silicon

| | ELECTROLYTE SALT | SOLVENT | | SULFONE COMPOUND | | ROOM-TEMPERATURE CYCLE DISCHARGE CAPACITY RETENTION RATIO (%) | HIGH-TEMPERATURE STORAGE DISCHARGE CAPACITY RETENTION RATIO (%) | SWELLING (mm) |
|---|---|---|---|---|---|---|---|---|
| | | KIND | HALOGENATED CARBONATE | KIND | WT % | | | |
| EXAMPLE 11-2 | LiPF$_6$ | — | FEC | CHEMICAL FORMULA 46(2) | 1 | 64 | 90 | 0.425 |
| EXAMPLE 12-1 | 1 mol/kg | EC + DEC | t-DFEC | | | 84 | 91 | 0.531 |
| EXAMPLE 12-2 | | | c-DFEC | | | 83 | 90 | — |
| EXAMPLE 12-3 | | | FEC + BFDMC | | | 64 | 88 | — |

TABLE 12-continued

Anode active material: silicon

| | ELECTROLYTE | | SOLVENT | | | ROOM-TEMPERATURE CYCLE DISCHARGE CAPACITY | HIGH-TEMPERATURE STORAGE DISCHARGE CAPACITY | |
|---|---|---|---|---|---|---|---|---|
| | | | | SULFONE COMPOUND | | RETENTION RATIO | RETENTION RATIO | SWELLING |
| | SALT | KIND | HALOGENATED CARBONATE | KIND | WT % | (%) | (%) | (mm) |
| COMPARATIVE EXAMPLE 11-1 | LiPF$_6$ 1 mol/kg | EC + DEC | — | — | — | 41 | 82 | 0.267 |
| COMPARATIVE EXAMPLE 12 | | | t-DFEC | — | — | 80 | 85 | 0.866 |

As shown in Table 12, in the case where silicon was used as the anode active material, substantially the same results as those in Table 8 were obtained. In other words, in the case where the solvent included t-DFEC or the like, compared to the case where FEC was included, the room-temperature cycle discharge capacity retention ratio was higher, and the high-temperature storage discharge capacity retention ratio was equal or higher. In the case where the solvent included the compound represented by Chemical Formula 46(2), the room-temperature cycle discharge capacity retention ratio and the high-temperature storage discharge capacity retention ratio were higher than those in the case where the compound represented by Chemical Formula 46(2) was not included. In the case where the solvent included FEC and BFDMC, a room-temperature cycle discharge capacity retention ratio and a high-temperature storage discharge capacity retention ratio which were substantially equal to those in the case where t-DFEC or the like was included were obtained: In the case where the solvent included only t-DFEC, swelling was greatly increased. However, in the case where t-DFEC and the compound represented by Chemical Formula 46(2) were included, an increase in swelling was reduced.

Therefore, it was confirmed that in the secondary battery according to the embodiment, in the case where the kind of the halogenated carbonate was changed, the cycle characteristics, the storage characteristics and the swelling characteristic were improved. It was confirmed that in this case, when the dihalogenated carbonate rather than the monohalogenated carbonate was used as the halogenated carbonate, the characteristics were further improved.

Examples 13-1 to 13-5

Secondary batteries were formed by the same steps as those in Examples 9-1 to 9-5, except that as in the case where Examples 11-1 to 11-12, silicon was used as the anode active material to form the anode active material layer 34B, and the content of FEC was changed to 5 wt %.

When the cycle characteristics and the storage characteristics of the secondary batteries of Examples 13-1 to 13-5 were determined, results shown in Table 13 were obtained.

TABLE 13

Anode active material: silicon

| | ELECTROLYTE | | SOLVENT | | | ROOM-TEMPERATURE CYCLE DISCHARGE CAPACITY | HIGH-TEMPERATURE STORAGE DISCHARGE CAPACITY |
|---|---|---|---|---|---|---|---|
| | | | | SULFONE COMPOUND | | RETENTION RATIO | RETENTION RATIO |
| | SALT | KIND | HALOGENATED CARBONATE | KIND | WT % | (%) | (%) |
| EXAMPLE 11-2 | LiPF$_6$ 1 mol/kg | — | FEC | CHEMICAL FORMULA 46(2) | 1 | 64 | 90 |
| EXAMPLE 13-1 | | EC + DEC + PC | | | | 64 | 92 |
| EXAMPLE 13-2 | | EC + EMC | | | | 63 | 88 |
| EXAMPLE 13-3 | | EC + DMC | | | | 63 | 86 |
| EXAMPLE 13-4 | | EC + DEC + PRS | | | | 64 | 92 |
| EXAMPLE 13-5 | | EC + DEC + SBAH | | | | 66 | 94 |

As shown in Table 13, in the case where silicon was used as the anode active material, substantially the same results as those in Table 9 were obtained. In other words, in the case where the solvent included PC or the like, compared to the case where PC or the like was not included, the room-temperature cycle discharge capacity retention ratio and the high-temperature storage discharge capacity retention ratio were substantially equal or higher. In this case, in the case where PC or the like was added to the solvent, compared to the case where EMC or the like was substituted for a part of the solvent, the room-temperature cycle discharge capacity retention ratio was equal or higher, and the high-temperature storage discharge capacity retention ratio was higher.

Therefore, it was confirmed that in the secondary battery according to the embodiment, even if the composition of the solvent was changed, the cycle characteristics and the storage characteristics were improved. It was confirmed that in this case, when the PC or the like was added to the solvent, the characteristics were further improved.

Examples 14-1 to 14-3

Secondary batteries were formed by the same steps as those in Examples 10-1 to 10-3, except that as in the case of Examples 11-1 to 11-12, silicon was used as the anode active material to form the anode active material layer 34B, and the content of the FEC was changed to 5 wt %.

When the cycle characteristics and the storage characteristics of the secondary batteries of Examples 14-1 to 14-3 were determined, results shown in Table 14 were obtained.

case, when the electrolyte salt included lithium tetrafluoroborate, the compound represented by Chemical Formula 24 or the compound represented by Chemical Formula 31, the cycle characteristics and the storage characteristics were further improved.

It was confirmed from the above-described results shown in Tables 7 to 14 that in the secondary battery according to the embodiment, the solvent of the electrolytic solution included the sulfone compound represented by Chemical Formula 35 and at least one kind selected from the group consisting of the chain carbonate represented by Chemical Formula 36 which included a halogen and the cycle carbonate represented by Chemical Formula 37 which included a halogen, irrespective of the kind of the anode active material or the composition of the solvent, the battery characteristics such as the cycle characteristics, the storage characteristics and the swelling characteristics were improved. It was confirmed that in this case, in the case where silicon (the material being capable of inserting and extracting lithium and including at least one kind selected from metal elements and metalloid elements) was used as the anode active material, the rate of increase of the discharge capacity retention ratio was larger than that in the

TABLE 14

Anode active material: silicon

| | ELECTROLYTE SALT | | SOLVENT | | | | ROOM-TEMPERATURE CYCLE DISCHARGE CAPACITY RETENTION RATIO (%) | HIGH-TEMPERATURE STORAGE DISCHARGE CAPACITY RETENTION RATIO (%) |
|---|---|---|---|---|---|---|---|---|
| | | KIND | HALOGENATED CARBONATE | SULFONE COMPOUND KIND | WT % | | | |
| EXAMPLE 11-2 | LiPF$_6$ 1 mol/kg | EC + DEC | FEC | CHEMICAL FORMULA 46(2) | 1 | | 64 | 90 |
| EXAMPLE 14-1 | LiPF$_6$ 0.9 mol/kg  LIBF$_4$ 0.1 mol/kg | | | | | | 64 | 92 |
| EXAMPLE 14-2 | LiPF$_6$ 0.9 mol/kg  CHEMICAL FORMULA 27(6) 0.1 mol/kg | | | | | | 68 | 92 |
| EXAMPLE 14-3 | LiPF$_6$ 0.9 mol/kg  CHEMICAL FORMULA 33(1) 0.1 mol/kg | | | | | | 64 | 91 |

As shown in Table 14, in the case where silicon was used as the anode active material, the same results as those in Table 10 were obtained. In other words, in the case where the electrolyte salt included lithium tetrafluoroborate or the like, compared to the case where lithium tetrafluoroborate or the like was not included, the room-temperature cycle discharge capacity retention ratio was equal or higher, and the high-temperature storage discharge capacity retention ratio was higher.

Therefore, it was confirmed that in the secondary battery according to the embodiment, even if the kind of the electrolyte salt was changed, the cycle characteristics and the storage characteristics were improved. It was confirmed that in this case where the carbon material was used as the anode active material, so a higher effect was obtained in the case where silicon was used. It was considered that the result was obtained, because when silicon which was advantageous to increase the capacity was used as the anode active material, compared to the case where the carbon material was used, the electrolytic solution was easily decomposed, so the decomposition inhibition effect of the electrolytic solution was exerted pronouncedly.

Finally, examples of the electrolytic solution and the secondary battery according to the third embodiment will be described below.

Example 15-1

A laminate film type secondary battery shown in FIGS. 3 and 4 was formed using artificial graphite as the anode active material. At that time, the secondary battery was a lithium-ion secondary battery in which the capacity of the anode 34 was represented on the basis of insertion and extraction of lithium.

At first, the cathode 33 and the anode 34 were formed by the same steps as those in Example 1-1.

Next, after EC, DEC and the compound represented by Chemical Formula 50(7) as the sulfone compound represented by Chemical Formula 49 were mixed to form a solvent, lithium hexafluorophosphate as the electrolyte salt was dissolved in the solvent to form the electrolytic solution. At that time, the mixture ratio of EC and DEC was a weight ratio of 30:70, and the content of the compound represented by Chemical Formula 50(7) in the solvent was 0.01 wt %, and the concentration of the electrolyte salt in the electrolytic solution was 1 mol/kg. The "wt %" is a unit in the case where the whole solvent was 100 wt %, and the same holds for the following examples.

Next, the laminate film type secondary battery was formed using the cathode 33 and the anode 34 by the same steps as those in Example 1-1.

Examples 15-2 to 15-4

Secondary batteries were formed by the same steps as those in Example 15-1, except that the content of the compound represented by Chemical Formula 50(7) in the solvent was 1 wt % (Example 15-2), 2 wt % (Example 15-3) or 5 wt % (Example 15-4).

Examples 15-5 to 15-7

Secondary batteries were formed by the same steps as those in Example 15-2, except that instead of the compound represented by Chemical Formula 50(7), the compound represented by Chemical Formula 50(1) (Example 15-5), the compound represented by Chemical Formula 51(6) (Example 15-6), or the compound represented by Chemical Formula 52(1) (Example 15-7) was used.

Comparative Example 15-1

A secondary battery was formed by the same steps as those in Example 15-1, except that the compound represented by Chemical Formula 50(7) was not added.

Comparative Examples 15-2 to 15-4

Secondary batteries were formed by the same steps as those in Example 15-2, except that instead of the sulfone compound represented by Chemical Formula 49 (the compound represented by Chemical Formula 50(7)), the sulfone compound represented by Chemical Formula 53 (Comparative Example 15-2), the sulfone compound represented by Chemical Formula 54 (Comparative Example 15-3) or the sulfone compound represented by Chemical Formula 55 (Comparative Example 15-4) was used.

When the cycle characteristics of the secondary batteries of Examples 15-1 to 15-7 and Comparative Examples 15-1 to 154 were determined, results shown in Table 15 were obtained.

TABLE 15

Anode active material: artificial graphite

| | ELECTROLYTE SALT | SOLVENT KIND | SULFONE COMPOUND KIND | WT % | DISCHARGE CAPACITY RETENTION RATIO (%) |
|---|---|---|---|---|---|
| EXAMPLE 15-1 | LiPF$_6$ 1 mol/kg | EC + DEC | CHEMICAL FORMULA 50(7) | 0.01 | 83 |
| EXAMPLE 15-2 | | | | 1 | 87 |
| EXAMPLE 15-3 | | | | 2 | 87 |
| EXAMPLE 15-4 | | | | 5 | 85 |
| EXAMPLE 15-5 | | | CHEMICAL FORMULA 50(1) | 1 | 85 |
| EXAMPLE 15-6 | | | CHEMICAL FORMULA 51(6) | 1 | 89 |
| EXAMPLE 15-7 | | | CHEMICAL FORMULA 52(1) | 1 | 85 |
| COMPARATIVE EXAMPLE 15-1 | LiPF$_6$ 1 mol/kg | EC + DEC | — | — | 80 |
| COMPARATIVE EXAMPLE 15-2 | | | CHEMICAL FORMULA 53 | 1 | 78 |
| COMPARATIVE EXAMPLE 15-3 | | | CHEMICAL FORMULA 54 | 1 | 76 |
| COMPARTIVE EXAMPLE 15-4 | | | CHEMICAL FORMULA 55 | 1 | 78 |

As shown in Table 15, in Examples 15-1 to 15-7 in which the solvent included the sulfone compound represented by Chemical Formula 49 (the compound represented by Chemical Formula 50(7) or the like), compared to Comparative Example 15-1 in which the sulfone compound represented by Chemical Formula 49 was not included or Comparative Examples 15-2 to 15-4 in which other sulfone compounds represented by Chemical Formulas 53 to 55 were included, the discharge capacity retention ratio was higher. This result showed that to improve the discharge capacity retention ratio, the sulfone compound represented by Chemical Formula 49 was more advantageous than other sulfone compounds represented by Chemical Formulas 53 to 55. More specifically, with reference to the discharge capacity retention ratio in Comparative Example 15-1 in which the solvent did not include any of the sulfone compounds, in Comparative Examples 15-2 to 154 in which other sulfone compounds represented by Chemical Formulas 53 to 55 were included, the discharge capacity retention ratio was reduced. However, in Examples 15-1 to 15-7 in which the sulfone compound represented by Chemical Formula 49 was included, the discharge capacity retention ratio was higher. In other words, in spite of a commonality in that the sulfone compounds represented by Chemical Formulas 49 and 53 to 55 had a sulfonyl fluoride type structure, the other sulfone compounds represented by Chemical Formulas 53 to 55 caused a decline in the discharge capacity retention ratio. However, the sulfone compound represented by Chemical Formula 49 caused an increase in the discharge capacity retention ratio. The result showed that to increase the discharge capacity retention ratio, the sulfone compound having a sulfonyl fluoride type structure preferably had a chain group including an unsaturated carbon bond.

In particular, when attention was focused on the content of the compound represented by Chemical Formula 50(7) in the solvent, in the case where the content was within a range from 0.01 wt % to 5 wt % both inclusive, a high discharge capacity retention ratio was obtained. In this case, there was a tendency that when the content was smaller than 0.01 wt % or larger than 5 wt %, the discharge capacity retention ratio was greatly reduced, and in the case where the content was larger than 5 wt %, the capacity was also greatly reduced.

% both inclusive, more specifically within a range from 1 wt % to 2 wt % both inclusive, the characteristics were further improved.

Examples 16-1 to 16-6

Secondary batteries were formed by the same steps as those in Example 15-2, except that as the solvent, VC (Example 16-1), FEC (Example 16-2), t-DFEC (Example 16-3), c-DFEC (Example 16-4), PRS (Example 16-5) or SBAH (Example 16-6) was added. At that time, the content of VC or the like in the solvent was 1 wt %.

Examples 16-7 and 16-8

Secondary batteries were formed by the same steps as those in Examples 16-2 and 16-3, except that as the solvent, PC was added. At that time, the mixture ratio of EC, DEC and PC was a weight ratio of 20:70:10.

Comparative Examples 16-1 and 16-2

Secondary batteries were formed by the same steps as those in Examples 16-1 and 16-2, except that the compound represented by Chemical Formula 50(7) was not added.

When the cycle characteristics of the secondary batteries of Examples 16-1 to 16-8 and Comparative Examples 16-1 and 16-2 were determined, results shown in Table 16 were obtained.

TABLE 16

| | Anode active material: artificial graphite | | | | |
|---|---|---|---|---|---|
| | ELECTROLYTE | SOLVENT | | | DISCHARGE CAPACITY RETENTION RATIO (%) |
| | SALT | KIND | SULFONE COMPOUND KIND | WT % | |
| EXAMPLE 15-2 | LiPF$_6$ 1 mol/kg | EC + DEC | CHEMICAL FORMULA 50(7) | 1 | 87 |
| EXAMPLE 16-1 | | EC + DEC VC | | | 90 |
| EXAMPLE 16-2 | | FEC | | | 91 |
| EXAMPLE 16-3 | | t-DFEC | | | 92 |
| EXAMPLE 16-4 | | c-DFEC | | | 92 |
| EXAMPLE 16-5 | | PRS | | | 89 |
| EXAMPLE 16-6 | | SBAH | | | 90 |
| EXAMPLE 16-7 | | EC + FEC | | | 91 |
| EXAMPLE 16-8 | | DEC + PC t-DFEC | | | 92 |
| COMPARATIVE EXAMPLE 16-1 | LiPF$_6$ 1 mol/kg | EC + DEC VC | — | — | 87 |
| COMPARATIVE EXAMPLE 16-2 | | FEC | | | 88 |

Therefore, it was confirmed that in the secondary battery according to the embodiment, in the case where the anode 34 included artificial graphite as the anode active material, when the solvent of the electrolytic solution included the sulfone compound represented by Chemical Formula 49, the cycle characteristics were improved. It was confirmed that in this case, the content of the sulfone compound represented by Chemical Formula 49 was within a range from 0.01 wt % to 5 wt % both inclusive, superior characteristics were obtained, and when the content was within a range from 1 wt % to 5 wt As shown in Table 16, in Examples 16-1 to 16-8 in which the solvent included VC or the like, the discharge capacity retention ratio was higher than that in Example 15-2 in which VC or the like was not included. In this case, when FEC, t-DFEC and c-DFEC were compared, there was a tendency that in the case where t-DFEC or c-DFEC was included, the discharge capacity retention ratio was higher than that in the case where FEC was included. Moreover, in Examples 16-7 and 16-8 in which the solvent included PC, a discharge capacity retention ratio equal to that in Examples 16-1 and 16-2 in which PC was not included was obtained, and even if PC was included, a decline in the discharge capacity retention ratio was not shown. In Examples 16-1 and 16-2 in which the solvent included the compound represented by Chemical Formula 50(7), the discharge capacity retention ratio was higher than that in Comparative Examples 16-1 and 16-2 in which the compound represented by Chemical Formula 50(7) was not included.

Therefore, it was confirmed that in the secondary battery according to the embodiment, when the solvent included the cyclic carbonate including an unsaturated bond, the cyclic carbonate represented by Chemical Formula 21 which included a halogen, a sultone or an acid anhydride, the cycle characteristics were further improved, and when the solvent included propylene carbonate, the cycle characteristics were improved. In particular, it was confirmed that in the case where the cyclic carbonate represented by Chemical Formula 21 which included a halogen was used, the more the number of halogens increased, the more the cycle characteristics were improved.

The result in the case where the solvent includes the chain carbonate represented by Chemical Formula 20 which includes a halogen is not shown here. However, the chain carbonate including a halogen has the same functions as the cyclic carbonate including a halogen, so it is obvious that even in the case where the chain carbonate including a halogen is included, the same effects are obtained. The same holds for the case where the chain carbonate including a halogen and the cyclic carbonate including a halogen are mixed, or the case where two or more kinds of the chain carbonates and two or more kinds of the cyclic carbonates are mixed.

Examples 17-1 and 17-2

Secondary batteries were formed by the same steps as those in Example 15-2, except that as the electrolyte salt, lithium tetrafluoroborate (Example 17-1) or the compound represented by Chemical Formula 27(6) as the compound represented by Chemical Formula 24 (Example 17-2) was added. At that time, the concentration of lithium hexafluorophosphate in the electrolytic solution was 0.9 mol/kg, and the concentration of lithium tetrafluoroborate or the like was 0.1 mol/kg.

Comparative Example 17

A secondary battery was formed by the same steps as those in Example 17-1, except that the compound represented by Chemical Formula 50(7) was not added.

When the cycle characteristics of the secondary batteries of Examples 17-1 and 17-2 and Comparative Example 17 were determined, results shown in Table 17 were obtained.

TABLE 17

| | | | | SOLVENT | | DISCHARGE CAPACITY RETENTION RATIO |
|---|---|---|---|---|---|---|
| | | ELECTROLYTE SALT | KIND | SULFONE COMPOUND KIND | WT % | (%) |
| EXAMPLE 15-2 | | LiPF$_6$ 1 mol/kg | EC + DEC | CHEMICAL FORMULA 50(7) | 1 | 87 |
| EXAMPLE 17-1 | LiPF$_6$ 0.9 mol/kg | LIBF$_4$ 0.1 mol/kg | | | | 89 |
| EXAMPLE 17-2 | LiPF$_6$ 0.9 mol/kg | CHEMICAL FORMULA 27(6) 0.1 mol/kg | | | | 88 |
| COMPARATIVE EXAMPLE 17 | LiPF$_6$ 0.9 mol/kg | LIBF$_4$ 0.1 mol/kg | EC + DEC | — | — | 84 |

As shown in Table 17, in Examples 17-1 and 17-2 in which the electrolyte salt included lithium tetrafluoroborate or the like, the discharge capacity retention ratio was higher than that in Example 15-2 in which lithium tetrafluoroborate or the like was not included. In Example 17-1 in which the solvent included the compound represented by Chemical Formula 50(7), the discharge capacity retention ratio was higher than that in Comparative Example 17 in which the compound represented by Chemical Formula 50(7) was not included.

It was confirmed that in the secondary battery according to the embodiment, when the electrolyte salt included lithium tetrafluoroborate or the compound represented by Chemical Formula 24, the cycle characteristics were further improved.

The result in the case where the electrolyte salt includes at least one kind selected from the group consisting of lithium perchlorate and lithium hexafluoroarsenate, at least one kind selected from the group consisting of the compounds represented by Chemical Formulas 25 and 26, or at least one kind selected from the group consisting of the compounds represented by Chemical Formulas 30 to 32 is not shown here. However, lithium perchlorate or the like has the same functions as lithium tetrafluoroborate or the like, so it is obvious that even in the case where lithium perchlorate or the like is included, the same effects are obtained. The same holds for the case where two or more kinds of the above-described electrolyte salts are mixed.

Examples 18-1 to 18-7

Secondary batteries were formed by the same steps as those in Examples 15-1 to 15-7, except that as the anode active material, instead of artificial graphite, silicon was used to form the anode active material layer 34B. In the case where the anode active material layer 34B was formed, silicon was deposited on the anode current collector 34A by an electron beam evaporation method.

Comparative Examples 18-1 to 18-4

Secondary batteries were formed by the same steps as those in Comparative Examples 15-1 to 15-4, except that as in the case of Examples 18-1 to 18-7, silicon was used to form the anode active material layer 22B.

When the cycle characteristics of the secondary batteries of Examples 18-1 to 18-7 and Comparative Examples 18-1 to 184 were determined, results shown in Table 18 were obtained.

TABLE 18

Anode active material: silicon

|  | ELECTROLYTE SALT | SOLVENT KIND | SULFONE COMPOUND KIND | WT % | DISCHARGE CAPACITY RETENTION RATIO (%) |
|---|---|---|---|---|---|
| EXAMPLE 18-1 | LiPF$_6$ 1 mol/kg | EC + DEC | CHEMICAL FORMULA 50(7) | 0.01 | 45 |
| EXAMPLE 18-2 |  |  |  | 1 | 48 |
| EXAMPLE 18-3 |  |  |  | 2 | 55 |
| EXAMPLE 18-4 |  |  |  | 5 | 62 |
| EXAMPLE 18-5 |  |  | CHEMICAL FORMULA 50(1) | 1 | 58 |
| EXAMPLE 18-6 |  |  | CHEMICAL FORMULA 51(6) | 1 | 54 |
| EXAMPLE 18-7 |  |  | CHEMICAL FORMULA 52(1) | 1 | 55 |
| COMPARATIVE EXAMPLE 18-1 | LiPF$_6$ 1 mol/kg | EC + DEC | — | — | 40 |
| COMPARATIVE EXAMPLE 18-2 |  |  | CHEMICAL FORMULA 53 | 1 | 38 |
| COMPARATIVE EXAMPLE 18-3 |  |  | CHEMICAL FORMULA 54 | 1 | 36 |
| COMPARATIVE EXAMPLE 18-4 |  |  | CHEMICAL FORMULA 55 | 1 | 39 |

As shown in Table 18, in the case where silicon was used as the anode active material, substantially the same results as those in Table 15 were obtained. In other words, in Examples 18-1 to 18-7 in which the solvent included the sulfone compound represented by Chemical Formula 49 (the compound represented by Chemical Formula 50(7) or the like), the discharge capacity retention ratio was higher than that in Comparative Examples 18-1 to 18-4. In this case, in the case where the content of the compound represented by Chemical Formula 50(7) in the solvent was within a range from 0.01 wt % to 5 wt % both inclusive, a high discharge capacity retention ratio was obtained. Moreover, in the case where the sulfone compound represented by Chemical Formula 49 (the compound represented by Chemical Formula 50(7) or the like) was included, the discharge capacity retention ratio was higher than that in the case where other sulfone compounds represented by Chemical Formulas 53 to 55.

Therefore, it was confirmed that in the secondary battery according to the embodiment, in the case where the anode 34 included silicon as the anode active material, when the solvent of the electrolytic solution included the sulfone compound represented by Chemical Formula 49, as in the case where artificial graphite was included, the cycle characteristics were improved. It was confirmed that in this case, when the content of the sulfone compound represented by Chemical Formula 49 in the solvent was 0.01 wt % to 5 wt % both inclusive, superior characteristics were obtained, and when the content was within a range from 1 wt % to 5 wt % both inclusive, more specifically within a range from 2 wt % to 5 wt % both inclusive, the characteristics were further improved.

Examples 19-1 to 19-8

Secondary batteries were formed by the same steps as those in Examples 16-1 to 16-8, except that as in the case of Examples 18-1 to 18-7, silicon was used to form the anode active material layer 34B.

Comparative Examples 19-1 and 19-2

Secondary batteries were formed by the same steps as those in Comparative Examples 16-1 and 16-2, except that as in the case of Examples 18-1 to 18-7, silicon was used to form the anode active material layer 34B.

When the cycle characteristics of the secondary batteries of Examples 19-1 to 19-8 and Comparative Examples 19-1 and 19-2 were determined, results shown in Table 19 were obtained.

TABLE 19

Anode active material: silicon

| | ELECTROLYTE SALT | SOLVENT KIND | | SULFONE COMPOUND KIND | WT % | DISCHARGE CAPACITY RETENTION RATIO (%) |
|---|---|---|---|---|---|---|
| EXAMPLE 18-2 | LiPF$_6$ 1 mol/kg | EC + DEC | | CHEMICAL FORMULA 50(7) | 1 | 48 |
| EXAMPLE 19-1 | | EC + DEC | VC | | | 78 |
| EXAMPLE 19-2 | | | FEC | | | 74 |
| EXAMPLE 19-3 | | | t-DFEC | | | 82 |
| EXAMPLE 19-4 | | | c-DFEC | | | 82 |
| EXAMPLE 19-5 | | | PRS | | | 62 |
| EXAMPLE 19-6 | | | SBAH | | | 64 |
| EXAMPLE 19-7 | | EC + DEC + PC | FEC | | | 75 |
| EXAMPLE 19-8 | | | t-DFEC | | | 83 |
| COMPARATIVE EXAMPLE 19-1 | LiPF$_6$ 1 mol/kg | EC + DEC | VC | — | — | 68 |
| COMPARATIVE EXAMPLE 19-2 | | | FEC | | | 60 |

As shown in Table 19, in the case where silicon was used as the anode active material, the same results as those in Table 16 were obtained. In other words, in Examples 19-1 to 19-8 in which the solvent included VC or the like, the discharge capacity retention ratio was higher than that in Examples 18-2 in which VC or the like was not included. In this case, in the case where t-DFEC or c-DFEC was included, the discharge capacity retention ratio was higher than that in the case where FEC was included, and in the case where PC was included, a high discharge capacity retention ratio was obtained. In Examples 19-1 and 19-2 in which the solvent included the compound represented by Chemical Formula 50(7), the discharge capacity retention ratio was higher than that in Comparative Examples 19-1 and 19-2 in which the compound represented by Chemical Formula 50(7) was not included.

Therefore, it was confirmed that in the secondary battery according to the embodiment, when the solvent included the cyclic carbonate including an unsaturated bond, the cyclic carbonate represented by Chemical Formula 21 which included a halogen, the sultone or the acid anhydride, the cycle characteristics were further improved, or when the solvent included propylene carbonate, the cycle characteristics were improved.

Examples 20-1 and 20-2

Secondary batteries were formed by the same steps as those in Examples 17-1 and 17-2, except that as in the case of Examples 18-1 to 18-7, silicon was used to form the anode active material layer 34B.

Comparative Example 20

A secondary battery was formed by the same steps as those in Comparative Example 17, except that as in the case of Examples 18-1 to 18-7, silicon was used to form the anode active material layer 34B.

When the cycle characteristics of the secondary battery of Examples 20-1 and 20-2 and Comparative Example 20 were determined, results shown in Table 20 were obtained.

TABLE 20

Anode active material: silicon

| | ELECTROLYTE SALT | | SOLVENT KIND | SULFONE COMPOUND KIND | WT % | DISCHARGE CAPACITY RETENTION RATIO (%) |
|---|---|---|---|---|---|---|
| EXAMPLE 18-2 | LiPF$_6$ 1 mol/kg | | EC + DEC | CHEMICAL FORMULA 50(7) | 1 | 48 |
| EXAMPLE 20-1 | LiPF$_6$ 0.9 mol/kg | LIBF$_4$ 0.1 mol/kg | | | | 63 |
| EXAMPLE 20-2 | LiPF$_6$ 0.9 mol/kg | CHEMICAL FORMULA 27(6) 0.1 mol/kg | | | | 62 |
| COMPARATIVE EXAMPLE 20 | LiPF$_6$ 0.9 mol/kg | LIBF$_4$ 0.1 mol/kg | EC + DEC | — | — | 53 |

As shown in Table 20, in the case where silicon was used as the anode active material, the same results as those in Table 17 were obtained. In other words, in Examples 20-1 and 20-2 in which the electrolyte salt included lithium tetrafluoroborate or the like, the discharge capacity retention ratio was higher than that in Example 18-2 in which lithium tetrafluoroborate or the like was not included. In Example 20-1 in which the solvent included the compound represented by Chemical Formula 50(7), the discharge capacity retention ratio was higher than that in Comparative Example 20 in which the compound represented by Chemical Formula 50(7) was not included.

Therefore, it was confirmed that in the secondary battery according to the embodiment, when the electrolyte salt included lithium tetrafluoroborate or the compound represented by Chemical Formula 24, the cycle characteristics were further improved.

It was confirmed from the above-described results shown in Tables 15 to 20 that in the secondary battery according to the embodiment, when the solvent of the electrolytic solution included the sulfone compound represented by Chemical Formula 49, irrespective of the kind of the anode active material or the composition of the solvent, the cycle characteristics were improved. It was confirmed that in this case, in the case where silicon was used as the anode active material, the rate of increase of the discharge capacity retention ratio was larger than that in the case where the carbon material was used as the anode active material, so a higher effect was obtained in the case where silicon was used. It was considered that the result was obtained, because when silicon which was advantageous to increase the capacity was used as the anode active material, compared to the case where the carbon material was used, the electrolytic solution was easily decomposed, so the decomposition inhibition effect of the electrolytic solution was exerted pronouncedly.

Although several embodiments and examples have been described, the embodiments and the examples may be variously modified. For example, the application of the electrolytic solution of the present application is not limited to batteries, and the electrolytic solution may be applied to any other electrochemical devices in addition to the batteries. As the other application, for example, a capacitor or the like is cited.

Moreover, in the above-described embodiments and the above-described examples, the case where the electrolytic solution or the gel electrolyte in which the polymer compound holds the electrolytic solution is used as the electrolyte of the battery of the present application is described. However, any other kind of electrolyte may be used. Examples of the electrolyte include a mixture of an ion-conducting inorganic compound such as ion-conducting ceramic, ion-conducting glass or ionic crystal and an electrolytic solution, a mixture of another inorganic compound and an electrolytic solution, a mixture of the inorganic compound and a gel electrolyte, and the like.

Moreover, in the above-described embodiments and the above-described examples, as the battery, a lithium-ion secondary battery in which the capacity of the anode is represented on the basis of insertion and extraction of lithium, and a lithium metal secondary battery in which the capacity of the anode is represented on the basis of precipitation and dissolution of lithium are described. However, the present application is not necessarily limited to them. The battery of the present application is applicable to a secondary battery in which the charge capacity of an anode material capable of inserting and extracting lithium is smaller than the charge capacity of a cathode, thereby the capacity of the anode includes a capacity based on insertion and extraction of lithium and a capacity based on precipitation and dissolution of lithium, and is represented by the sum of them in the same manner.

In the above-described embodiments and the above-described examples, the case where lithium is used as an electrode reactant is described. However, any other Group 1A element in the short form of the periodic table of the elements such as sodium (Na) or potassium (K), a Group 2A element in the short form of the periodic table of the elements such as magnesium or calcium (Ca), or any other light metal such as aluminum may be used. Also in this case, as the anode active material, the anode material described in the above-described embodiments may be used.

Further, in the above-described embodiments and the above-described examples, the case where the battery has a cylindrical type and a laminate film type and the case where a battery device has a spirally wound configuration are described as examples. However, the battery of the present application is applicable to the case where a battery has any other shape such as a prismatic type, a coin type or a button type or the case where the battery device has any other configuration such as a laminate configuration in the same manner. Moreover, the present application is applicable to not only the secondary batteries but also other kinds of batteries such as primary batteries.

In the above-described embodiments and the above-described examples, an appropriate range, which is derived from the results of the examples, of the content of the compounds represented by Chemical formula 11 in the electrolytic solution or the battery is described. However, the description does not exclude the possibility that the content is out of the above-described range. More specifically, the above-described appropriate range is a specifically preferable range to obtain the effects, and as long as the effects of the present application are obtained, the content may be deviated from the above-described range to some extent. The same holds for the sulfone compound represented by Chemical Formula 35 or Chemical Formula 49.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A secondary battery comprising a cathode, an anode and an electrolytic solution,
wherein the electrolytic solution includes a solvent including a sulfone compound selected from the group consisting of compounds represented by Chemical Formulae 41(1) to 41(8) and a cyclic carbonate selected from the group consisting of 4-fluoro-1,3-dioxolan-2-one, trans-4,5-difluoro-1,3-dioxolan-2-one and cis-4,5-difluoro-1,3-dioxolan-2-one:

Chemical Formula 41

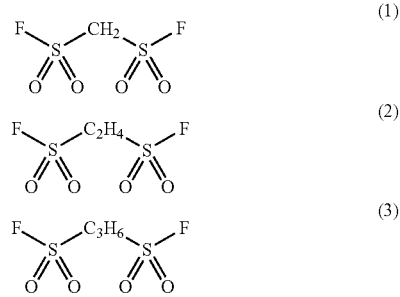

-continued

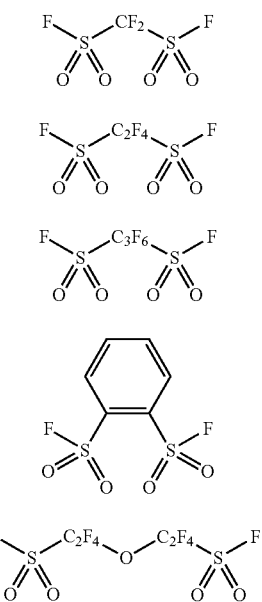

wherein a content of the sulfone compound in the solvent is within a range from 1 wt % to 10 wt % both inclusive, wherein the anode includes an anode active material including at least silicon, and wherein a content of the cyclic carbonate ranges from 1 wt % to 5 wt %.

2. A secondary battery comprising:

a cathode;

an anode;

an electrolytic solution; and an electrolyte salt including at least one kind selected from the group consisting of compounds represented by Chemical Formulas 46, 47 and 48:

Chemical Formula 46

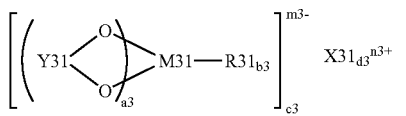

where X31 represents a Group 1A element or a Group 2A element in the short form of the periodic table of the elements, or aluminum, M31 represents a transition metal, or a Group 3B element, a Group 4B element or a Group 5B element in the short form of the periodic table of the elements, R31 represents a halogen group, Y31 represents —OC—R32-CO—, —OC—CR33$_2$- or —OC—CO—, in which R32 represents an alkylene group, a halogenated alkylene group, an arylene group or a halogenated arylene group, and R33 represents an alkyl group, a halogenated alkyl group, an aryl group or a halogenated aryl group, and a3 is an integer of 1 to 4 both inclusive, and b3 is 0 or an integer of 2 or 4, and c3, d3, m3 and n3 each are an integer of 1 to 3 both inclusive, Chemical Formula 47

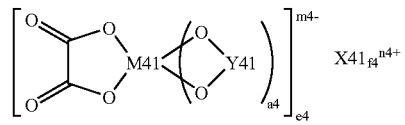

where X41 represents a Group 1A element or a Group 2A element in the short form of the periodic table of the elements, M41 represents a transition metal, or a Group 3B element, a Group 4B element or a Group 5B element in the short form of the periodic table of the elements, Y41 represents —OC—(CR41$_2$)$_{b4}$-CO—, R43$_2$C—(CR42$_2$)$_{c4}$-CO—, R43$_2$C—(CR42$_2$)$_{c4}$-CR43$_2$-, —R43$_2$C—(CR42$_2$)$_{c4}$-SO$_2$—, —O$_2$S—(CR42$_2$)$_{d4}$-SO$_2$— or —OC—(CR42$_2$)$_{d4}$-SO$_2$—, in which R41 and R43 each represent a hydrogen group, an alkyl group, a halogen group or a halogenated alkyl group and at least one of them is a halogen group or a halogenated alkyl group, and R42 represents a hydrogen group, an alkyl group, a halogen group or a halogenated alkyl group, and a4, e4 and n4 each are an integer of 1 or 2, b4 and d4 each are an integer of 1 to 4 both inclusive, c4 is 0 or an integer of 1 to 4 both inclusive, and f4 and m4 each are an integer of 1 to 3 both inclusive, Chemical Formula 48

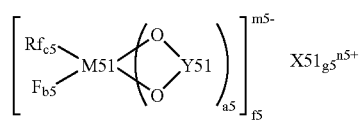

where X51 represents a Group 1A element or a Group 2A element in the short form of the periodic table of the elements, M51 represents a transition metal, or a Group 3B element, a Group 4B element or a Group 5B element in the short form of the periodic table of the elements, Rf represents a fluorinated alkyl group having 1 to 10 carbon atoms or a fluorinated aryl group having 1 to 10 carbon atoms, Y51 represents —OC—(CR51$_2$)$_{d5}$-CO—, —R52$_2$C—(CR51$_2$)$_{d5}$-CO—, —R52$_2$C—(CR51$_2$)$_{d5}$-CR52$_2$-, —R52$_2$C—(CR51$_2$)$_{d5}$-SO$_2$—, —O$_2$S—(CR51$_2$)$_{e5}$-SO$_2$— or —OC—(CR51$_2$)$_{e5}$-SO$_2$—, in which R51 represents a hydrogen group, an alkyl group, a halogen group or a halogenated alkyl group, and R52 represents a hydrogen group, an alkyl group, a halogen group or a halogenated alkyl group and at least one of them is a halogen group or a halogenated alkyl group, and a5, f5 and n5 each are an integer of 1 or 2, b5, c5 and e5 each are an integer of 1 to 4 both inclusive, d5 is 0 or an integer of 1 to 4 both inclusive, and g5 and m5 each are an integer of 1 to 3 both inclusive, wherein the electrolytic solution includes a solvent including a sulfone compound selected from the group consisting of compounds represented by Chemical Formulae 41(1) to 41(8) and a cyclic carbonate selected from the group consisting of 4-fluoro-1,3-dioxolan-2-one, trans-4,5-difluoro-1,3-dioxolan-2-one and cis-4,5-difluoro-1,3-dioxolan-2-one:

Chemical Formula 41

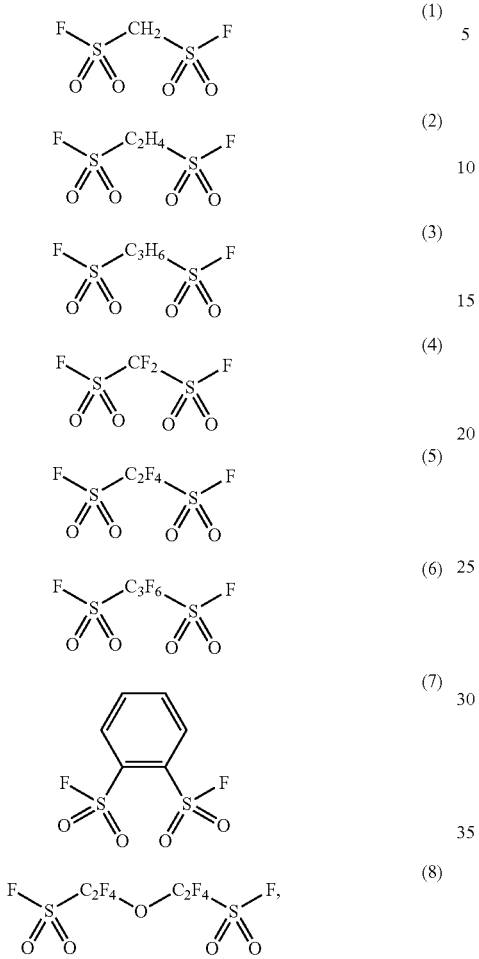

(1)
(2)
(3)
(4)
(5)
(6)
(7)
(8)

wherein a content of the sulfone compound in the solvent is within a range from 1 wt % to 10 wt % both inclusive, wherein the anode includes an anode active material including at least silicon, and wherein a content of the cyclic carbonate ranges from 1 wt % to 5 wt %.

3. The secondary battery according to claim 2, wherein the compound represented by Chemical Formula 46 is at least one kind selected from the group consisting of compounds represented by Chemical Formula 49, the compound represented by Chemical Formula 47 is at least one kind selected from the group consisting of compounds represented by Chemical Formula 50, and the compound represented by Chemical Formula 48 is a compound represented by Chemical Formula 51:

Chemical Formula 49

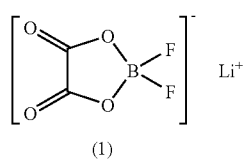

(1)

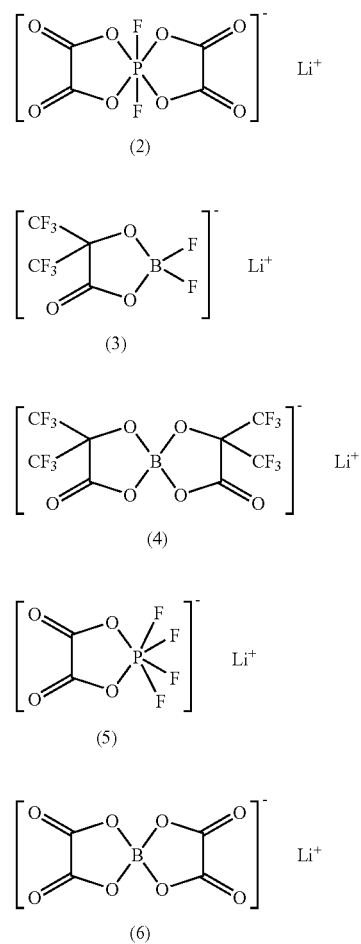

(2)
(3)
(4)
(5)
(6)

Chemical Formula 50

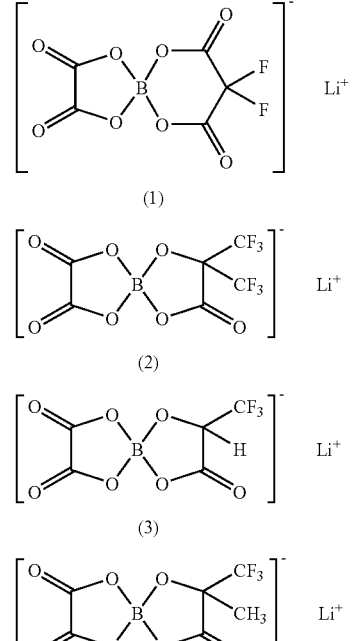

(1)
(2)
(3)
(4)

-continued

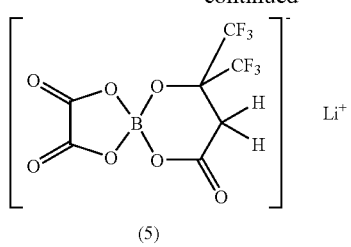

(5)

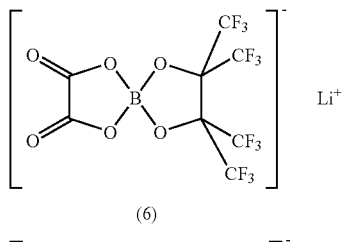

(6)

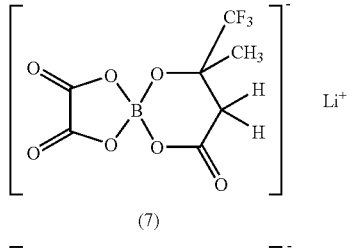

(7)

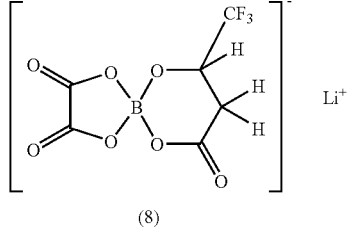

(8)

Chemical Formula 51

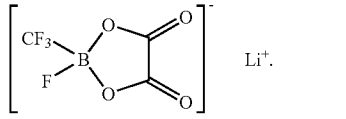

4. The secondary battery according to claim 1, wherein the sulfone compound is selected from the group consisting of Chemical Formula 19(2), Chemical Formula 19(4) and Chemical Formula 19(5):

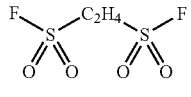
(2)

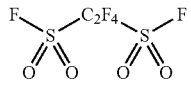
(4)

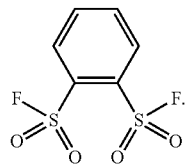
(5)

5. The secondary battery according to claim 1, wherein the cyclic carbonate is selected from the group consisting of trans-4,5-difluoro-1,3-dioxolan-2-one and cis-4,5-difluoro-1,3-dioxolan-2-one.

6. The secondary battery according to claim 1, wherein the solvent includes at least one of a sultone and an acid anhydride.

7. The secondary battery according to claim 1, wherein the electrolytic solution comprises an electrolyte salt including at least one kind selected from the group consisting of: $LiPF_6$, $LiBF_4$, $LiClO_4$ and $LiAsF_6$.

8. The secondary battery according to claim 1, wherein the electrolytic solution comprises an electrolyte salt including at least one kind selected from the group consisting of compounds represented by Chemical Formulas 46, 47 and 48:

Chemical Formula 46

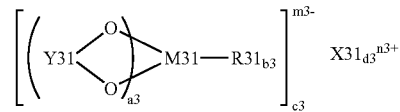

where X31 represents a Group 1A element or a Group 2A element in the short form of the periodic table of the elements, or aluminum, M31 represents a transition metal, or a Group 3B element, a Group 4B element or a Group 5B element in the short form of the periodic table of the elements, R31 represents a halogen group, Y31 represents —OC—R32-CO—, —OC—$CR33_2$- or —OC—CO—, in which R32 represents an alkylene group, a halogenated alkylene group, an arylene group or a halogenated arylene group, and R33 represents an alkyl group, a halogenated alkyl group, an aryl group or a halogenated aryl group, and a3 is an integer of 1 to 4 both inclusive, and b3 is 0 or an integer of 2 or 4, and c3, d3, m3 and n3 each are an integer of 1 to 3 both inclusive, Chemical Formula 47

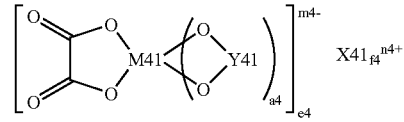

where X41 represents a Group 1A element or a Group 2A element in the short form of the periodic table of the elements, M41 represents a transition metal, or a Group 3B element, a Group 4B element or a Group 5B element in the short form of the periodic table of the elements, Y41 represents —OC—$(CR41_2)_{b4}$-CO—, —$R43_2C$—$(CR42_2)_{c4}$-CO—, —$R43_2C$—$(CR42_2)_{c4}$-$CR43_2$-, —$R43_2C$—$(CR42_2)_{c4}$-$SO_2$—, —$O_2S$—$(CR42_2)_{d4}$-$SO_2$— or —OC—$(CR42_2)_{d4}$-$SO_2$—, in which R41 and R43 each represent a hydrogen group, an alkyl group, a halogen group or a halogenated alkyl group and at least one of them is a halogen group or a halogenated alkyl group, and R42 represents a hydrogen group, an alkyl group, a halogen group or a halogenated alkyl group, and a4, e4 and n4 each are an integer of 1 or 2, b4 and d4 each are an integer of 1 to 4 both inclusive, c4 is 0 or an integer of 1 to 4 both inclusive, and f4 and m4 each are an integer of 1 to 3 both inclusive, Chemical Formula 48

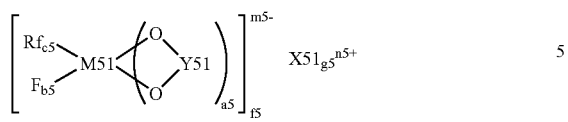

where X51 represents a Group 1A element or a Group 2A element in the short form of the periodic table of the elements, M51 represents a transition metal, or a Group 3B element, a Group 4B element or a Group 5B element in the short form of the periodic table of the elements, Rf represents a fluorinated alkyl group having 1 to 10 carbon atoms or a fluorinated aryl group having 1 to 10 carbon atoms, Y51 represents —OC—(CR51$_2$)$_{d5}$-CO—, —R52$_2$C—(CR51$_2$)$_{d5}$-CO—, —R52$_2$C—(CR51$_2$)$_{d5}$-CR52$_2$-, —R52$_2$C—(CR51$_2$)$_{d5}$-SO$_2$—, —O$_2$S—(CR51$_2$)$_{e5}$-SO$_2$— or —OC—(CR51$_2$)$_{e5}$-SO$_2$—, in which R51 represents a hydrogen group, an alkyl group, a halogen group or a halogenated alkyl group, and R52 represents a hydrogen group, an alkyl group, a halogen group or a halogenated alkyl group and at least one of them is a halogen group or a halogenated alkyl group, and a5, f5 and n5 each are an integer of 1 or 2, b5, c5 and e5 each are an integer of 1 to 4 both inclusive, d5 is 0 or an integer of 1 to 4 both inclusive, and g5 and m5 each are an integer of 1 to 3 both inclusive.

9. The secondary battery according to claim 8, wherein the compound represented by Chemical Formula 46 is at least one kind selected from the group consisting of compounds represented by Chemical Formula 49, the compound represented by Chemical Formula 47 is at least one kind selected from the group consisting of compounds represented by Chemical Formula 50, and the compound represented by Chemical Formula 48 is a compound represented by Chemical Formula 51:

Chemical Formula 49

(1)

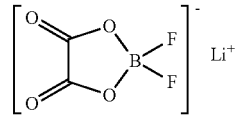

(2)

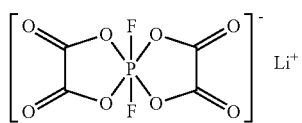

(3)

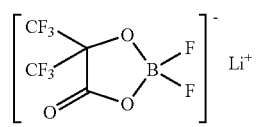

(4)

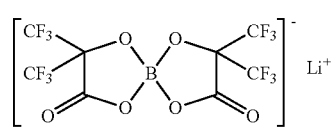

(5)

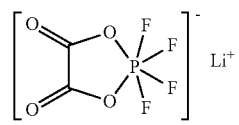

(6)

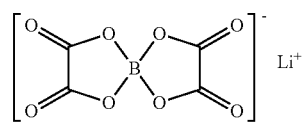

Chemical Formula 50

(1)

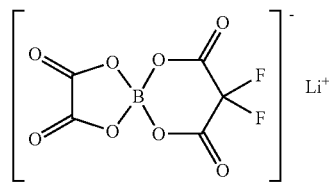

(2)

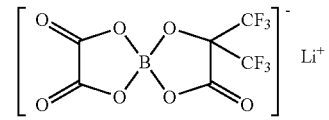

(3)

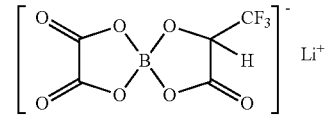

(4)

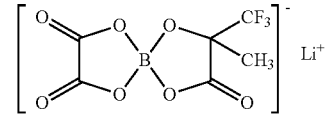

(5)

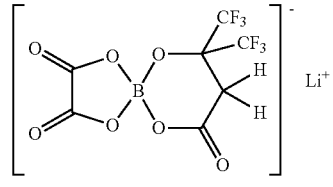

(6)

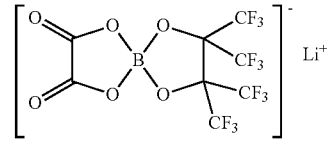

(7)

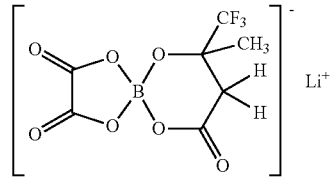

-continued

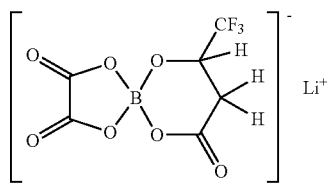

(8)

Chemical Formula 51

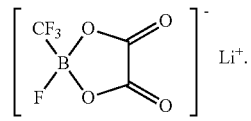

10. The secondary battery according to claim 1, wherein the electrolytic solution comprises an electrolyte salt including at least one kind selected from the group consisting of compounds represented by Chemical Formulas 52, 53 and 54:

$LiN(C_mF_{2m+1}SO_2)(C_nF_{2n+1}SO_2)$  Chemical Formula 52 where m and n each are an integer of 1 or more,

Chemical Formula 53

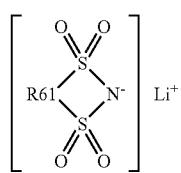

Chemical Formula 53 where R61 represents a straight-chain or branched perfluoroalkylene group having 2 to 4 carbon atom, $LiC(C_pF_{2p+1}SP_2)(C_qF_{2q+1}SO_2)(C_rF_{2r+1}SO)$  Chemical Formula 54 where p, q and r each are an integer of 1 or more.

11. The secondary battery according to claim 1, wherein:
the anode includes an anode active material layer on an anode current collector, and
the anode active material layer is formed by at least one kind of method selected from the group consisting of a vapor-phase method, a liquid-phase method and a firing method.

* * * * *